United States Patent [19]

Sasho et al.

[11] Patent Number: 5,151,417
[45] Date of Patent: Sep. 29, 1992

[54] 3-SUBSTITUTED VINYL CEPHALOSPORIN DERIVATIVES

[75] Inventors: Manabu Sasho; Hiroshi Yamauchi, both of Ibaraki; Motosuke Yamanaka; Takaharu Nakamura, both of Chiba; Kanemasa Katsu, Ibaraki; Isao Sugiyama, Ibaraki; Yuuki Komatu, Ibaraki; Shigeto Negi, Ibaraki, all of Japan

[73] Assignee: Eisai Co., Ltd., Tokyo, Japan

[21] Appl. No.: 550,365

[22] Filed: Jul. 10, 1990

[30] Foreign Application Priority Data

| Jul. 13, 1989 | [JP] | Japan | 1-178989 |
| Jul. 18, 1989 | [JP] | Japan | 1-183689 |
| Sep. 22, 1989 | [JP] | Japan | 1-244928 |
| Oct. 13, 1989 | [JP] | Japan | 1-265153 |
| Feb. 5, 1990 | [JP] | Japan | 2-24413 |

[51] Int. Cl.$^5$ ............... C07D 501/32; A61K 31/545
[52] U.S. Cl. .................... 514/202; 540/222; 540/225
[58] Field of Search ............... 540/222, 226; 514/202, 514/206

[56] References Cited

U.S. PATENT DOCUMENTS

| 4,520,193 | 5/1985 | Berge et al. | 540/22 |
| 4,639,448 | 1/1987 | Takaya et al. | 540/222 |
| 4,731,362 | 3/1988 | Damashima et al. | 540/222 |
| 4,874,856 | 10/1989 | Iimula et al. | 540/222 |

*Primary Examiner*—Nicholas S. Rizzo
*Attorney, Agent, or Firm*—Wenderoth, Lind & Ponack

[57] ABSTRACT

3-Substituted vinyl cephalosporin derivatives represented by the following formula:

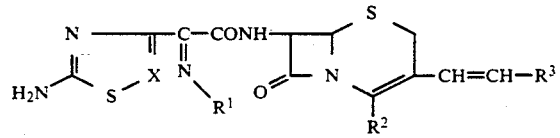

wherein $R^1$ represents a hydroxyl or lower alkoxyl group, X represents a nitrogen atom or a group represented by the formula —CH=, $R^2$ represents a carboxyl group or a carboxyl group protected with a protecting group, and $R^3$ is as defined herein, and pharmaceutically acceptable salts thereof are potent antibacterial agents. Processes for their preparation, intermediates in such processes, and antibacterial compositions containing them as active ingredients are also described.

12 Claims, No Drawings

3-SUBSTITUTED VINYL CEPHALOSPORIN DERIVATIVES

BACKGROUND OF THE INVENTION

1) Field of the Invention

The present invention relates to novel 3-substituted vinyl cephalosporin derivatives having excellent activities as medicine.

2) Description of the Related Art

The following derivatives have been known as compounds with a substituted or unsubstituted vinyl group introduced at the 3-position of a thiazolylacetamidecephem derivative.

European Patent Application No. 30630 discloses 7-acylamino-3-vinylcephalosporan derivatives, including compounds represented by the following formula:

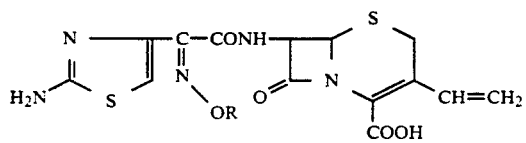

wherein R is a lower alkyl, lower alkenyl, lower alkynyl or carboxy-lower alkyl group.

Further, Japanese Patent Application Laid-open No. 89089/1984 discloses, as 7-substituted-3-vinyl-3-cephem compounds, compounds represented by the following formula:

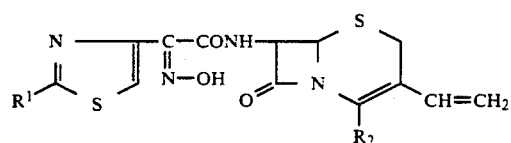

wherein $R^1$ represents an amino group or an amino group protected with one or more protecting groups and $R^2$ represents a carboxyl group or a carboxyl group protected with a protecting group.

On the other hand, Japanese Patent Application Laid-open No. 491/1987 discloses a compound represented by the following formula:

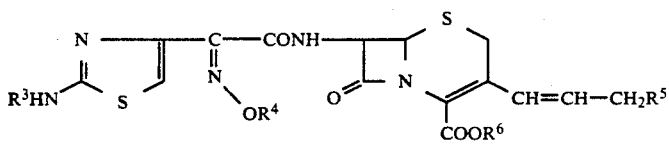

wherein $R^3$ is a hydrogen atom or an ordinary amino-protecting group, $R^4$ is a hydrogen atom or a linear or branched alkyl group having 1-4 carbon atoms, an alkenyl or alkynyl group having 2-4 carbon atoms, a cycloalkyl group having 3-6 carbon atoms, a cycloalkylalkyl group having a 3-6 membered ring or 4-10 carbon atoms or an alkanoyl group having 2-4 carbon atoms, $R^5$ is a hydrogen atom or a lower alkyl group having 1-3 carbon atoms, a lower alkoxyl group having 1-3 carbon atoms or a lower alkanoyloxy group having 2-3 carbon atoms, and $R^6$ is a hydrogen atom or a physiologically hydrolyzable ester group, for example, an acetoxymethyl, 1-acetoxyethyl, pivaloyloxymethyl, 5-methyl-2-oxo-1,3-dioxolan-4-ylmethyl, 1-(ethoxycarbonyloxy)ethyl or 4-glycyloxybenzoyloxymethyl group.

However, sufficient antibacterial activities are not available from any of these compounds and therefore, there is a strong desire for the development of still more effective derivatives.

SUMMARY OF THE INVENTION

The present inventors have hence proceeded with an exhaustive investigation for a long time with a view toward developing still better 3-substituted vinyl cephalosporin derivatives. As a result, it has been found that 3-substituted vinyl cephalosporin derivatives to be described below have excellent antibacterial activities. Namely, it has been found that these 3-substituted vinyl cephalosporin derivatives have high activities against various pathogenic microorganisms and are useful especially as orally-administrable antibacterial agents, leading to the completion of the present invention.

The present invention therefore provides 3-substituted vinyl cephalosporin derivatives represented by the following formula (I) and pharmaceutically acceptable salts thereof.

Formula (I):

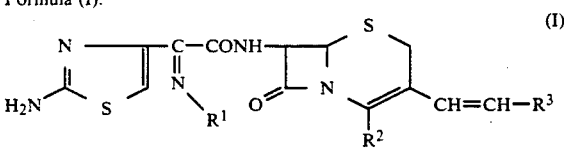

wherein $R^1$ represents a hydroxyl or lower alkoxyl group;

X represents a nitrogen atom or a group represented by the formula $-CH=$;

$R^2$ represents a carboxyl group or a carboxyl group protected with a protecting group; and $R^3$ represents:

(1) a cycloalkyl group, (2) a group represented by the formula $-CH_2OCONHR^4$ wherein $R^4$ is a hydrogen atom, a lower alkyl group, a halogenated lower alkyl group or a lower alkenyl group, (3) a group represented by the formula

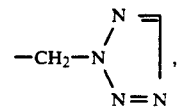

(4) a group represented by the formula

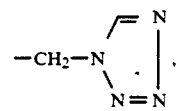

(5) a group represented by the formula

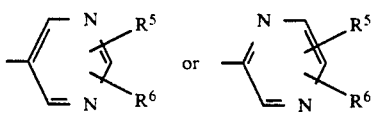

wherein $R^5$ and $R^6$ are the same or different and are individually a hydrogen atom, a lower alkyl group, a lower alkoxyl group, an amino group or a halogen atom, (6) a group represented by the formula

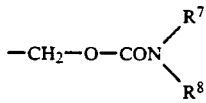

wherein $R^7$ and $R^8$ are the same or different and are individually a hydrogen atom, a lower alkyl group, a halogenated lower alkyl group or a lower alkenyl group or $R^7$ and $R^8$ may form a morpholino ring together with the nitrogen atom to which $R^7$ and $R^8$ are bonded, or (7) a group represented by the formula

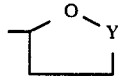

wherein Y is a group represented by the formula

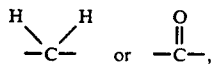

with the proviso that when X is a nitrogen atom, $R^3$ stands only for a group represented by the formula

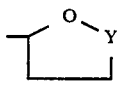 (7)

wherein Y has the same meaning as defined above.

The compounds of the present invention have excellent antibacterial activities and are useful especially as orally-administrable antibacterial agents.

DETAILED DESCRIPTION OF THE INVENTION AND PREFERRED EMBODIMENTS

In the above definition of the present invention, exemplary lower alkyl groups represented by $R^1$, $R^4$, $R^5$, $R^6$, $R^7$ and $R^8$ include 1-6 linear or branched alkyl groups, such as methyl, ethyl, n-propyl, isopropyl, n-butyl, isobutyl, sec-butyl, tert-butyl, n-pentyl (amyl), isopentyl, neopentyl, tert-pentyl, 1-methylbutyl, 2-methylbutyl, 1,2-dimethylpropyl, n-hexyl, isohexyl, 1-methylpentyl, 2-methylpentyl, 3-methylpentyl, 1,1-dimethylbutyl, 1,2-dimethylbutyl, 2,2-dimethylbutyl, 1,3-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl and 1-ethyl-2-methyl propyl. Among these groups, methyl, ethyl, propyl and isopropyl groups are preferred and of these, particularly preferred are methyl and ethyl groups.

In addition, exemplary lower alkoxyl groups represented by $R^1$, $R^5$ and $R^6$ include lower alkoxyl groups derived from the above lower alkyl groups, such as methoxy, ethoxy, n-propoxy, i-propoxy, n-butoxy, sec-butoxy and t-butoxy, with a methoxy group being most preferred.

Halogen atoms represented by $R^5$ and $R^6$ mean chlorine, bromine and fluorine atoms.

In the definition of $R^4$, the term "halogenated lower alkyl group" means a lower alkyl group such as that defined above, in which any one or more of the hydrogen atoms are substituted by halogen atoms, in particular, fluorine atoms.

In addition, illustrative of the cycloalkyl groups include cycloalkyl groups having 3–6 carbon atoms, with a cyclopropyl group being most preferred.

$R^2$ represents a carboxyl group or a carboxyl group protected with a protecting group. Exemplary protecting groups for the carboxyl group include lower alkyl groups such as methyl, ethyl and t-butyl; substituted or unsubstituted, phenyl-substituted lower alkyl groups such as p-methoxybenzyl, p-nitrobenzyl, 3,4-dimethoxybenzyl, diphenylmethyl, trityl and phenethyl; halogenated lower alkyl groups such as 2,2,2-trichloroethyl and 2-iodoethyl; lower alkanoyloxy-lower alkyl groups such as pivaloyloxymethyl, acetoxymethyl, propionyloxymethyl, butyryloxymethyl, valeryloxymethyl, 1-acetoxyethyl, 2-acetoxyethyl, 1-pivaloyloxyethyl and 2-pivaloyloxyethyl; higher alkanoyloxy-lower alkyl groups such as palmitoyloxyethyl, heptapecanoyloxymethyl and 1-palmitoyloxyethyl; lower alkoxy-carbonyloxy-lower alkyl groups such as methoxycarbonyloxymethyl, 1-butoxycarbonyloxyethyl, 1-t-butoxycarbonyloxyethyl, 1-ethoxycarbonyloxyethyl and 1-(isopropoxycarbonyloxy)ethyl; carboxy-lower alkyl groups such as carboxymethyl and 2-carboxyethyl; heterocyclic groups such as 3-phthalidyl; substituted or unsubstituted benzoyloxy-lower alkyl groups such as 4-glycyloxybenzoyloxymethyl and 4-[N-(t-butoxycarbonyl)glycyloxy]benzoyloxymethyl; (substituted dioxolane)-lower alkyl groups such as (5-methyl-2-oxo-1,3-dioxolen-4-yl)methyl; cycloalkyl-substituted lower alkanoyloxy-lower alkyl groups such as 1-cyclohexylacetyloxyethyl, and cycloalkyloxycarbonyloxy-lower alkyl groups such as 1-cyclohexyloxycarbonyloxyethyl. In short, any group may be employed as a protecting group as long as it can be removed by a suitable method to give a carboxylic acid.

Illustrative of the pharmaceutically acceptable salt include alkali metal salts such as sodium salt and potassium salt; quaternary ammonium salts such as ammonium salt, tetraethylammonium salt and betaine salt; alkaline earth metal salts such as calcium salt and magnesium salt; inorganic acid salts such as hydrochloride, hydrobromide, hydroiodide, sulfate, carbonate and bicarbonate; organic carboxylate salts such as acetate salt, maleate salt, lactate salt and tartrate salt; organic sulfonate salts such as methanesulfonate salt, hydroxymethanesulfonate salt, hydroxyethanesulfonate salt, taurine salt, benzenesulfonate salts and toluenesulfonates; amino acid salts such as arginine salt, lysine salt, serine salt, aspartate salt, glutamate salt and glycine salt; and amine salts such as trimethylamine salt, triethylamine salt, pyridine salt, procaine salt, picoline salt, dicyclohexylamine salt, N,N'-dibenyzlethylenediamine salt, N-methylglucamine salt, diethanolamine salt, triethanolamine salt, tris(hydroxymethylamino)methane salt and phenethylbenzylamine salt.

The compounds of the present invention can be produced by various processes, for example, by the following processes.

Production Process 1

[In the case where in the formula (I), X is group represented by the formula —CH= and $R^3$ is (2) a group represented by the formula —CH$_2$OCONHR$^4$ wherein $R^4$ has the same meaning as defined above, (3) a group represented by the formula

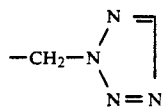

or (4) a group represented by the formula

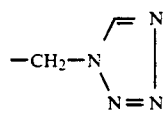

Compounds represented by the following formula (IV):

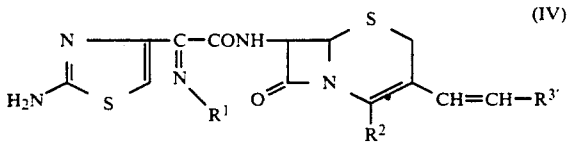

wherein $R^1$ and $R^2$ have the same meanings as defined above; $R^{3'}$ has the same meaning as $R^3$ as defined immediately above in the brackets under Production Process 1 and pharmaceutically acceptable salts thereof can each be obtained by reacting a compound represented by the following formula (II):

(II)

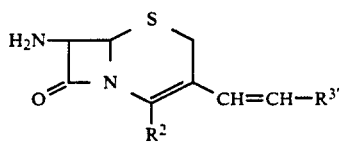

wherein $R^2$ and $R^{3'}$ have the same meanings as defined above, or a salt thereof with a compound represented by the following formula (III):

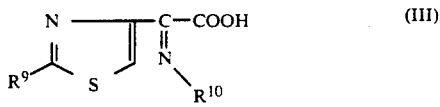

wherein $R^9$ represents an amino group or an amino group protected with protecting group(s) and $R^{10}$ represents a hydroxyl group, a lower alkoxyl group or a hydroxyl group protected with a protecting group, a reactive acid derivative or salt thereof; and removing the protecting group(s) of the amino, hydroxyl or carboxyl group as needed.

The above reaction can be conducted at a reaction temperature of from $-50°$ C. to $50°$ C. in an inert solvent such as dichloromethane, chloroform, tetrahydrofuran, acetone, ethyl acetate, dimethylsulfoxide, benzene, toluene or hexane. The removal of each protecting group can be effected by a conventional method, depending on the type of the protecting group used.

Introduction of a protecting group into the carboxyl group can be effected by conducting esterification in a usual manner.

Exemplary amino-protecting groups include formyl, acetyl, chloroacetyl, dichloroacetyl, phenylacetyl, thienylacetyl, t-butoxycarbonyl, benzyloxycarbonyl, trityl, p-methoxybenzyl, diphenylmethyl, benzylidene, p-nitrobenzylidene, m-nitrobenzylidene, 3,4-methylenedioxybenzylidene and m-chlorobenzylidene groups.

Illustrative hydroxyimino-protecting groups $R^{10}$ include trityl and tetrahydropiranyl groups.

When $R^3$ is (2) a group represented by the formula —CH$_2$OCONHR$^4$ wherein $R^4$ has the same meaning as defined above, the following process can also be employed.

Compounds represented by the following formula (VI):

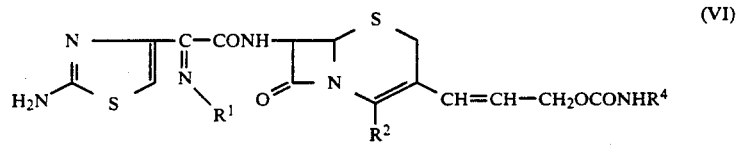

wherein $R^1$, $R^2$ and $R^4$ have the same meanings as defined above and pharmaceutically acceptable salts thereof can each be obtained by reacting a compound represented by the following formula (V):

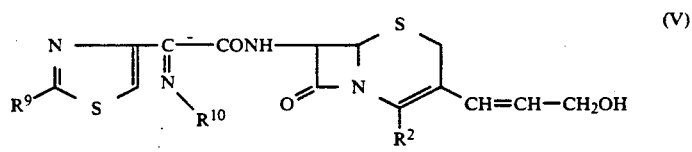

wherein $R^2$, $R^9$ and $R^{10}$ have the same meanings as defined above, or a salt thereof with an alkyl isocyanate represented by the formula $R^4$—N=C=O wherein $R^4$ has the same meaning as defined above; and removing the protecting group(s) of the amino, hydroxyl or carboxyl groups as needed.

The above reaction can be conducted at a reaction temperature of from −10° C. to 50° C. in an inert solvent such as dichloromethane, chloroform, tetrahydrofuran, acetone, ethyl acetate, methanol, ethanol, dimethylsulfoxide, benzene, toluene or hexane. The removal of each protecting group can be effected by a conventional method, depending on the type of the protecting group used.

Exemplary amino-protecting groups include formyl, acetyl, chloroacetyl, dichloroacetyl, phenylacetyl, thienylacetyl, t-butoxycarbonyl, benzyloxycarbonyl, trityl, p-methoxybenzyl, diphenylmethyl, benzylidene, p-nitrobenzylidene, m-nitrobenzylidene, 3,4-methylenedioxybenzylidene and m-chlorobenzylidene groups.

Illustrative hydroxyimino-protecting groups include trityl and tetrahydropiranyl groups.

When $R^4$ is a hydrogen atom in the formula (I), the process described above can be followed.

Namely, compounds represented by the following formula (VIII):

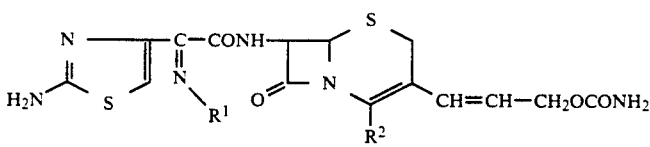

(VIII)

wherein $R^1$ and $R^2$ have the same meanings as defined above and pharmaceutically acceptable salts thereof can each be obtained by reacting a compound represented by the following formula (VII):

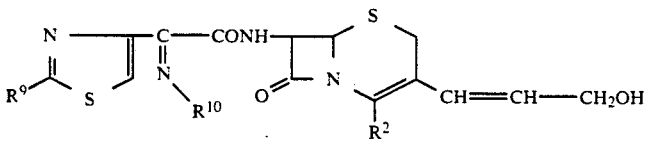

(VII)

wherein $R^9$, $R^{10}$ and $R^2$ have the same meanings as defined above, or a salt thereof with a halogenated sulfonylisocyanate; and removing the protecting group(s) of the amino, hydroxyl or carboxyl group(s) as needed.

Production Process 2

[In the case where in the formula (I), X is a group represented by the formula —CH= and $R^3$ represents (1) a cycloalkyl group, (5) a group represented by the formula

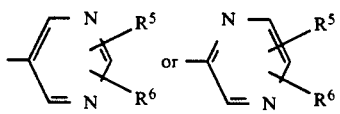

wherein $R^5$ and $R^6$ have the same meanings as defined above, (6) a group represented by the formula

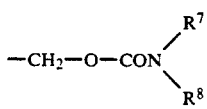

wherein $R^7$ and $R^8$ have the same meanings as defined above or (7) a group represented by the formula

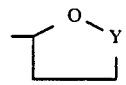

wherein Y has the meaning as defined above]

Compounds represented by the following formula (XI):

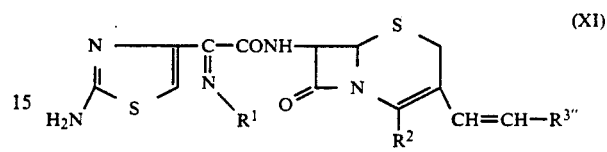

wherein $R^1$ and $R^2$ have the same meanings as defined above and $R^{3''}$ has the same meaning as $R^3$ as defined immediately above in the brackets under Production Process 2 and pharmaceutically acceptable salts thereof can each be obtained by reacting a compound represented by the following formula (IX):

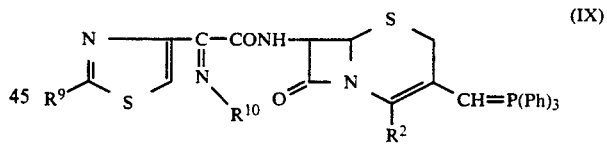

(IX)

wherein $R^9$ represents an amino group or an amino group protected with a protecting group, $R^{10}$ represents a hydroxyl group, a hydroxyl group protected with a protecting group or a lower alkoxyl group, $R^2$ has the same meaning as defined above and Ph represents a phenyl group, or a salt thereof with a compound represented by the following formula (X):

(X)

wherein $R^{3''}$ has the same meaning as defined above; and removing the protecting groups of the amino, hydroxyl or carboxyl group(s) as needed.

The above reaction can be conducted at a reaction temperature of from −10° C. to 50° C. in an inert solvent such as dichloromethane, chloroform, tetrahydrofuran, acetone, ethyl acetate, methanol, ethanol, dimethylsulfoxide, benzene, toluene or hexane. The removal of each protecting group can be effected by a conventional method, depending on the type of the protecting group used.

Exemplary amino-protecting groups of $R^1$ include formyl, acetyl, chloroacetyl, dichloroacetyl, phenylacetyl, thienylacetyl, t-butoxycarbonyl, benzyloxycarbonyl, trityl, p-methoxybenzyl, diphenylmethyl, benzylidene, p-nitrobenzylidene, m-nitrobenzylidene, 3,4-methylenedioxybenzylidene and m-chlorobenzylidene groups.

Illustrative hydroxy-protecting groups of $R^1$ include trityl and tetrahydropiranyl groups.

In connection with Production Process 2, the following specific reaction schemes can be described by way of example:

(A)

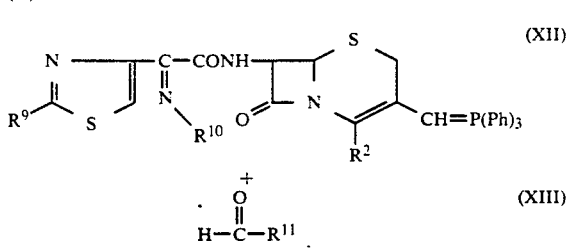

wherein $R^{11}$ represents a cycloalkyl group.

(XIX)

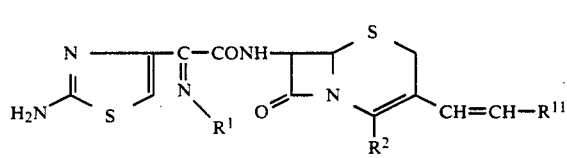

(B)

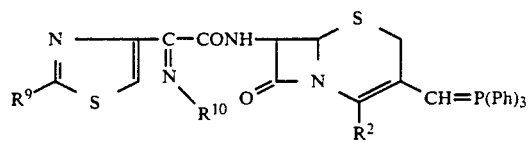

+

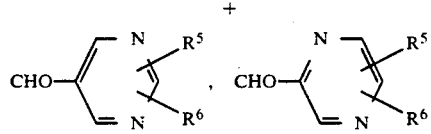

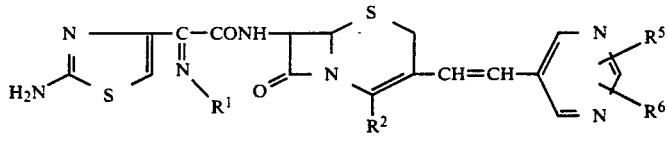

or

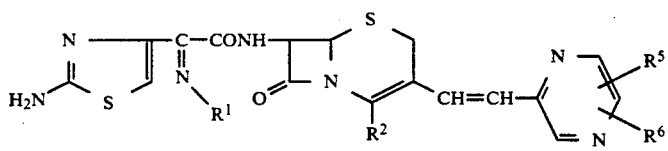

(C)

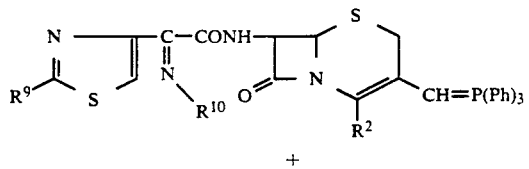

+

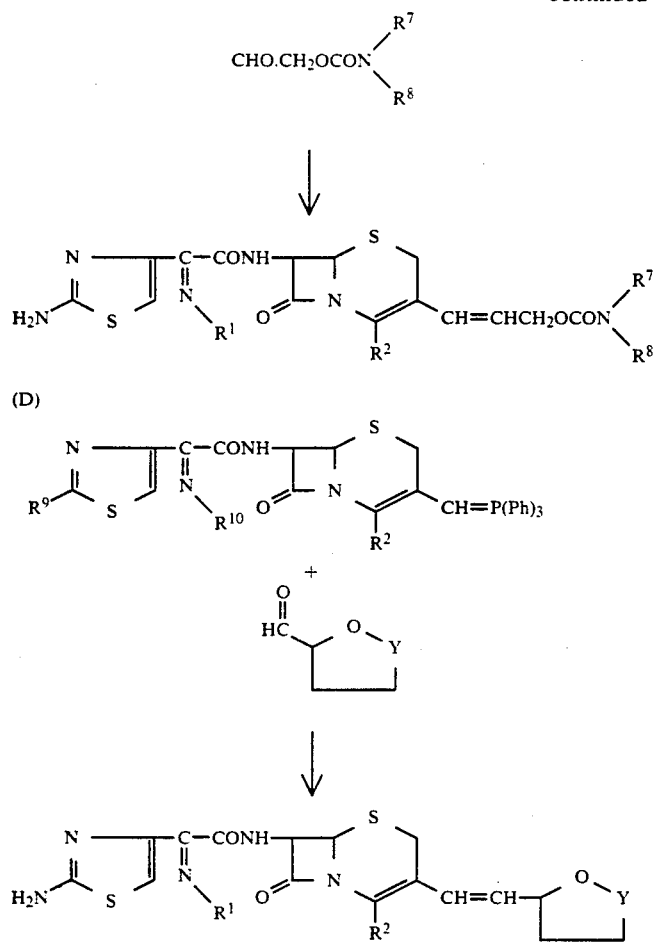

(D)

In all the above reaction schemes (A)-(D), $R^1$, $R^2$, $R^3$, $R^4$, $R^5$, $R^6$, $R^7$, $R^8$, $R^9$, $R^{10}$ and Y have the same meanings as defined above.

Production Process 3

In the case where X represents a nitrogen atom in formula (I), the target compounds of the present invention can also be prepared in a similar manner to Production Process 2 described above.

Namely, the target compounds of the present invention represented by the formula (XI) can be prepared by substituting the moiety of the formula

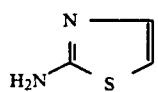

for the moiety of the formula

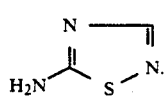

The following specific reaction scheme can be described by way of example:

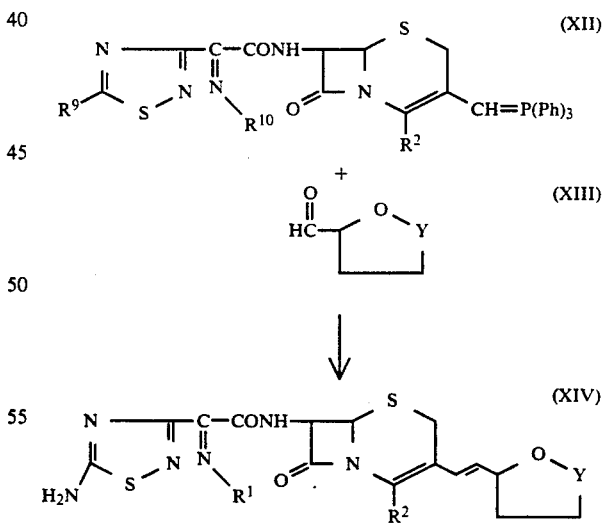

wherein $R^1$, $R^2$, $R^9$, $R^{10}$ and Y have the same meanings as defined above.

Where $R^2$ is a carboxyl group in all the compounds embraced in the present invention (for example, in the target compounds obtained in the final steps of Preparation Processes 1-3 described above in detail), the target compounds can be converted into compounds in which $R^2$ is a protected carboxyl group or into their salts by introducing a carboxyl-blocking protective group into the target compounds obtained finally or their salts by a method known Per se in the art. The above conversion can be easily conducted, for example, by usual esterification. Needless to say, the thus-converted compounds and their salts also fall within the scope of the present invention.

The compounds of the present invention which have been obtained by such processes as described above have excellent antibacterial activities and are useful especially as orally-administrable antibacterial agents.

The compounds of the present invention all have an acute toxicity value [LD$_{50}$(mouse, oral administration)] of 2 g/kg or greater.

Upon use of the compounds of the present invention as antibacterial agents, the dosage varies depending on the conditions, the age, sex, weight and sensitivity of the patient, the route, time and intervals of the administration, the properties of the preparations, the kinds of effective ingredients, etc. The compound of the present invention can be administered, but are not limited to, in a dosage of 100 mg to 5 g orally or peritoneally in 1-4 portions a day.

For the preparation of solid preparations for oral administration, a principal ingredient is added with an excipient and optionally, a binder, disintegrator, lubricant, coloring agent, corrigent, etc. and then formed into tablets, coated tablets, granules, powders, capsules by a method known per se in the art.

Exemplary excipients include lactose, corn starch, sucrose, glucose, sorbit, crystalline cellulose and silicon dioxide. Exemplary binders include polyvinyl alcohol, polyvinyl ether, ethylcellulose, methylcellulose, gum arabic, tragacanth, gelatin, shellac, hydroxypropylcellulose, hydroxypropylmethylcellulose, calcium citrate, dextrin and pectin. Illustrative lubricants include magnesium stearate, talc, polyethylene glycol, silica and hydrogenated vegetable oil. As colorants, those authorized for use in pharmaceuticals can be used. Exemplary corrigents include cocoa powder, menthol, aromatic acids, peppermint oil, refined Borneo camphor and cinnamon powder. These tablets and granules may, of course, be coated with tablets and granules may, of course, be coated with sugar, gelatin or the like as needed.

For the preparation of injections, a principal ingredient is added optionally with a pH adjuster, buffer, suspending agent, solubilizing agent, stabilizer, isotonicity, preservative and the like and formed into an intravenous injection, subcutaneous injection or intramuscular injection by a method known per se in the art. Here, the injection can optionally be lyophilized by a usual technique.

Certain examples will next be given to describe the present invention in further detail. Needless to say, the present invention is not necessarily limited to them.

Synthesis examples of compounds useful as raw materials for certain target compounds of the present invention will be described as preparation examples prior to the examples. Abbreviation "Trt" in the following chemical structural formulas stands for a trityl group.

PREPARATION EXAMPLE 1

4-Methoxyphenylmethyl 7-[(Z)-2-(2-tritylaminothiazol-4-yl)-2-trityloxyiminoacetamido]-3-[(Z)-3-tert-butyldimethylsilyloxy-1-propenyl]-3-cephem-4-carboxylate

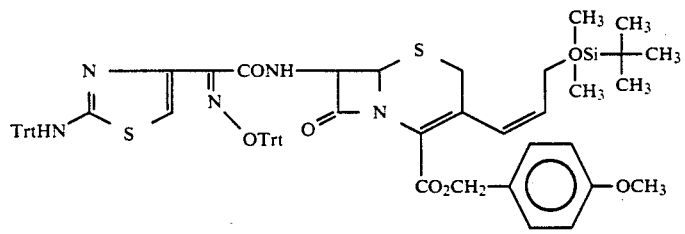

A solution of 4-methoxyphenylmethyl 7-[(Z)-2-(2-trityIaminothiazol-4-yl)-2-trityloxyiminoacetamido]-3-(triphenylphosphoranylidene)methyl-3-cephem-4-carboxylate (9.07 g; 7.27 mmol) and t-butyldimethylsilyloxyacetaldehyde (1.8 g; 10.34 mmol) in dichloromethane (100 ml) was stirred at room temperature for 16 hours. After the solvent was distilled off under reduced pressure, the residue was purified by chromatography on a silica gel column (n-hexane:ethyl acetate=2.5:1) whereby the title compound (4.99 g; 4.36 mmol; 60% was obtained.

NMR (CDCl$_3$) δ: 0.20(6 H,bs,CH$_3$x2), 1.04(9 H,bs,C(CH$_3$)$_3$), 3.40–3.60(2 H,m,CH$_2$), 3.88(3 H,s,OCH$_3$), 4.20–4.40(2 H,m,—CH$_2$OSi), 5.00–5.20(1 H,m,CH), 5.28(2 H,s,CO$_2$CH$_2$), 5.60–6.40(3 H,m,CH,—CH=CH—), 6.56(1 H,thiazole-H), 6.90–7.80(34 H,m,Ph-Hx34).

PREPARATION EXAMPLE 2

4-Methoxyphenylmethyl 7-[(Z)-2-(2-tritylaminothiazol-4-yl)-2-trityloxyiminoacetamido]-3-[(Z)-3-hydroxy-1-propenyl]-3-cephem-4-carboxylate

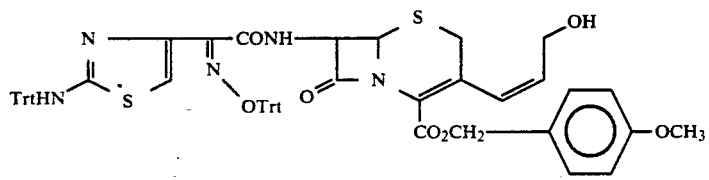

1N-Hydrochloric acid (10 ml) was added to a solution of the compound (4.99 g; .4.36 mmol), which had been obtained in Preparation Example 1, in acetone (50 ml), followed by stirring at room temperature for 2 hours. After the acetone was distilled off under reduced pressure, water was added, followed by extraction with ethyl acetate. The extract was washed with water and then with saturated saline. Magnesium sulfate was added to dry the extract. The solvent was distilled off under reduced pressure and the residue was purified by chromatography on a silica gel column, whereby the title compound (2.2 g; 2.14 mmol; 49.0%) was obtained.

NMR (CDCl$_3$) δ: 3.24(2 H,ABq,J=18.0 Hz,CH$_2$), 3.80(3 H,s,OCH$_3$), 3.90–4.10(2 H,m,—CH$_2$O—), 5.02(1 H,d,J=4.8 Hz,CH), 5.16(2 H,s,CO$_2$CH$_2$—), 5.60–6.00(2 H,m,CH,=CH—), 6.14(1 H,d,J=12.5 Hz,—CH=), 6.42(1 H,s,thiazole-H), 6.80–7.70(34 H,pH-Hx34).

Mass (m/Z): 1029(M+). 1030(M++1).

PREPARATION EXAMPLE 3

4-Methoxyphenylmethyl 7-[(Z)-2-(2-tritylaminothiazol-4-yl)-2-trityloxyiminoacetamido]-3-[(Z)-3-carbamoyloxy-1-propenyl]-3-cephem-4-carboxylate

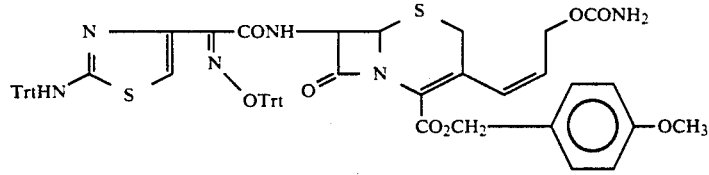

Under a nitrogen gas stream, a solution of the compound (386 mg; 0.375 mmol), which had been obtained in Preparation Example 2, in dry tetrahydrofuran (15 ml) was cooled to −50° C., to which chlorosulfonyl isocyanate (0.08 ml; 0.919 mmol) was added dropwise. After the resulting mixture was stirred at −20° C. for 1 hour, the mixture was added with a buffer (15 ml) of pH 7 and ethyl acetate and was gradually heated to room temperature. The mixture was stirred for 20 minutes. The ethyl acetate layer was washed with water and then with saturated saline. Magnesium sulfate was added to dry the solution. The solvent was concentrated under reduced pressure, followed by the dropwise addition of the ethyl acetate solution to n-hexane (80 ml). Crystals thus precipitated were collected by filtration and dried, whereby the title compound (400 mg; 0.372 mmol; 99.4%) was obtained.

NMR (CDCl$_3$) δ: 3.26(2 H,ABq,J=18.0 Hz,CH$_2$), 3.78(3 H,s,OCH$_3$), 4.25–4.50(2 H,m,CH$_2$), 4.80(2 H,brs,OCONH$_2$), 5.00(1 H,d,J=4.8 Hz,CH), 5.16(2 H,s,—CO$_2$CH$_2$—), 5.50–5.70(1 H,m,=CH—), 5.96(1 H,dd,J=8.4,4.8 Hz,CH), 6.24(1 H,d,J=12.5 Hz,—CH=), 6.46(1 H,s,thiazole-H), 6.80–7.70(34 H,m,PhHx34).

Mass (m/Z): 1072(M+), 1073(M++1).

PREPARATION EXAMPLE 4

4-Methoxyphenylmethyl 7-[(Z)-2-(2-tritylaminothiazol-4-yl)-2-methoxyiminoacetamido]-3-[(Z)-3-tert-butyldimethylsilyloxy-1-propenyl]-3-cephem-4-carboxylate

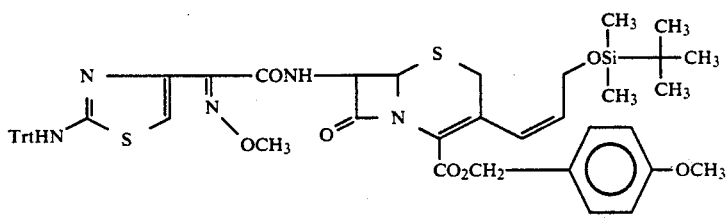

A solution of 4-methoxyphenylmethyl 7-[(Z)-2-(2-tritylaminothiazol-4-yl)-2-methoxyiminoacetamido]-3-(triphenylphosphoranylidene)methyl- 3-cephem-4-carboxylate (10.5 g; 10.30 mmol) and t-butyldimethylsilyloxyacetaldehyde (2.58 g; 14.83 mmol) in dichloromethane (100 ml) was stirred at room temperature for 16 hours. After the solvent was distilled off under reduced pressure, the residue was purified by chromatography on a silica gel column (n-hexane:ethyl acetate=2.5:1) whereby the title compound (4.30 g; 4.72 mmol; 45.8%) was obtained.

NMR (CDCl$_3$) δ: 0.20(6 H,brs,CH$_3$x2), 1.04(9 H,brs,C(CH$_3$)$_3$), 3.55–3.80(2 H,m,CH$_2$), 3.92(3 H,s,OCH$_3$), 4.10(3 H,s,OCH$_3$), 4.10–4.30(2 H,m,—CH$_2$OSi), 5.10–5.30(3 H,m,CH,CO$_2$CH$_2$), 5.70–6.40(3 H,m,CH,—CH=CH—), 6.60–7.60(20 H,m,thiazole-H,Ph-Hx19).

PREPARATION EXAMPLE 5

4-Methoxyphenylmethyl 7-[(Z)-2-(2-tritylaminothiazol-4-yl)-2-methoxyiminoacetamido]-3-[(Z)-3-hydroxy-1-propenyl]-3-cephem-4-carboxylate

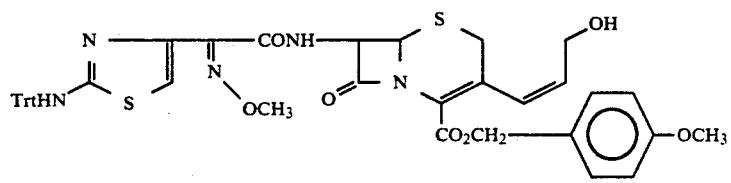

1N-Hydrochloric acid (10 ml) was added to a solution of the compound (4.30 g; 4.72 mmol), which had been obtained in Preparation Example 4, in acetone (50 ml), followed by stirring at room temperature for 2 hours. After the acetone was distilled off under reduced pressure, water was added, followed by extraction with ethyl acetate. The extract was washed with water and then with saturated saline. Magnesium sulfate was added to dry the extract. The solvent was distilled off under reduced pressure and the residue was purified by chromatography on a silica gel column, whereby the title compound (2.1 g; 2.62 mmol; 55.0%) was obtained.

NMR (CDCl$_3$) δ: 4(2 H,ABq,J=18.0 Hz,CH$_2$), 3.72(3 H,s,OCH$_3$), 4.00(3 H,s,OCH$_3$), 3.85–4.15(2 H,m,—CH$_2$O—), 5.00(1 H,d,J=5.1 Hz,CH), 5.08(2 H,s,CO$_2$CH$_2$), 5.55–5.95(2 H,m,CH,=CH—), 6.10(1 H,d,J=11.5 Hz,—CH=), 6.56(1 H,s,thiazole-H), 6.70–7.40(19 H,m,Ph-Hx19).

PREPARATION EXAMPLE 6

4-Methoxyphenylmethyl 7-[(Z)-2-(2-tritylaminothiazol-4-yl)-2-methoxyiminoacetamido]-3-[(Z)-3-carbamoyloxy-1-propenyl]-3-cephem-4-carboxylate

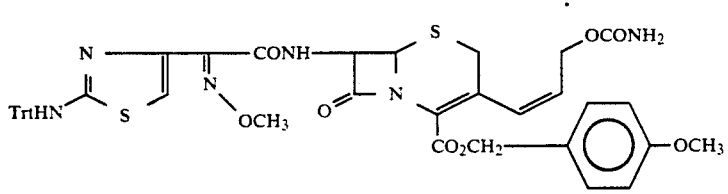

Under a nitrogen gas stream, a solution of the compound (2.1 g; 2.619 mmol), which had been obtained in Preparation Example 5, in dry tetrahydrofuran (30 ml) was cooled to −50° C., to which chlorosulfonyl isocyanate (1 ml; 11.49 mmol) was added dropwise. After the resulting mixture was stirred at −20° C. for 1 hour, the mixture was added with a buffer (30·ml) of pH 7 and ethyl acetate and was gradually heated to room temperature. The mixture was stirred for 20 minutes. The ethyl acetate layer was washed with water and then with saturated saline. Magnesium sulfate was added to dry the solution. The solvent was concentrated under reduced pressure, followed by the dropwise addition of the ethyl acetate solution to n-hexane (200 ml). Crystals thus precipitated were collected by filtration and dried, whereby the title compound (1.4 g; 1.657 mol; 63.3%) was obtained.

NMR (CDCl$_3$) δ: 3.24(2 H,ABq,J=18.0 Hz,CH$_2$), 3.72(3 H,s,OCH$_3$), 3.98(3 H,s,OCH$_3$), 4.30–4.60(2 H,m,CH$_2$), 4.84(2 H,brs,OCONH$_2$), 5.00(1 H,d,J=5.1 Hz,CH), 5.08(2 H,s,CO$_2$CH$_2$—), 5.50–5.95(2 H,m,CH,=CH—), 6.17(1 H,d,J=11.5 Hz,—CH=), 6.54(1 H,s,thiazole-H), 6.70–7.40(19 H,m,Ph-Hx19).

PREPARATION EXAMPLE 7

4-Methoxyphenylmethyl 7-[(Z)-2-(2-tritylaminothiazol-4-yl)-2-trityloxyiminoacetamido]-3-](Z)-3-(N-methylcarbamoyloxy)-1-propenyl]-3-cephem-4-carboxylate

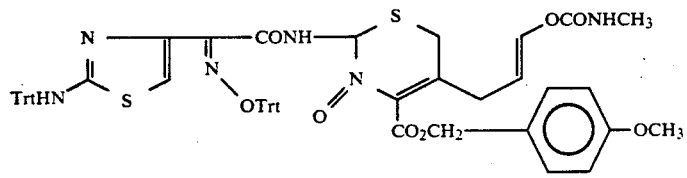

To a solution of the compound (2 g; 1.944 mmol), which had been obtained in Preparation Example 2, in dry tetrahydrofuran (40 ml), methyl isocyanate (887 mg; 15.548 mmol) and triethylamine (catalytic amount) were added. The resulting mixture was heated at 60° C. for 4 hours. The solvent was distilled off under reduced pressure and the residue was purified by chromatography on a silica gel column (dichloromethane:acetone=95:5), whereby the title compound (1 g; 0.920 mmol; 47.3%) was obtained.

NMR (CDCl$_3$) δ: 2.66(3 H,d,J=4.4 Hz,NH—CH$_3$), 3.25(2 H,ABq,J=18.0 Hz,CH$_2$), 3.74(3 H,s,OCH$_3$), 4.30–4.70(2 H,m,CH$_2$), 5.02(1 H,d,J=4.8 Hz,CH), 5.10(2 H,s,CO$_2$CH$_2$), 5.55–5.80(1 H,m,=CH—), 5.96(1 H,dd,J=8.1,4.8 Hz,CH), 6.18(1 H,d,J=11.8 HZ,—CH=), 6.40(1 H,s,thiazole-H), 6.80–7.60(34 H,m,ph-Hx34).

PREPARATION EXAMPLE 8

Paramethoxybenzyl 7-Formamido-3-(3-2 H-tetrazolyl-1-propen-1-yl)-3-cephem-4-carboxylate (E-isomer) (A)

Paramethoxybenzyl 7-Formamido-3-(3-1 H-tetrazolyl-1-propen-1-yl)-3-cephem-4-carboxylate (E-isomer) (B)

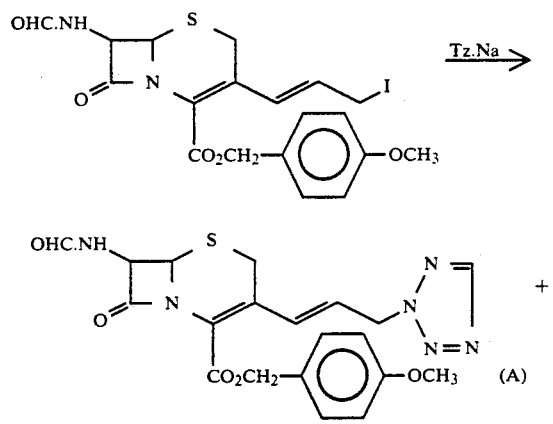

-continued

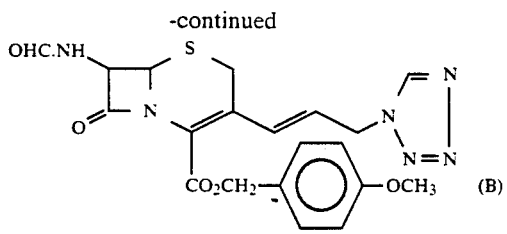

PREPARATION EXAMPLE 9

Paramethoxybenzyl 7-[2-(2-Tritylaminothiazol-4-yl)-2-tritylaminoacetamido]-3-(3-1H-tetrazolyl-1-propen-1-yl)-3-cephem-4-carboxylate (E-isomer)

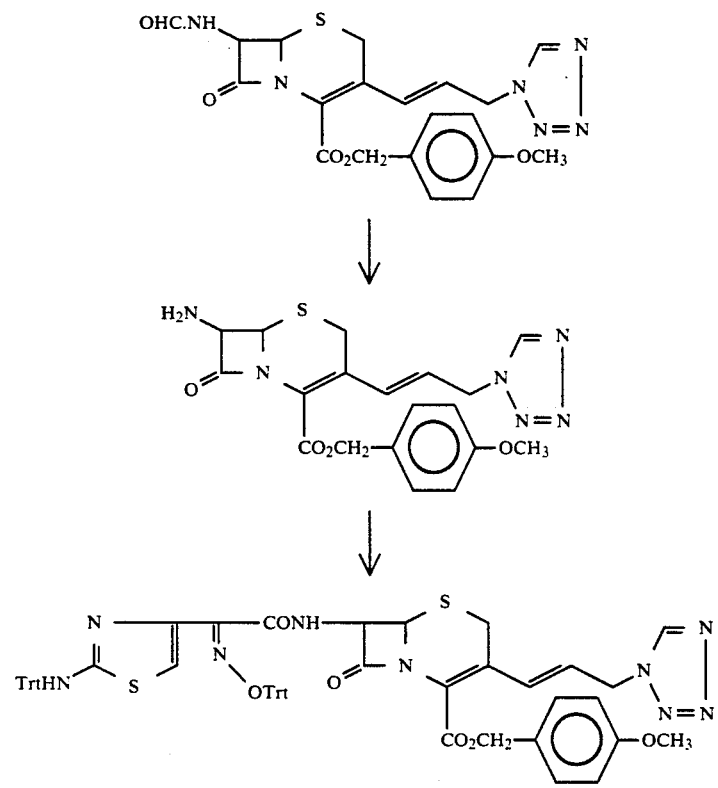

Paramethoxybenzyl 7-formamido-3-[(E)-3-iodo-1-propen-1-yl]-3-cephem-4-carboxylate (19.2 g) was dissolved in dimethylformamide (96 ml), followed by the addition of the sodium salt of 1 H-tetrazole (Tz.Na) (3.2 g) under ice cooling. After the resulting mixture was stirred for 30 minutes at the same temperature, the reaction mixture was added to a chilled mixed solvent of 1N hydrochloric acid and ethyl acetate and the organic layer was separated. After the organic layer was washed with water and then with saturated saline, it was dried with magnesium sulfate. The solution was concentrated under reduced pressure and subjected to column chromatography, whereby the two types of title compounds (A) and (B) were obtained (6.2 g and 3.6 g) [the compound having a smaller Rf value upon thin layer chromatography being identified by (A) and that having a larger Rf value by (B)].

NMR (CDCl$_3$) δ:

(A): 3.75(3 H,s), 4.90(1 H,d,J=5 Hz), 5.14(2 H,s), 5.65–6.15(2 H,m), 6.70–7.30(m), 8.15(1 H,s), 8.58(1 H,s);

(B): 3.76(3 H,s), 4.93(1 H,d,J=5 Hz), 5.16(2 H,s), 5.60–6.20(2 H,m), 6.50–7.40(m), 8.15(1 H,s), 8.42(1 H,s).

After the compound (B) (1 g) obtained in Preparation Example 8 was dissolved in a methanol-tetrahydrofuran (%) solution (20 ml), concentrated hydrochloric acid (1 ml) was added, followed by stirring at room temperature for 7 hours. The solvent was distilled off, followed by the addition of ethyl acetate and a 5% aqueous solution of sodium hydrogencarbonate. The organic layer was washed with saturated saline and then dried over sodium sulfate. By distillation under reduced pressure, 7-amino derivative (940 mg) was obtained. This compound was then dissolved in dimethylformamide (28 ml), followed by the addition of 2-(2-tritylaminothiazol-4-yl)-2-trityliminooxyacetic acid (1.33 g), 1-hydroxybenzotriazole (325 mg) and dicyclohexylcarbodiimide(459 mg). The resulting mixture was stirred at room temperature for 12 hours. After the reaction, precipitated dicyclohexylurea was filtered off and the residue was added to a mixed solvent of ethyl acetate and water. The organic layer was collected, washed with saturated saline, and then dried over magnesium sulfate. After the solvent was distilled off, the residue was subjected to column chromatography whereby the title compound (1.61 g) was obtained.

NMR (CDCl$_3$) δ: 3.23(2 H,brs), 3.70(3 H,s), 4.86(1 H,d,J=5 Hz), 5.0–5.25(4 H,m), 5.65–6.05(2 H,m), 6.36(1 H,s), 6.60–7.60(m), 8.30(1 H,s).

PREPARATION EXAMPLE 10
Paramethoxybenzyl 7-[2-(2-Tritylaminothiazol-4-yl)-2-tritylaminoacetamido]-3-(3-2H-tetrazolyl-1-propen-1-yl)-3-cephem-4-carboxylate (E-isomer)
In a similar manner to Preparation Example 9, the title compound was obtained from the compound (A) obtained in Preparation Example 8.
NMR (CDCl₃) δ: 3.25(2 H,brs), 3.72(3 H,s), 4.70–5.00(3H,m), 5.15(2H,s), 5.15–6.10(2 H,m), 6.36(1 H,s), 6.50–7.60(m), 8.42(1 H,s).
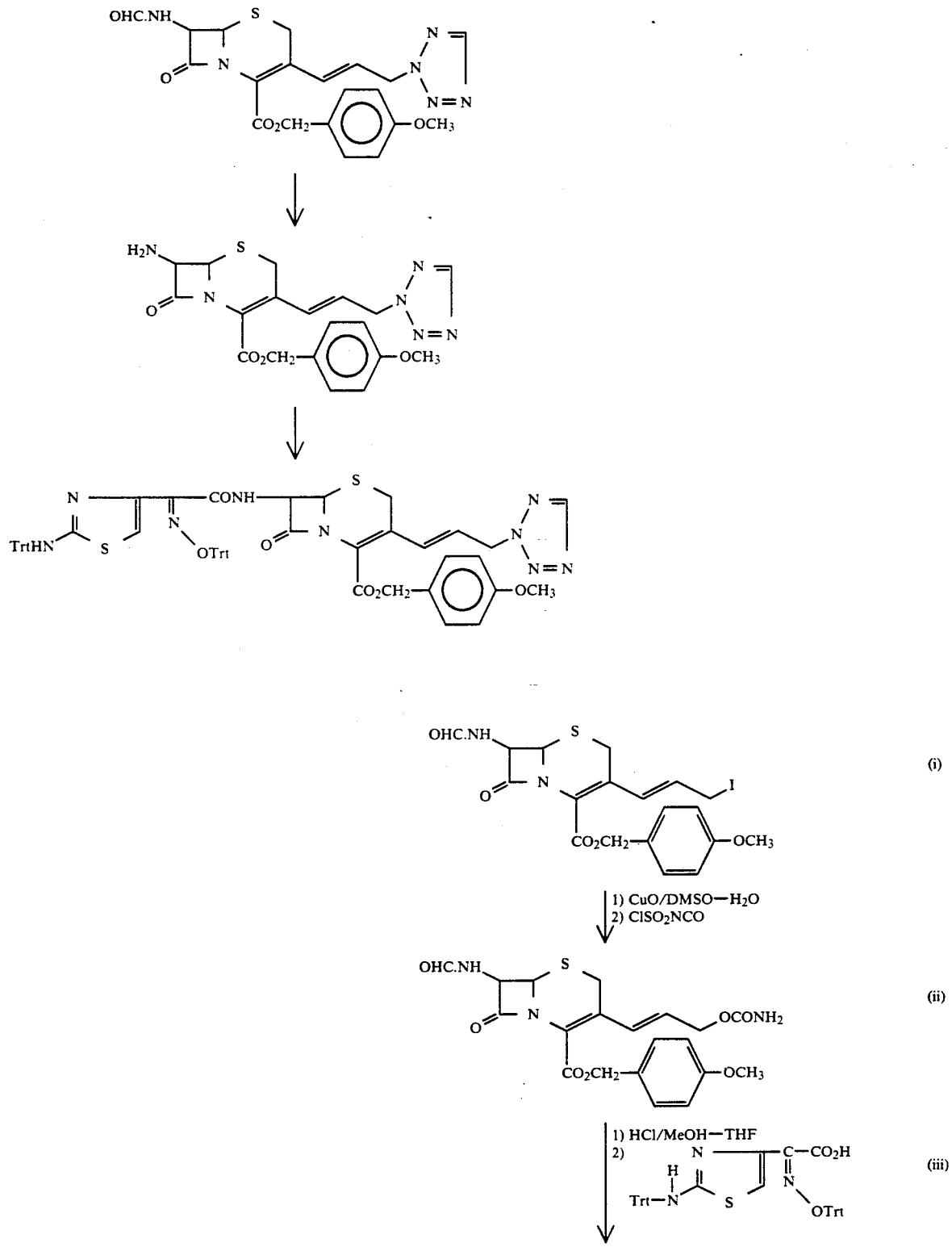

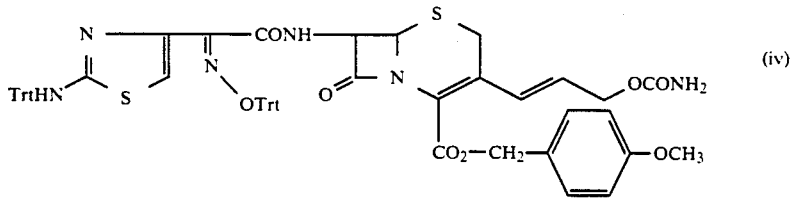

(1) The compound (69 g) represented by the formula (i) were dissolved in a mixture of dimethyl sulfoxide (DMSO) (690 ml) and water (210 ml), followed by the addition of cuprous oxide (17.9 g). The resulting mixture was heated to 50° C. After 30 minutes, the mixture was ice-cooled and insoluble matter was filtered off. The resulting filtrate was added with ethyl acetate and was then subjected to phase separation. The ethyl acetate solution was washed with water and then dried over sodium sulfate. The solvent was distilled off under reduced pressure. The residue was crystallized from a mixed solvent of ethyl ether and ethyl acetate, whereby crude crystals (7.4 g) were obtained. Those crystals were dried without purification and then provided for use in the following step.

(2) After the crystals obtained in the preceding step were dissolved in tetrahydrofuran (THF) (185 ml), chlorosulfonyl isocyanate (3.5 ml) was added at a temperature of −50° C. to −60° C. One hour later, the reaction mixture was added to a phosphate buffer solution (300 ml) under ice-cooling. After the mixed solution was heated back to room temperature, the solution was added with ethyl acetate and then subjected to phase separation. The resulting organic layer was washed with saturated saline and then dried over magnesium sulfate ($MgSO_4$). After the solvent was distilled off under reduced pressure, the residue was subjected to column chromatography, whereby the compound (ii) (530 mg) was obtained.

After the compound (ii) (530 mg) thus obtained was suspended in a 1:1 mixture of THF and MeOH, (30 ml), concentrated hydrochloric acid (0.53 ml) was added. After the resultant mixture was stirred at room temperature for 1.5 hours, concentrated hydrochloric acid (0.53 ml) was added further and the resulting mixture was stirred for 4 hours. The solvent was distilled off under reduced pressure, followed by the addition of a mixture of ethyl acetate and 5% aqueous sodium hydrogencarbonate solution (EtOAC-5% aq.$NaHCO_3$). The mixture was subjected to phase separation. The resulting organic layer was washed with saturated saline, followed by drying over sodium sulfate ($Na_2SO_4$). The solvent was distilled off under reduced pressure, whereby the title compound (500 mg) was obtained.

NMR (DMSO-$d_6$) δ:
3.75(3 H,s), 4.48(2 H,d,J=6 Hz), 5.15(1 H,d,J=5 Hz), 5.17(2 H,s), 5.76(1 H,dd,J=8 Hz,5 Hz), 6.0–6.3(1 H,m),
6.51(2 H,brs), 6.73(1 H,d,J=16 Hz), 6.90(2 H,d,J=9 Hz),
7.33(2 H,d,J=9 Hz), 8.10(1 H,s), 9.05(1 H,d,J=8 Hz).

(3) After the compound (500 mg) obtained in the step (2), (Z)-2-(2-trithylaminothiazole)-2-trithyloxyiminoacetic acid (706 mg) and hydroxybenzotriazole (HOBT)-$H_2O$ (173 mg) were dissolved in dimethylformamide (DMF) (10 ml), the resulting mixture was added with N,N′-dicyclohexylcarbodiimide (DDC) (24.4 mg) and stirred for 4 hours. After the resulting urea was filtered off, the filtrate was poured into a mixture of ethyl acetate and water. The resulting solution was subjected to phase separation. The resulting organic layer was washed with $H_2O$ and then with saturated saline, followed by drying over $MgSO_4$. After the solvent was removed under reduced pressure, the residue was subjected to column chromatography, whereby the compound (iii) (620 mg) was obtained.

NMR ($CDCl_3$) δ: 3.26(2 H,brs), 3.73(3 H,s), 4.43(2 H,d,J=6 Hz), 4.80(2 H,brs), 4.90(1 H,d,J=5 Hz), 5.16(2 H,s), 5.6–6.0(2 H,m), 6.40(1 H,s), 6.70–7.5(m).

EXAMPLE 1

Sodium 7-[(Z)-2-(2-aminothiazol-4-yl)-2-hydroxyiminoacetamido]-3-[(Z)-3-carbamoyloxy-1-propenyl]-3-cephem-4-carboxylate

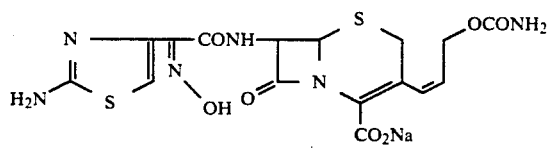

To a solution of the compound (1.14 g; 1.062 mmol), which had been obtained in Preparation Example 3, in anisole (8 ml), trifluoroacetic acid (10 ml) was added dropwise under ice cooling. The resulting mixture was stirred at room temperature for 2 hours. The trifluoroacetic acid was distilled off under reduced pressure and the residue was added dropwise to a mixed solvent of isopropyl ether (20 ml) and n-hexane (80 ml). Precipitated crystals were collected by filtration. The crystals were added to 90% formic acid (10 ml), followed by stirring at room temperature for 3 hours. Under reduced pressure, the solvent was distilled off. The residue was trituated in isopropyl ether and crystals were collected by filtration. Those crystals were dissolved in methanol (10 ml), followed by the addition of sodium acetate (262 mg; 3.194 mmol). Under reduced pressure, the solvent was distilled off. The crude product was trituated in 2-propanol and crude crystals were collected by filtration. The crude crystals were purified by chromatography on a silica gel column (5% aqueous methanol). Eluate was concentrated under reduced pressure and then lyophilized, whereby the title compound (208 mg; 0.424 mmol; 39.9%) was obtained.

NMR (DMSO-$d_6$) δ: 3.77(2 H,ABq,J=16.3 Hz,$CH_2$), 4.50–4.70(2 H,dm,$CH_2$), 5.04(1 H,d,J=4.8 Hz,CH), 5.20–5.30(1 H,m,=CH—), 5.59(1 H,dd,J=8.4,4.8 Hz,CH), 6.45(2 H,brs,$OCONH_2$), 6.64(1 H,d,J=12.5 Hz,—CH=), 6.66(1 H,s,thiazole-H), 7.09(2 H,s,—$NH_2$), 9.40(1 H,brs,—CONH—), 11.00(1 H, brs,=N—OH).

Mass (m/Z): 490($M^+$), 491($M^+$ +1).

EXAMPLE 2

Pivaloyloxymethyl 7-[(Z)-2-(2-aminothiazol-4-yl)-2-hydroxyiminoacetamido]-3-(Z)-3-carbamoyloxy-1-propenyl]-3-cephem-4-carboxylate

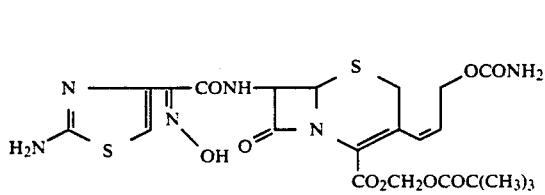

To a solution of the compound (167 mg; 0.341 mmol), which had been obtained in Example 1 in dry dimethylformamide (3 ml), a solution of iodomethyl pivalate (83 mg; 0.343 mmol) in dry dimethylformamide (0.5 ml) was added dropwise under ice cooling. The resulting mixture was stirred for 30 minutes. Ethyl acetate was added to the reaction mixture. The resulting mixture was washed with water and then with saturated saline. Magnesium sulfate was added to dry the mixture, followed by distillation under reduced pressure. The residue was purified by chromatography on a silica gel column (ethyl acetate:methanol=48:2). Eluate was concentrated under reduced pressure and then added dropwise to n-hexane (40 ml). Precipitated crystals were collected by filtration and then dried, whereby the title compound (56 mg; 0.096 mmol; 28.2%) was obtained.

NMR (DMSO-$d_6$) $\delta$: 1.16(9 H,s,C(CH$_3$)3), 3.60(2 H,ABq,J=18.0 Hz,CH$_2$), 4.30–4.50(2 H,dm,CH$_2$), 5.24(1 H,d,J=5.1 Hz,CH), 5.60–5.70(1 H,m,=CH—), 5.75–5.85(3 H,m,CH,CO$_2$CH$_2$O), 6.27(1 H,d,J=11.7 Hz,—CH=), 6.52(2 H,brs,OCONH$_2$), 6.66(1 H,s,thiazole-H), 7.10(2 H,s,NH$_2$), 9.47(1 H,d,J=8.1 Hz,CONH), 11.28(1 H,s,=N—OH).

Mass (m/Z): 582(M$^+$), 583(M$^+$+1).

Further, 7N hydrochloric acid/diethyl ether solution (0.04 ml) was added dropwise under ice cooling to a solution of the title compound (47 mg; 0.079 mmol) in dichloromethane (1 ml), followed by stirred for 20 minutes. Precipitated crystals were collected by filtration and then dried, whereby the hydrochloride (42 mg; 0.066 mmol; 84%) of the title compound was obtained.

EXAMPLE 3

2-Ethylbutanoyloxymethyl 7-(Z)-2-(2-aminothiazol-4-yl)-2-hydroxyiminoacetamido]-3-[(Z)-3-carbamoyloxy-1-propenyl]-3-cephem-4-carboxylate

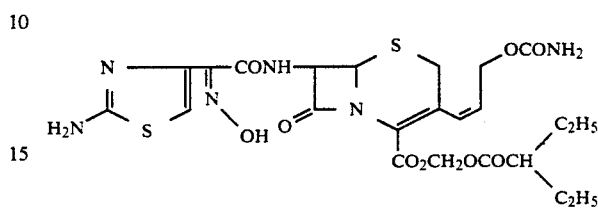

To a solution of the compound (220 mg; 0.449 mmol), which had been obtained in Example 1 in dry dimethylformamide (4 ml), a solution of iodomethyl 2-ethylbutyrate (95%; 121 mg; 0.449 mmol) in dry dimethylformamide (1 ml) was added dropwise under ice cooling. The resulting mixture was stirred for 40 minutes. Ethyl acetate was added to the reaction mixture. The resulting mixture was washed with water and then with saturated saline. Magnesium sulfate was added to dry the mixture, followed by the distillation of the solvent under reduced pressure. The residue was purified by chromatography on a silica gel column (ethyl acetate:methanol=48:2). Eluate was concentrated and then added dropwise to n-hexamne (50 ml). Precipitated crystals were collected by filtration and then dried, whereby the title compound (110 mg; 0.184 mmol; 41.1%) was obtained.

NMR (DMSO-$d_6$) $\delta$: 0.80–0.90(6 H,m,CH$_2$CH$_2$x2), 1.45–1.60(4 H,m,CH$_2$CH$_3$x2), 2.20–2.30(1H,m,C$\underline{H}$$\diagdown^{C_2H_5}_{C_2H_5}$), 3.61(2 H,ABq,J=17.8 Hz,CH$_2$), 4.35–4.50(2 H,dm,CH$_2$), 5.25(1 H,d,J=4.8 Hz,CH), 5.60–5.70(1 H,m,=CH—), 5.75–5.85(3 H,m,CO$_2$CH$_2$O,CH), 6.28(1 H,d,J=11.7 Hz,—CH=), 6.52(2 H,brs,OCONH$_2$), 6.66(1 H,s,thiazole-H), 7.10(2 H,s,NH$_2$), 9.47(1 H,d,J=8.4 Hz,CONH), 11.28(1 H,brs,=N—OH).

Mass (m/Z: 596(M$^+$), 597(M$^+$+1).

Further, 7N hydrochloric acid/diethyl ether solution (0.02 ml) was added dropwise under ice cooling to a solution of the title compound (44 mg; 0.074 mmol) in ethyl acetate (2 ml), followed by stirring for 20 minutes. Precipitated crystals were collected by filtration and then dried, whereby the hydrochloride (40 mg; 0.063 mmol; 85.4%) of the title compound was obtained.

EXAMPLE 4

1-(Cyclohexylacetyloxy)ethyl 7-[(Z)-2-(2-aminothiazol-4-yl)-2-hydroxyiminoacetamido]-3-[(Z)-3-carbamoyloxy-1-propenyl]-3-cephem-4-carboxylate

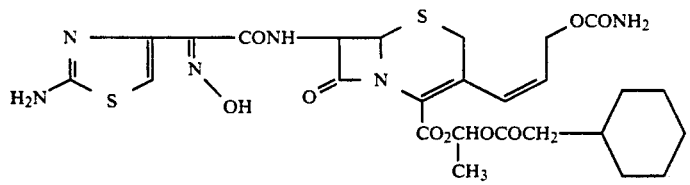

To a solution of the compound (140 mg; 0.285 mmol), which had been obtained in Example 1 in dry dimethylformamide (3 ml), a solution of 1-iodoethyl cyclohexylacetate (85 mg; 0.287 mmol) in dry dimethylformamide (1 ml) was added dropwise under ice cooling. The resulting mixture was stirred for 40 minutes. Ethyl acetate was added to the reaction mixture. The resulting mixture was washed with water and then with saturated saline. Magnesium sulfate was added to dry the mixture, followed by the concentration of the solvent under reduced pressure. The concentrate was added dropwise to n-hexane (50 ml). Precipitated crystals were collected by filtration and then dried, whereby the title compound (30 mg; 0.047 mmol; 16.5%) was obtained.

NMR (DMSO-$d_6$) δ: 0.85–1.00(2 H,m,$CH_2$), 1.05–1.25(3 H,m,$CH_2$CH), 1.43 and 1.44(3 H,d,J=5.5 Hz,$CO_2$CHCH$_3$O), 1.55–1.70( 6 H,m,$CH_2$x3), 2.21(2 H,d,J=6.6 Hz,OCOCH$_2$—), 3.58 and 3.60(2 H,ABq,J=18.0 Hz,$CH_2$), 4.30–4.50(2 H,m,$CH_2$O—), 5.23 and 5.24(1 H,d,J=4.8 Hz,CH), 5.55–5.70(1 H,m,=CH—), 5.80–5.90(1 H,m,CH), 6.22 and 6.26(1 H,d,J=11.7 Hz,—CH=), 6.51(2 H,brs,OCONH$_2$), 6.65(1 H,s,thiazole-H), 6.84 and 6.91(1 H,q,J=5.5 Hz,OCHCH$_3$O—), 7.12(2 H,brs,NH$_2$), 9.46 and 9.47(1 H;d,J=8.1 Hz,CONH), 11.31(1 H,s,=N—OH).

Mass (m/Z): 636(M$^+$), 637(M$^+$+1).

Further, 7N hydrochloric acid/diethyl ether solution (0.02 ml) was added dropwise under ice cooling to a solution of the title compound (30 mg 0.047 mmol) in ethyl acetate (2 ml), followed by stirring for 20 minutes. Precipitated crystals were collected by filtration and then dried, whereby the hydrochloride (28 mg; 0.042 mmol; 88.5%) of the title compound was obtained.

EXAMPLE 5

1-(3-Methylpentanoyloxy)ethyl 7-[(Z)-2-(2-aminothiazol-4-yl)-2-hydroxyiminoacetamido]3-[(Z)-3-carbamoyloxy-1-propenyl]-3-cephem-4-carboxylate

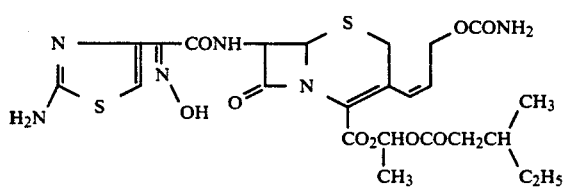

To a solution of the compound (200 mg; 0.408 mmol), which had been obtained in Example 1 in dry dimethylformamide (3 ml), a solution of 1-iodoethyl 3-methylvalerate (110 mg; 0.407 mmol) in dry dimethylformamide (1 ml) was added dropwise under ice cooling. The resulting mixture was stirred for 40 minutes. Ethyl acetate was added to the reaction mixture. The resulting mixture was washed with water and then with saturated saline. Magnesium sulfate was added to dry the mixture, followed by the concentration of the solvent under reduced pressure. The concentrate was added dropwise to n-hexane (50 ml). Precipitated crystals were collected by filtration and then dried, whereby the title compound (52 mg; 0.085 mmol; 20.9%) was obtained.

NMR (DMSO-$d_6$) δ: 0.80–0.90(6 H,m,$CH_3$x2), 1.10–1.25 and 1.25–1.40(2 H,m,$CH_2$), 1.70–1.80(1 H,m,CH), 1.43 and 1.45(3 H,d,J=5.5 Hz,CH—CH$_3$), 2.05–2.15 and 2.25–2.35(2 H,m,COCH$_2$), 3.59 and 3.60(2 H,ABq,J=18.0 Hz,$CH_2$), 4.35–4.50(2 H,m,$CH_2$), 5.23 and 5.25(1 H,d,J=4.9 Hz,CH), 5.55–5.70(1 H,m,=CH—), 5.80–5.90(1 H,m,CH), 6.23 and 6.26(1 H,d,J=12.8 Hz,—CH=), 6.51(2 H,brs,OCONH$_2$), 6.66(1 H,s,thiazole-H), 6.86 and 6.92(1 H,q,J=5.5 Hz,OCH(CH$_3$)—), 7.18(2 H,brs,NH$_2$), 9.47 and 9.48(1 H,d,J=8.2 Hz,CONH), 11.34(1 H,s,=N—OH).

Mass (m/Z): 610(M$^+$), 611 (M$^+$+1).

Further, 7N hydrochloric acid/diethyl ether solution (0.02 ml) was added dropwise under ice cooling to a solution of the title compound (20 mg; 0.033 mmol) in ethyl acetate (2 ml), followed by stirring for 20 minutes. Precipitated crystals were collected by filtration and then dried, whereby the hydrochloride (18 mg; 0.028 mmol; 84.3%) of the title compound was obtained.

EXAMPLE 6

1-(2-Ethylbutanoyloxy)ethyl 7-[(Z)-2-(2-aminothiazol-4-yl)-2-hydroxyiminoacetamido]-3-[(Z)-3-carbamoyloxy-1-propenyl]-3-cephem-4-carboxylate

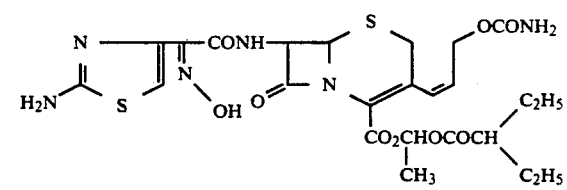

To a solution of the compound (200 mg; 0.408 mmol), which had been obtained in Example 1 in dry dimethylformamide (3 ml), a solution of 1-iodoethyl 2-ethylbutyrate (110 mg; 0.407 mmol) in dry dimethylformamide (1 ml) was added dropwise under ice cooling. The resulting mixture was stirred for 40 minutes. Ethyl acetate was added to the reaction mixture. The resulting mixture was washed with water and then with saturated saline. Magnesium sulfate was added to dry the mixture, followed by the concentration of the solvent under reduced pressure. The concentrate was added dropwise to n-hexane (50 ml). Precipitated crystals were collected by filtration and then dried, whereby the title compound (54 mg; 0.088 mmol; 21.7%) was obtained.

NMR (DMSO-d6) δ: 0.80–0.90(6 H,m,CH3x2), 1.40–1.55(7 H,m,CH2CH3x2,CHCH3), 2.15–2.25(1 H,m,OCOCH<), 3.59 and 3.60(2 H,ABq,J=18.0 Hz,CH2), 4.35–4.50(2 H,m,—CH2O), 5.24 and 5.25(1 H,d,J=4.8 Hz,CH), 5.55–5.70(1 H,m,=CH—), 5.80–5.90(1 H,m,CH), 6.23 and 6.27(1 H,d,J=11.7 Hz,—CH=), 6.51(2 H,brs,OCONH2), 6.66(1 H,s,thiazole-H), 6.86 and 6.90(1 H,q,J=5.5 Hz,OCH(CH3)—), 7.15(2 H,brs,NH2), 9.47 and 9.48(1 H,d,J=8.2 Hz,CONH), 11.31(1 H,s,=N—OH).

Mass (m/Z): 610(M+), 611(M++1). Further, 7N hydrochloric acid/diethyl ether solution (0.02 ml) was added dropwise under ice cooling to a solution of the title compound (24 mg; 0.039 mmol) in ethyl acetate (2 ml), followed by stirring for 20 minutes. Precipitated crystals were collected by filtration and then dried, whereby the hydrochloride (18 mg; 0.028 mmol; 71.3%) of the title compound was obtained.

EXAMPLE 7

Sodium 7-[(Z)-2-(2-aminothiazol-4-Yl)-2-methoxyiminoacetamido]-3-[(Z)-3-carbamoyloxy-1-propenyl]-3-cephem-4-carboxylate

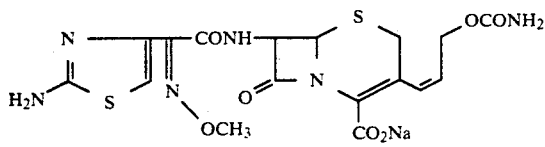

To a solution of the compound (960 mg; 1.136 mmol), which had been obtained in Preparation Example 6, in anisole (8 ml), trifluoroacetic acid (10 ml) was added dropwise under ice cooling. The resulting mixture was stirred at room temperature for 2 hours. The trifluoroacetic acid was distilled off under reduced pressure and the residue was added dropwise to a mixed solvent of isopropyl ether (20 ml) and n-hexane (80 ml). Precipitated crystals were collected by filtration. The crystals were added to 90% formic acid (10 ml), followed by stirring at room temperature for 3 hours. Under reduced pressure, the solvent was distilled off. The residue was trituated in isopropyl ether and crystals were collected by filtration. Those crystals were dissolved in methanol (10 ml), followed by the addition of sodium acetate (262 mg; 3.194 mmol). Under reduced pressure, the solvent was distilled off. The crude product was trituated in 2-propanol and crude crystals were collected by filtration. The crude crystals were purified by reversed phase chromatography on a silica gel column (5% aqueous methanol). Eluate was concentrated under reduced pressure and then lyophilized, whereby the title compound (138 mg; 0.274 mmol; 24.1%) was obtained.
NMR (DMSO-d6) δ:
3.54(2 H,ABq,J=16.5 Hz,CH2), 3.84(3 H,s,=N—OCH3),
4.50–4.70(2 H,dm,CH2), 5.04(1 H,d,J=4.8 Hz,CH),
5.20–5.30(1 H,m,=CH—), 5.57(1 H,dd,J=8.1,4.8 Hz,CH),
6.50(2 H,brs,OCONH2), 6.63(1 H,d,J=12.5 Hz,—CH=),
6.74(1 H,s,thiazole-H), 7.20(2 H,s,NH2),
9.52(1 H,d,J=8.1 Hz,CONH).
Mass (m/Z): 504(M+), 505(M++1).

EXAMPLE 8

Pivaloyloxymethyl 7-[(Z)-2-(2-aminothiazol-4-yl)-2-methoxyiminoacetamido]-3-[(Z)-3-carbamoyloxy-1-propenyl]-3-cephem-4-carboxylate

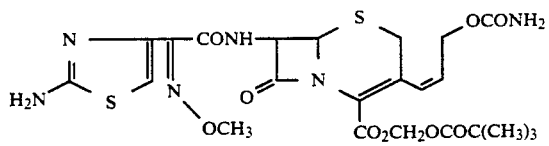

To a solution of the compound (116 mg; 0.230 mmol), which had been obtained in Example 7, in dry dimethylformamide (2 ml), a solution of iodomethyl pivalate (56 mg; 0.231 mmol) in dry dimethylformamide (1 ml) was added dropwise under ice cooling. The resulting mixture was stirred for 40 minutes. Ethyl acetate was added to the reaction mixture. The resulting mixture was washed with water and then with saturated saline. Magnesium sulfate was added to dry the mixture. The solvent was distilled off under reduced pressure, whereby the mixture was concentrated. The concentrate was added dropwise to n-hexane (50 ml). Precipitated crystals were collected by filtration and then dried, whereby the title compound (94 mg; 0.158 mmol; 68.5%) was obtained.

NMR (DMSO-d6) δ: 1.17(9 H,s,C(CH3)3), 3.62(2 H,ABq,J=18.0 Hz,CH2), 3.84(3 H,s,=N—OCH3), 4.30–4.50(2 H,dm,CH2), 5.25(1 H,d,J=4.8 Hz,CH), 5.60–5.70(1 H,m,=CH—), 5.75–5.85(3 H,m,CH,CO2CH2O—), 6.27(1 H,d,J=11.4 Hz,—CH=), 6.50(2 H,brs,—OCONH2), 6.75(1 H,s,thiazole-H), 7.22(2 H,brs,NH2), 9.61(1 H,d,J=8.1 Hz,CONH).

Mass (m/Z): 596(M+), 597(M++1).

Further, 7N hydrochloric acid/diethyl ether solution (0.02 ml) was added dropwise under ice cooling to a solution of the title compound (47 mg; 0.079 mmol) in ethyl acetate solution (2 ml), followed by stirring for 20 minutes. Precipitated crystals were collected by filtration and then dried, whereby the hydrochloride (42 mg; 0.066 mmol; 84.0%) of the title compound was obtained.

EXAMPLE 9

Sodium 7-[(Z)-2-(2-aminothiazol-4-yl)-2-hydroxyiminoacetamido]-3-[(Z)-3-(N-methylcarbamoyloxy)-1-propenyl]-3-cephem-4-carboxylate

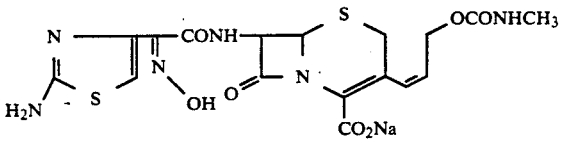

To a solution of the compound (1 g; 0.920 mmol), which had been obtained in Preparation Example 7, in anisole (8 ml), trifluoroacetic acid (10 ml) was added dropwise under ice cooling. The resulting mixture was stirred at room temperature for 2 hours. The reaction mixture was concentrated under reduced pressure and the concentrate was added dropwise to a mixed solvent of isopropyl ether (20 ml) and n-hexane (80 ml). Crystals were collected by filtration. The crystals were added to 90% formic acid (10 ml), followed by stirring at room temperature for 3 hours. Under reduced pressure, the solvent was distilled off. The residue was trituated in isopropyl ether and crystals were collected by filtration. Those crystals were dissolved in methanol (20 ml), followed by the addition of sodium acetate (226 mg; 2.755 mmol). Under reduced pressure, the solvent was distilled off. The crude product was trituated in 2-propanol and crude crystals were collected by filtration. The crude crystals were purified by reversed phase chromatography on a silica gel column (5% aqueous methanol). Eluate was concentrated under reduced pressure and then lyophilized, whereby the title compound (250 mg; 0.496 mmol; 53.9%) was obtained.

NMR (DMSO-$d_6$) δ: 2.56(3 H,d,J=4.4 Hz,NH—$CH_3$), 3.52(2 H,ABq,J=16.3 Hz,$CH_2$), 4.50–4.70(2 H,dm,$CH_2$), 5.03(1 H,d,J=4.8 Hz,CH), 5.20–5.30(1 H,m,=CH—), 5.58(1 H,dd,J=8.1,4.8 Hz,CH), 6.63(1 H,d,J=12.1 Hz,—CH=), 6.65(1 H,s,thiazole-H), 6.99(1 H,d,J=4.4 Hz,NH—$CH_3$), 7.09(2 H,s,$NH_2$), 9.38(1 H,d,J=8.1 Hz,CONH), 11.20(1 H,brs,=N—OH)

Mass (m/Z): 504($M^+$), 505($M^+$ + 1).

dried, whereby the title compound (86 mg; 0.144 mmol; 66.2%) was obtained.

NMR (DMSO-$d_6$) δ: 1.16(9 H,s,C($CH_3$)$_3$), 2.55(3 H,d,J=4.4 Hz,NH—$CH_3$), 3.60(2 H,ABq,J=17.8 Hz,$CH_2$), 4.35–4.55(2 H,dm,$CH_2$), 5.24(1 H,d,J=4.8 Hz,CH), 5.60–5.70(1 H,m,=CH—), 5.75–5.85(3 H,m,CH,$CO_2CH_2O$), 6.27(1 H,d,J=11.7 Hz,—CH=), 6.66(1 H,s,thiazole-H), 6.98(1 H,d,J=4.4 Hz,NH—$CH_3$), 7.12(2 H,s,$NH_2$), 9.47(1 H,d,J=8.1 Hz,CONH), 11.30(1 H,s,=N—OH).

Mass (m/Z): 596($M^+$), 597($M^+$ + 1).

Further, 7N hydrochloric acid/diethyl ether solution (0.04 ml) was added dropwise to an ethyl acetate solution of the title compound (44 mg; 0.074 mmol) under ice cooling, followed by stirring for 20 minutes. Precipitated crystals were collected by filtration and then dried, whereby the hydrochloride (40 mg; 0.063 mmol; 85.4%) of the title compound was obtained.

EXAMPLE 11

7-[2-(2-Aminothiazole)-2-hydroxyiminoacetamido]-3-(3-1H-tetrazolyl-1-propenyl-1-yl)-3-cephem-4-carboxylate

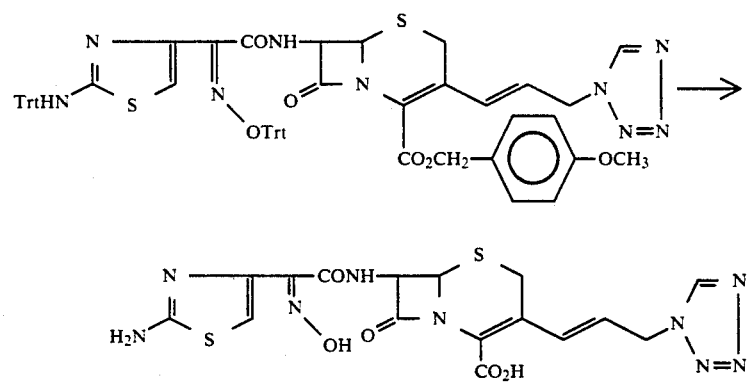

EXAMPLE 10

Pivaloyloxymethyl 7-[(Z)-2-(2-aminothiazol-4-yl)-2-hydroxyiminoacetamido]-3-[(Z)-3-(N-methylcarbamoyloxy)-1-propenyl]-3-cephem-4-carboxylate

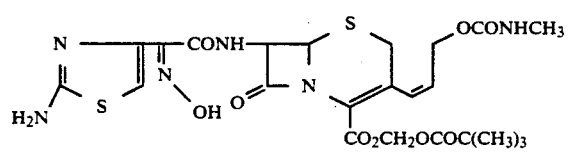

To a solution of the compound (110 mg; 0.218 mmol), which had been obtained in Example 9, in dry dimethylformamide (3 ml), a solution of iodomethyl pivalate (53 mg; 0.219 mmol) in dry dimethylformamide (0.5 ml) was added dropwise under ice cooling. The resulting mixture was stirred for 30 minutes. Ethyl acetate was added to the reaction mixture. The resulting mixture wa washed with water and then with saturated saline. Magnesium sulfate was added to dry the mixture. The mixture was concentrated under reduced pressure and concentrate was added dropwise to n-hexane (50 ml). Precipitated crystals were collected by filtration and then The compound (1.61 g) obtained in Preparation Example 9 was dissolved in anisole (12 ml), followed by the addition of trifluoroacetic acid (20.1 ml) under ice cooling. At the same temperature, the resulting mixture was stirred for 1 hour. After the solvent was distilled off under reduced pressure, diisopropyl ether was added and precipitated crystals were collected by filtration. Those crystals were then dissolved in a mixed solvent (70 ml) of formic acid and water, followed by stirring at room temperature for 4 hours. After completion of the reaction, water was added. Insoluble matter was filtered off. The filtrate was distilled off under reduced pressure and then subjected to reversed phase column chromatography (ODS), whereby the title compound (423 mg) was obtained.

NMR (DMSO-$d_6$) δ: 5.12(1 H,d,J=5 Hz), 5.75(1 H,dd,J=5 Hz,8 Hz), 6.0–6.35(1 H,m), 6.59(1 H,s), 6.80(1 H,d,J=16 Hz), 7.03(2 H,brs), 8.91(1 H,s), 9.39(1 H,d,J=8 Hz), 11.19(1 H,s).

EXAMPLE 12

7-[2-(2-Aminothiazole)-2-hydroxyiminoacetamido]-3-(3-2H-tetrazolyl-1-propenyl-1-yl)-3-cephem-4-carboxylic Acid

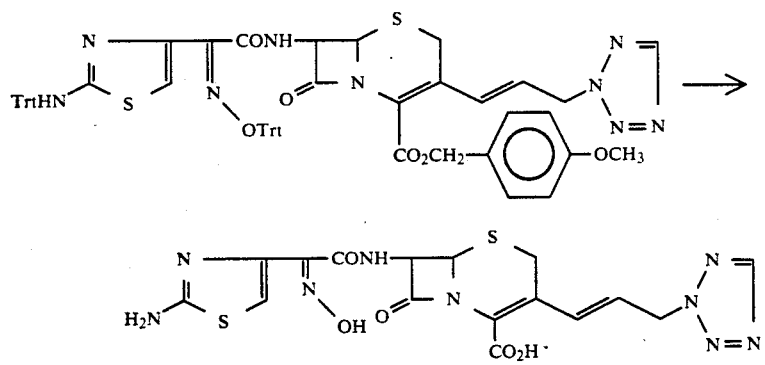

In a similar manner to Example 11, the title compound was obtained from the compound obtained in Preparation Example 10.

NMR (DMSO-$d_6$) δ: 5.11(1 H,d,J=5 Hz), 5.73(1 H,dd,J=5 Hz,8 Hz), 5.93-6.35(1 H,m), 6.59(1 H,s), 6.78(1 H,d,J=16 Hz), 7.04(2 H,brs), 9.31(1 H,s), 9.39(1 H,d,J=8 Hz), 11.17(1 H,s).

phy and the relevant fractions obtained were lyophilized, whereby the title compound (113 mg) was obtained.

NMR (DMSO-$d_6$) δ: 4.42(2 H,d,J=6.6 Hz), 5.00(1H,d,J=4.8 Hz,), 5.5-5.7(2 H,m), 6.45(2 H,brs), 6.65(1 H,s), 6.98(1H,d,J=16 Hz), 7.09(2 H,s), 9.41(1 H,brs)

PREPARATION EXAMPLE 12 p-Methoxybenzyl 7β-[(Z)-2-methoxyimino-2-(2-tritylaminothiazol-4-yl)acetamido]-3-(Z)-(pyrimidin-5-yl)vinyl]-3-cephem-4-carboxylate

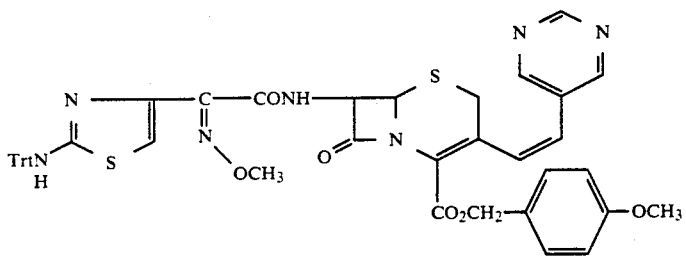

EXAMPLE 13

Sodium 7-[(Z)-2-(2-aminothiazol-4-yl)-2-hydroxyiminoacetamido]-3-[(E)-3-carbamoyloxy-1-propenyl]-3-cephem-4-carboxylate p-Methoxybenzyl 7β-](Z)-2-methoxyimino-2-(2-tritylaminothiazol-4-yl)acetamido]-3-[(triphenylphosphoranylidene)methyl]-3-cephem-4-carboxylate (3 g) and 5-pyrimidinaldehyde (0.8 g) were stirred for 12 hours in dichloromethane (40 ml). The reaction mixture was concentrated to about 15 ml and then subjected to

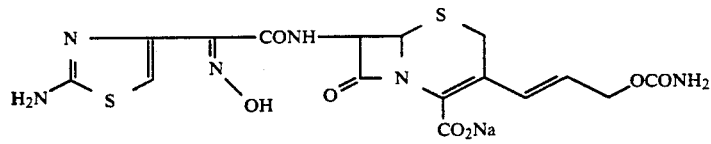

Trifluoroacetic acid (TFA) (6.2 ml) was added dropwise to a solution of the compound (iii) (620 mg), which had been obtained in Preparation Example 11, in anisole (3.1 ml) under ice cooling, followed by stirring for 2.5 hours. After the solvent wa distilled off under reduced pressure, the residue was added with isopropyl ether (IPE). Precipitated crystals were collected by filtration. The crystals were added to 74% HCOOH (20 ml), followed by stirring at room temperature for 2 hours. After the reaction mixture was added with H$_2$O, insoluble matter was filtered off and the filtrate was subjected to distillation under reduced pressure. The residue was added with an aqueous sodium acetate solution. The resulting solution was subjected to ODS chromatograchromatography on a silica gel column. Relevant fractions were combined and concentrated, whereby an oily matter was obtained. It was added dropwise to a mixed solvent of isopropyl ether (20 ml) and n-hexane (80 ml). The resulting precipitate was collected by filtration, whereby the title compound (1.8 g) was obtained.

NMR (CDCl$_3$) δ: 3.18,3.51(2 H,ABq,J=18 Hz), 3.82(3 H,s), 4.10(3 H,s), 5.12(1 H,d,J=5 Hz), 5.20(2 H,s), 5.98(1 H,dd,J=5 Hz,9 Hz), 6.51(1 H,d,J=14 Hz), 6.77(1 H,s), 6.78(1 H,d,J=14 Hz), 6.96(2 H,ABq,J=8 Hz), 7.22-7.55(17 Hz,m), 8.62(2 H,s), 9.12(1 H,s).

PREPARATION EXAMPLE 13 p-Methoxybenzyl 7β-[(Z)-2-(2-tritylaminothiazol-4-yl)-2-trityloxyiminoacetamido]-3-[(Z)-(pyrimidin-5-yl)vinyl]-3-cephem-4-carboxylate

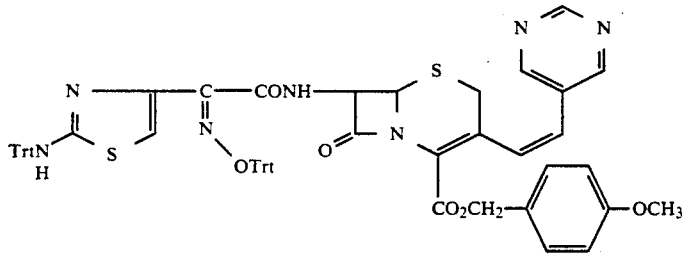

p-Methoxybenzyl 7β-[(Z)-2-(2-tritylaminothiazol-4-yl)-2-trityloxyiminoacetamido]-3-[(triphenylphosphoranylidene)methyl]-3-cephem-4-carboxylate (4 g) and 5-pyrimidinaldehyde (0.8 g) were stirred for 12 hours in dichloromethane (40 ml). The reaction mixture was concentrated to about 15 ml and then subjected to chromatography on a silica gel column. Relevant fractions were combined and concentrated, whereby an oily matter was obtained. It was added dropwise to a mixed solvent of isopropyl ether (20 ml) and n-hexane (80 ml). The resulting precipitate was collected by filtration, whereby the title compound (1.5 g) was obtained.

NMR (CDCl₃) δ: 3.00, 3.40(2 H,ABq,J=18 Hz), 3.82(3 H,s), 5.08(1 H,d,J=5 Hz), 5.10(2 H,s), 6.05(1 H,dd,J=5 Hz,9 Hz), 6.35, 6.52(2 H,ABq,J=14 Hz), 6.70(1 H,s), 6.85(2 H,ABq,J=8 Hz), 7.22–7.55(32 H,m), 8.50(2 H,s), 8.91(1 H,s).

PREPARATION EXAMPLE 14 p-Methoxybenzyl 7β-[(Z)-2-(2-tritylaminothiazol-4-yl)-2-trityloxyiminoacetamido]-3-[(Z)-(2-methylpyrimidin)-5-yl)vinyl]-3-cephem-4-carboxylate

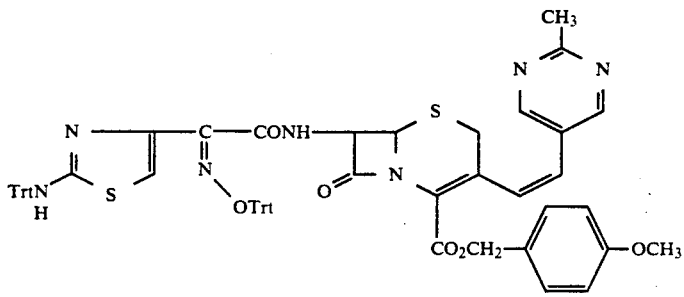

p-Methoxybenzyl 7β-[(Z)-2-(2-tritylaminothiazol-4-yl)-2-trityloxyiminoacetamido]-3-[(triphenylphosphoranylidene)methyl]-3-cephem-4-carboxylate (3 g) and 2-methylpyrimidine-5-carboxaldehyde (0.5 g) were stirred for 12 hours in dichloromethane (40 ml). The reaction mixture was concentrated to about 15 ml and then subjected to chromatography on a silica gel column. Relevant fractions were combined and concentrated, whereby an oily matter was obtained. It was added dropwise to a mixed solvent of isopropyl ether (20 ml) and n-hexane (80 ml). The resulting precipitate was collected by filtration, whereby the title compound (2.3 g) was obtained.

PREPARATION EXAMPLE 15 p-Methoxybenzyl 7β-[(Z)-2-(2-tritylaminothiazol-4-yl)-2-trityloxyiminoacetamido]-3-[(E)-(4-aminopyrimidin)-5-yl)vinyl]-3-cephem-4-carboxylate

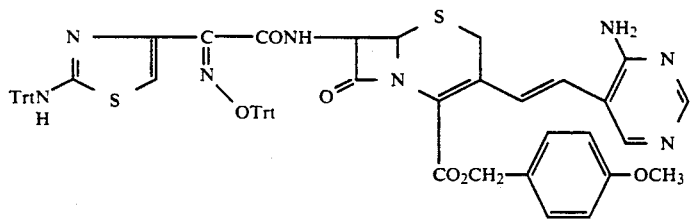

p-Methoxybenzyl 7β-[(Z)-2-(2-tritylaminothiazol-4-yl)-2-trityloxyiminoacetamido]-3-[(triphenylphosphoranylidene)methyl]-3-cephem-4-carboxylate (3 g) and 4-aminopyrimidine-5-carboxaldehyde (0.5 g) were stirred for 12 hours in dichloromethane (10 ml). Ethyl acetate (100 ml) was added. The organic layer was washed with water, dried over magnesium sulfate, and then concentrated. An oily matter was subjected to chromatography on a silica gel column. Relevant fractions were combined and concentrated. The residue was dissolved in a small amount of chloroform. The resulting solution was added dropwise to a mixed solvent of isopropyl ether (20 ml) and n-hexane (80 ml).

The resulting precipitate was collected by filtration, whereby the title compound (1.0 g) was obtained.

NMR (CDCl₃) δ: 3.4–3.6(1 H,m), 3.72(3 H,s), 4.10(1 H,ABq,J=18 Hz), 5.2–5.3(3 H,m), 5,83(1 H,dd,J=5 Hz,8 Hz), 6.58(1 H,s), 6.83(2 H,d,J=8 Hz), 7.00–7.40(32 H,m), 7.3–7.8(2 H,m), 8.10(1 H,s), 8.23(1 H,s), 8.70(1 H,s), 9.85(1 H,d,J=8 Hz).

H,ABq,J=8 Hz), 7.10–7.40(32 H,m), 8.20(1 H,s), 8.58(1 H,s), 8.61(1 H,s), 8.83(1 H,s),

PREPARATION EXAMPLE 17 p-Methoxybenzyl 7β-[(Z)-2-methoxyimino-2-(2-tritylaminothiazol-4-yl)acetamido]-3-(E)-(pyrazin-5-yl vinyl]-3-cephem-4-carboxylate

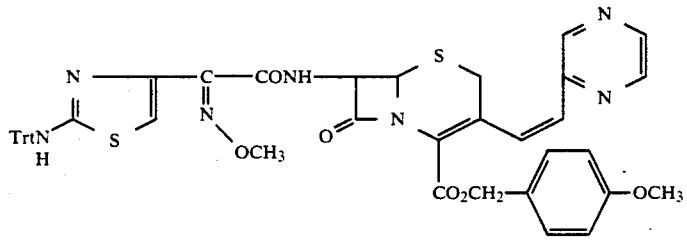

PREPARATION EXAMPLE 16 p-Methoxybenzyl 7β-[(Z)-2-(2-tritylaminothiazol-4-yl)-2-trityloxyiminoacetamido]-3-[(Z)-(4-methoxypyrimidin)-5-yl)vinyl]-3-cephem-4-carboxylate

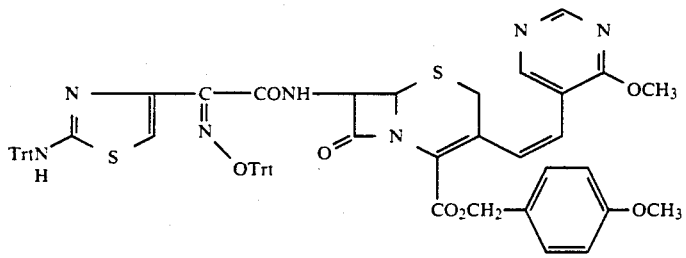

p-Methoxybenzyl 7β-[(Z)-2-(2-tritylaminothiazol-4-yl)-2-trityloxyiminoacetamido]-3-[(triphenylphosphoranylidene)methyl]-3-cephem-4-carboxylate (3 g) and 4-methoxypyrimidine-5-carboxaldehyde (0.5 g) were stirred for 12 hours in dichloromethane (40 ml). The reaction mixture was concentrated and the resulting oily substance was subjected to chromatography on a silica gel column. Relevant fractions were combined and concentrated. The residue was dissolved in a small amount of chloroform and the resulting solution was added dropwise to a mixed solvent of isopropyl ether (20 ml) and n-hexane (80 ml). The resulting precipitate was collected by filtration, whereby the title compound (1.6 g) was obtained.

NMR (CDCl₃) δ: 2.98, 3.31(2 H,ABq,J=18 Hz), 3.78(3 H,s), 3.98(3 H,s), 5.02(1 H,d,J=5 Hz), 5.13(2 H,s), 6.00(1 H,dd,J=5 Hz,8 Hz), 6.40(1 H,s), 6.43,6.65(2 H,ABq,J=12 Hz), 6.78(1 H,d,J=8 Hz), 6.85(2 p-Methoxybenzyl 7β-[(Z)-2-(2-methoxyimino-2-(2-tritylaminothiazol-4-yl)acetamido]-3-[(triphenylphosphoranylidene)methyl]-3-cephem-4-carboxylate (3 g) and 2-pyrazinaldehyde (0.3 g) were stirred for 12 hours in dichloromethane (40 ml). The reaction mixture was concentrated to about 15 ml and then subjected to chromatography on a silica gel column. Relevant fractions were combined and concentrated, whereby an oily matter was obtained. It was added dropwise to a mixed solvent of isopropyl ether (20 ml) and n-hexane (80 ml). The resulting precipitate was collected by filtration, whereby the title compound (0.8 g) was obtained.

PREPARATION EXAMPLE 18 p-Methoxybenzyl 7β-[(Z)-2-(2-methoxyimino-2-(tritylaminothiazol-4-yl)acetamido]-3-[(E),(Z)-(4,6-dichloropyrimidin)-5-yl)vinyl]-3-cephem-4-carboxylate

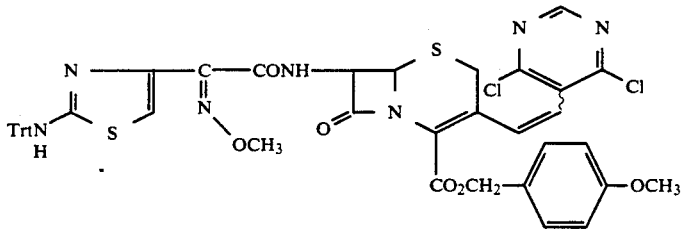

p-Methoxybenzyl 7β-[(Z)-2-methoxyimino-2-(2-tritylaminothiazol-4-yl)acetamido]-3-[(triphenylphosphoranylidene)methyl]-3-cephem-4-carboxylate (3 g) and 4,6-dichloropyrimidin-5-carboxaldehyde (0.7 g) were stirred for 12 hours in dichloromethane (40 ml). The reaction mixture was concentrated and then subjected to chromatography on a silica gel column. Relevant fractions were combined and concentrated, whereby an oily matter was obtained. It was added dropwise to a mixed solvent of isopropyl ether (20 ml) and n-hexane (80 ml). The resulting precipitate was collected by filtration, whereby the title compound (0.6 g) was obtained.

EXAMPLE 14

Sodium 7β-[(Z)-2-(2-aminothiazol-4-yl)-2-methoxyimino]acetamido]-3-[(Z)-(pyrimidin 5-yl)vinyl]-3-cephem-4-carboxylate

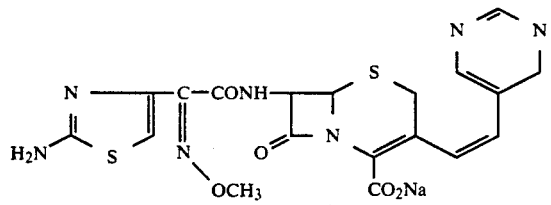

The compound (1.8 g) of Preparation Example 1 was added to a solution of trifluoroacetic acid (3 ml) in anisole (3 ml), followed by a reaction for 1 hour. Isopropyl ether (50 ml) was added and the resulting precipitate was collected by filtration. It was dissolved in methanol (20 ml) which contained sodium acetate (0.5 g). The solution was concentrated under reduced pressure, followed by the addition of isopropyl alcohol (30 ml) to obtain the title compound in a crude form. It was dissolved in water (15 ml) and then purified by reversed-phase silica gel chromatography, whereby the title compound (500 mg) was obtained.

NMR (D$_2$O) δ: 3.43, 3.76(2 H,ABq,J=18 Hz), 4.11(3 H,s), 5.42(1 H,d,J=4.7 Hz), 5.92(1 H,d,J=4.7 Hz), 6.67(2 H,s), 7.14(1 H,s), 8.82(2 H,s), 9.08(1 H,s).

EXAMPLE 15

Pivaloyloxymethyl 7β-[(Z)-2-(2-aminothiazol-4-yl)-2-methoxyimino]acetamido]-3-[(Z)-(pyrimidin-5-yl)vinyl]-3-cephem-4-carboxylate

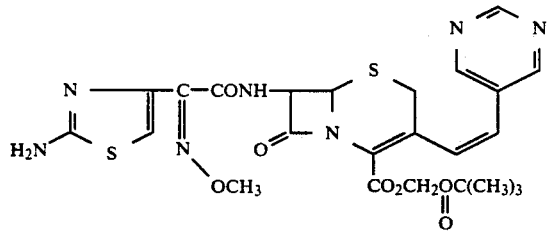

Sodium 7β-[(Z)-2-(2-aminothiazol-4-yl)-2-(methoxyimino)acetamido]-3-[(Z) 2-(pyrimidin-5-yl) -vinyl]-3-cephem-4-carboxylate (100 mg) was dissolved in N,N-dimethylacetamide (2 ml), followed by the addition of pivaloyloxymethyl iodide (50 mg). They were reacted for 1 hour. Ethyl acetate (30 ml) was added. The resulting mixture was washed with water (30 ml), dried over magnesium sulfate, and then concentrated under reduced pressure. Ether was added to the residue. The resulting precipitate was collected by filtration, whereby the title compound (80 mg) was obtained.

NMR (CDCl$_3$) δ: 1.2(9 H,s), 3.10, 3.43(2 H,ABq,J=18 Hz), 4.00(3 H,s), 5.10(1 H,d,J=5 Hz), 5.7-6.0(3 H,m), 6.42,6.65(2 H,ABq.J=12 Hz), 6.82(1 H,s), 7.53(1 H,d,J=10 Hz), 8.53(2 H,s), 9.00(1 H,s),

EXAMPLE 16

Sodium 7β-[(Z)-2-(2-aminothiazol-4-yl)-2-(hydroxyimino)acetamido]-3-[(Z)-2 (pyrimidin-5-yl)vinyl]-3-cephem-4-carboxylate

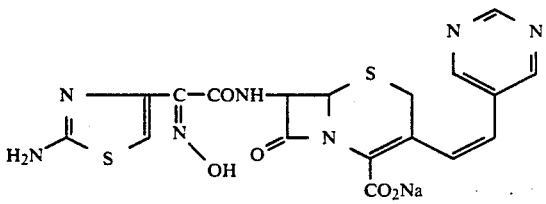

The compound (1.5 g) of Preparation Example 13 was added to a solution of trifluoroacetic acid (3 ml) in anisole (3 ml), followed by a reaction for 1 hour. Isopropyl ether (50 ml) was added and the resulting precipitate was collected by filtration. It was dissolved in formic acid (15 ml), followed by stirring for 3 hours. The solvent was distilled off under reduced pressure. Isopropyl ether was added and the resulting precipitate was collected by filtration. It was dissolved in methanol (20 ml) which contained sodium acetate (0.5 g). The resulting solution was concentrated under reduced pressure, followed by the addition of isopropyl alcohol (30 ml) to obtain the title compound in a crude form. It was dissolved in water (15 ml) and then purified by reversed-phase silica gel chromatography, whereby the title compound (150 mg) was obtained.

NMR (D$_2$O) δ: 3.43, 3.77(2 H,ABq,J=17.6 Hz), 5.44(1 H,d,J=4.4 Hz), 6.68(2 H,s), 7.12(1 H,s), 8.82(2 H,s), 9.08(1 H,s).

EXAMPLE 17

Pivaloyloxymethyl 7β-[(Z)-2-(2-aminothiazol-4-yl)-2-(hydroxyimino)acetamido]-3-[(Z)-2-(pyrimidin-5-yl)vinyl]-3-cephem-4-carboxylate

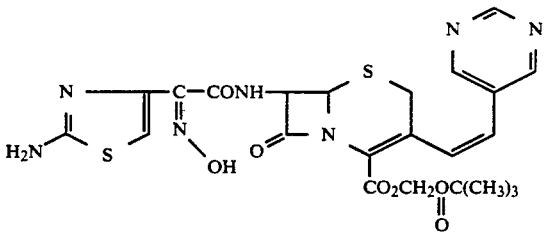

The compound (100 mg) of Example 16 was dissolved in N,N-dimethylacetamide (2 ml), followed by the addition of pivaloyloxymethyl iodide (50 mg). They were reacted for 1 hour. Ethyl acetate (50 ml) was added. The resulting mixture was washed with water, dried over magnesium sulfate, and then concentrated under reduced pressure. Ether was added to the residue and the resulting solid was collected by filtration, whereby the title compound (80 mg) was obtained.

NMR (CDCl$_3$) δ: 1.22(9 H,s), 3.08,3.50(2 H,ABq,J=18 Hz), 5.14(1 H,d,J=5 Hz), 5.7-6.1(3 H,m), 6.48,6.73(2 H,ABq,J=12 Hz), 6.95(1 H,s), 8.60(2 H,s), 8.98(1 H,s).

EXAMPLE 18

2-Ethylbutanoyloxymethyl 7β-[(Z)-2-(2-aminothiazol-4-yl)-2-(hydroxyimino)acetamido]-3-[(Z)-2-(pyrimidin-5-yl)vinyl]-3-cephem-4-carboxylate

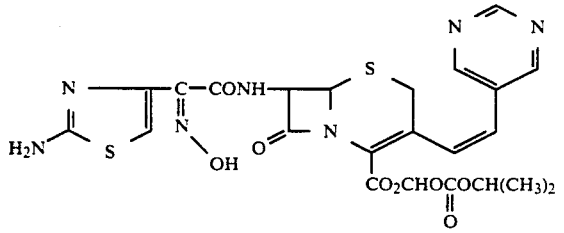

The compound (100 mg) of Example 16 was dissolved in N,N-dimethylacetamide (2 ml), followed by the addition of 2-ethylbutanoyloxymethyl iodide (50 mg). They were reacted for 1 hour. Ethyl acetate (50 ml) was added. The resulting mixture was washed with water, dried over magnesium sulfate, and then concentrated under reduced pressure. Ether was added to the residue and the resulting solid was collected by filtration, whereby the title compound (55 mg) was obtained.

NMR (CDCl$_3$) δ: 1.88(6 H,t,J=8 Hz), 1.4–1.8(4 H,m), 2.1–2.4(1 H,m), 3.24, 3.48(2 H,ABq,J=18 Hz), 5.14(1 H,d,J=5 Hz), 5.87(2 H,s), 5.80–6.10(1 H,m), 6.52,6.75(2 H,ABq,J=12 Hz), 6.97(1 H,s), 8.60(2 H,s), 8.97(1 H,s).

EXAMPLE 19

1-(Isopropyloxycarbonyloxy)ethyl 7β-[(Z)-2-(2-aminothiazol-4-yl)-2-(hydroxyimino)acetamido]-3-[(Z)-2-(pyrimidin-5-yl)vinyl]-3-cephem-4-carboxylate

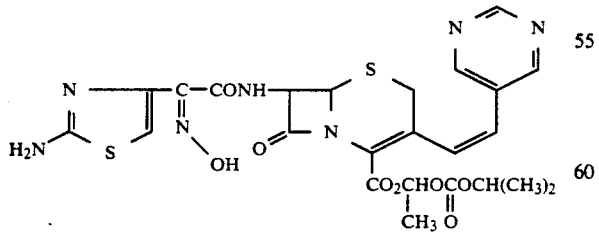

The compound (100 mg) of Example 16 was dissolved in N,N-dimethylacetamide (2 ml), followed by the addition of 1-(isopropyloxycarbonyloxy)ethyl iodide (50 mg). They were reacted for 1 hour. Ethyl acetate (50 ml) was added. The resulting mixture was washed with water, dried over magnesium sulfate, and then concentrated under reduced pressure. Ether was added to the residue and the resulting solid was collected by filtration, whereby the title compound (85 mg) was obtained.

NMR (CDCl$_3$) δ: 1.35(6 H,d,J=7 Hz), 1.56 and 1.62(3 H,d,J=3 Hz in total), 3.08, 3.43(2 H,ABq,J=18 Hz), 4.80–5.00(1 H,m), 5.13(1 H,d,J=5 Hz), 5.8–6.1(2 H,m), 6.44, 6.50, 6.77 and 6.79(2 H,ABq,J=12 Hz in total), 6.91 and 6.93(1 H,s in total), 8.58 and 8.60(2 H,s in total), 8.97 and 8.99(1 H,s in total).

EXAMPLE 20

(5-Methyl-2-oxo-1,3-dioxolan-4-yl)methyl 7β-[(Z)-2-(2-aminothiazol-4-yl)-2-(hydroxyimino)acetamido]-3-[(Z)-2-(pyrimidin-5-yl)vinyl]-3-cephem-4-carboxylate

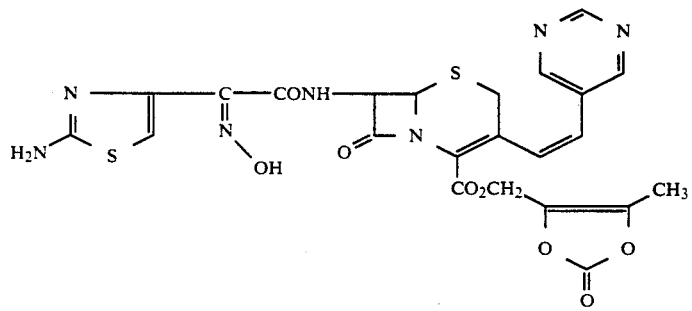

The compound (100 mg) of Example 16 was dissolved in N,N-dimethylacetamide (2 ml), followed by the addition of 4-bromomethyl-5-methyl-1,3-dioxolan-2-one (50 mg). They were reacted for 1 hour. Ethyl acetate (50 ml) was added. The resulting mixture was washed with water, dried over magnesium sulfate, and then concentrated under reduced pressure. Ether was added to the residue and the resulting solid was collected by filtration, whereby the title compound (15 mg) was obtained.

NMR (CDCl$_3$) δ: 2.1(3 H,s), 3.2–3.5(2 H,m), 4.77, 4.96(2 H,ABq,J=14 Hz), 5.23(1 H,d,J=5 Hz), 5.82(1 H,dd,J=5 Hz,8 Hz), 6.50(2 H,s), 6.62(1 H,s), 8.60(2 H,s), 8.97(1 H,s).

EXAMPLE 21

Sodium 7β-[(Z)-2-(2-aminothiazol-4-yl)-2-(hydroxyimino)acetamido]-3-[(Z)-2-(2-methylpyrimidin)-5-yl)vinyl]-3-cephem-4-carboxylate

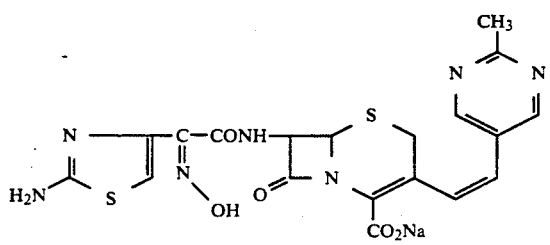

The compound (2.3 g) of Preparation Example 14 was added to a solution of trifluoroacetic acid (3 ml) in anisole (3 ml), followed by a reaction for 1 hour. Isopropyl ether (50 ml) was added and the resulting precipitate was collected by filtration. It was dissolved in formic acid (15 ml), followed by stirring for 3 hours. The solvent was distilled off under reduced pressure. Isopropyl ether was added and the resulting precipitate was collected by filtration. It was dissolved in methanol (20 ml) which contained sodium acetate (0.8 g). The resulting solution was concentrated under reduced pressure, followed by the addition of isopropyl alcohol (30 ml) to obtain the title compound in a crude form. It was dissolved in water (15 ml) and then purified by reversed-phase silica gel chromatography, whereby the title compound (170 mg) was obtained.

NMR (D$_2$O) δ: 2.77(3 H,s), 3.39, 3.72(2 H,ABq,J=17.6 Hz), 5.43(1 H,d,J=4.7 Hz), 5.96(1 H,d,J=4.7 Hz), 6.65(2 H,s), 7.11(1 H,s), 8.70(2 H,s).

EXAMPLE 22

Pivaloyloxymethyl 7-β-[(Z)-2-(2-aminothiazol-4-yl)-2-(hydroxyimino)acetamido]-3-[(Z)-2-(2-methylpyrimidin)-5-yl)vinyl]-3-cephem-4-carboxylate

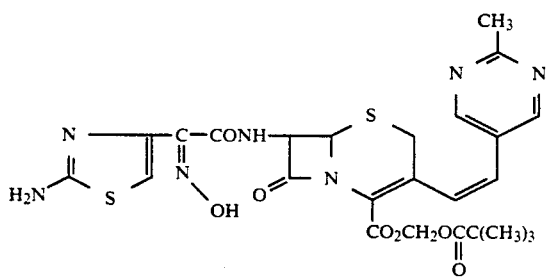

In a similar manner to Example 21, the title compound (80 mg) was obtained from sodium 7β-[(Z)-2-(2-aminothiazol-4-yl)-2-(hydroxyimino)acetamido]-4-[(Z)-2-(2-methylpyrimidin-5-yl)vinyl]-3-cephem-4-carboxylate (110 mg).

NMR (CDCl$_3$) δ: 1.2(9 H,s), 2.65(2 H,s), 3.15, 3.45(2 H,ABq,J=18 Hz), 5.14(1 H,d,J=5 Hz), 5.6–6.1(3 H,m), 6.42, 6.63(2 H,ABq,J=12 Hz), 6.85(1 H,s), 8.45(2 H,s).

EXAMPLE 23

Sodium 7β[(Z)-2-(2-aminothiazol-4-yl)-2-(hydroxyimino)acetamido]-3-[(E)-2-(4-aminopyrimidin-5-yl)vinyl]-3-cephem-4-carboxylate

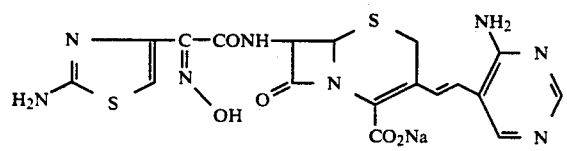

The compound (1.0 g) obtained in Preparation Example 15 was added to a solution of trifluoroacetic acid (2 ml) in anisole (2 ml), followed by a reaction for 1 hour. Isopropyl ether (50 ml) was added and the resulting precipitate was collected by filtration. It was dissolved in formic acid (10 ml), followed by stirring for 3 hours. The solvent was distilled off under reduced pressure. Isopropyl ether was added and the resulting precipitate was collected by filtration. It was dissolved in methanol (20 ml) which contained sodium acetate (0.5 g). The resulting solution was concentrated under reduced pressure, followed by the addition of isopropyl alcohol (30 ml) to obtain the title compound in a crude form. It was dissolved in water (15 ml) and then purified by reversed-phase silica gel chromatography, whereby the title compound (105 mg) was obtained.

NMR (D$_2$O) δ: 3.88, 3.98(1 H,ABq,J=16.9 Hz), 5.44(1 H,d,J=4.4 Hz), 5.99(1 H,d,J=4.4 Hz), 6.74, 7.28(2 H,ABq,J=16.1 Hz), 7.13(1 H,s), 8.40(1 H,s), 8.45(1 H,s).

EXAMPLE 24

Pivaloyloxymethyl 7β-[(Z)-2-(2-aminothiazol-4-yl)-2-(hydroxyimino)acetamido]-3-[(E)-2-(4-aminopyrimidin-5-yl)vinyl]-3-cephem-4-carboxylate dihydrochloride

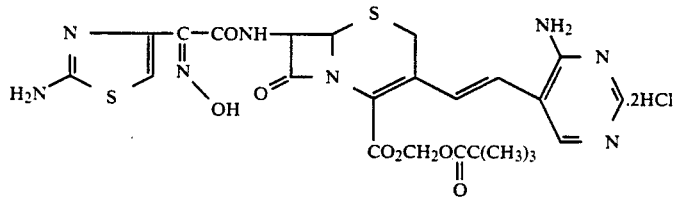

The compound (100 mg) of Example 23 was dissolved in N,N-dimethylacetamide (1 ml), followed by the addition of pivaloyloxymethyl iodide (50 mg). They were reacted for 1 hour, and added to ether (50 ml) slowly. The resulting precipitate was collected by filtration, dissolved in 0.2N aqueous hydrochloric acid solution, and purified by reversed-phase chromatography on a silica gel column, whereby the title compound (20 mg) was obtained.

NMR (DMSO) δ: 1.14(9 H,s), 3.70, 4.16(2 H,ABq,J=18 Hz), 5.31(1 H,d,J=5.1 Hz), 5.8–5.9(3 H,m), 5.95(1 H,d,J=5.1 Hz), 6.73(1 H,s), 6.94,7.26(1 H,ABq,J=16 Hz), 8.45(1 H,s), 8.68(1 H,s), 9.57(1 H,d,J=8.4 Hz).

EXAMPLE 25

Sodium 7β-[(Z)-2-(2-aminothiazol-4-yl)-2-(hydroxyimino)acetamido]-3-[(Z)-2-(4-methoxypyrimidin-5-yl)vinyl]-3-cephem-4-carboxylate

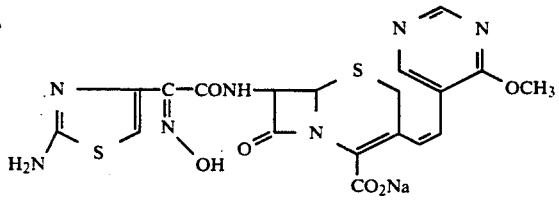

The compound (1.6 g) obtained in Preparation Example 16 was added to a solution of trifluoroacetic acid (2 ml) in anisole (1.2 ml), followed by a reaction for 1 hour.

Isopropyl ether (50 ml) was added and the resulting precipitate was collected by filtration. It was dissolved in formic acid (10 ml), followed by stirring for 3 hours. The solvent was distilled off under reduced pressure. Isopropyl ether was added and the resulting precipitate was collected by filtration. It was dissolved in methanol (20 ml) which contained sodium acetate (0.8 g). The resulting solution was concentrated under reduced pressure, followed by the addition of isopropyl alcohol (30 ml) to obtain the title compound in a crude form. It was dissolved in water (15 ml) and then purified by reversed-phase silica gel chromatography, whereby the title compound (115 mg) was obtained.

NMR (D$_2$O) δ: 3.37, 3.68(2 H,ABq,J=17.6 Hz), 4.15(3 H,s), 5.38(1 H,d,J=4.4 Hz), 5.92(1 H,d,J=4.4 Hz), 6.58,6.67(2 H,ABq,J=12.1 Hz), 7.10(1 H,s), 8.46(1 H,s), 8.72(1 H,s).

EXAMPLE 26

Pivaloyloxymethyl 7β-(Z)-2-(2-aminothiazol-4-yl)-2-(hydroxyimino)acetamido]-3-[(Z)-2-(4-methoxypyrimidin-5-yl)vinyl]-3-cephem-4-carboxylate

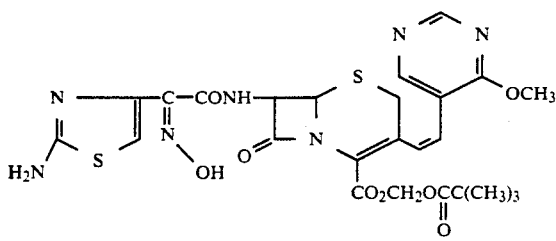

In a similar manner to Example 21, the title compound (75mg) was obtained from sodium 7β-[(Z)-2-(2-aminothiazol-4-yl)-2-(hydroxyimino)acetamido]-3-[(Z)-2-(4-methoxypyrimidin-5-yl)vinyl]-3-cephem-4-carboxylate (100 mg).

NMR (CDCl$_3$) δ: 1.21(9 H,s), 3.10, 3.43(2 H,ABq,J=18 Hz), 4.00(3 H,s), 5.12(1 H,d,J=5 Hz),.5.7–6.1(3 H,m), 6.61(2 H,s), 6.90(1 H,s), 8.26(1 H,s), 8.57(1 H,s).

EXAMPLE 27

Sodium 7β-[(Z)-2-(2-aminothiazol-4-yl)-2-(methoxyimino)acetamido]-3-[(E)-2-(pyrazin-2-yl)vinyl]-3-cephem-4-carboxylate

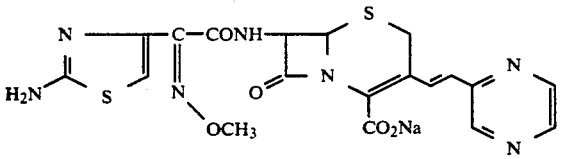

The compound (0.8 g) of Preparation Example 17 was added to a solution of trifluoroacetic acid (2 ml) in anisole (2 ml), followed by a reaction for 1 hour. Isopropyl ether (50 ml) was added and the resulting precipitate was collected by filtration. It was dissolved in methanol (20 ml) which contained sodium acetate (0.3 g). The resulting solution was concentrated under reduced pressure, followed by the addition of isopropyl alcohol (30 ml) to obtain the title compound in a crude form. It was dissolved in water (15 ml) and purified by reversed-phase silica gel chromatography, whereby the title compound (110 mg) was obtained.

NMR (D$_2$O) δ: 3.89, 4.01(2 H,ABq,J=17.2 Hz), 4.12(3 H,s), 5.44(1 H,d,J=4.8 Hz), 5.97(1 H,d,J=4.8 Hz), 6.96(1 H,d,J=16.1 Hz), 7.15(1 H,s), 7.78(1 H,d,J=16.1 Hz), 8.52(1 H,d,J=2.5 Hz), 8.63(1 H,d,J=2.5 Hz,1.1 Hz), 8.79(1 H,d,J=1.1 Hz).

EXAMPLE 28

Pivaloyloxymethyl 7β-(Z)-2-(2 aminothiazol-4-yl)-2-(methoxyimino)acetamido]-3-[(E)-2-(pyrazin-2-yl)vinyl]-3-cephem-4-carboxylate

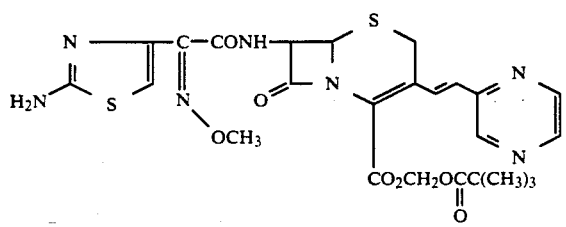

In a similar manner to Example 27, the title compound (65mg) was obtained from sodium 7β-[(Z)-2-(2-aminothiazol-4-yl)-2-(methoxyimino)acetamido]-3-[(E)-2-(pyrazin-2-yl)vinyl]-3-cephem-4-carboxylate (100 mg).

NMR (CDCl$_3$) δ: 1.22(9 H,s), 3.76, 3.98(2 H,ABq,J=18 Hz), 4.10(3 H,s), 5 20(1 H,d,J=5 Hz), 6.0–6.3(3 H,m), 6.97, 8.09(2 H,ABq,J=18 Hz), 7.00(1 H,s), 8.45(1 H,d,J=2 Hz), 8.57(1 H,dd,J=2 Hz,1 Hz), 8.67(1 H,d,J=1 Hz).

EXAMPLE 29

Sodium 7β-[(Z)-2-(2-aminothiazol-4-yl)-2-(methoxyimino)acetamido]-3-[(Z)-2-(4,6-dichloropyrimidin-5-yl)vinyl]-3-cephem-4-carboxylate and Sodium 7β-[(Z)-2-(2-aminothiazol-4-yl)-2-(methoxyimino)acetamido-3-[(E)-2-(4,6-dichloropyrimidin-5-yl)vinyl]-3-cephem-4-carboxylate

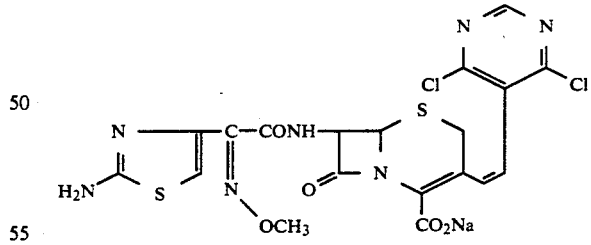

The compound (0.6 g) of Preparation Example 18 was added to a solution of trifluoroacetic acid (1.5 ml) in anisole (1.5 ml), followed by a reaction for 1 hour. Isopropyl ether (50 ml) was added and the resulting precipitate was collected by filtration. It was dissolved in methanol (10 ml) which contained sodium acetate (0.3 g). The resulting solution was concentrated under reduced pressure, followed by the addition of isopropyl alcohol (30 ml) to obtain the title compound in a crude form. It was dissolved in water (15 ml) and purified by reversed-phase silica gel chromatography, whereby the title compound (120 mg) was obtained.

(Z)-Isomer:

NMR (D$_2$O)&: 3.42, 3.77(2 H,ABq,J=17.1 Hz), 4.10(3 H,s), 5.36(1 H,d,J=4.8 Hz), 5.88(1 H,d,J=4.8 Hz), 6.54,6.73(2 H,ABq,J=12.1 Hz), 7.12(1 H,s), 8.80(1 H,s).

(E)-Isomer:

NMR (D$_2$O) δ: 3.93, 4.02(2 H,ABq,J=16.9 Hz), 4.13(3 H,s), 5.45(1 H,d,J=4.8 Hz), 5.98(1 H,d,J=4.8 Hz), 6.81,7.57(2 H,ABq,J=16.5 Hz), 7.16(1 H,s), 8.73(1 H,s).

PREPARATION EXAMPLE 19

4-Methoxyphenylmethyl 7-[(Z)-2-(2-tritylaminothiazol-4-yl)-2-trityloxyiminoacetamido]-3-[(Z)-3-(N,N-dimethylcarbamoyloxy)-1-propenyl]-3-cephem-4-carboxylate

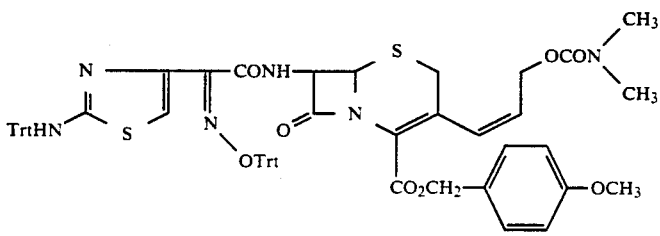

A solution of 4-methoxyphenylmethyl 7-[(Z)-2-(2-tritylaminothiazol-4-yl)-2-trityloxyiminoacetamido]-3-(1-triphenylphosphoranyliden)methyl-3-cephem-4-carboxylate (34.46 g; 27.63 mmol) and N,N-dimethylcarbamoyloxyacetaldehyde (4 g; 30.53 mmol) in dichloromethane (150 ml) was stirred at room temperature for 16 hours. After the solvent was distilled off under reduced pressure, the residue was purified by chromatography on a silica gel column (n-hexane:ethyl acetate=1:1) whereby the title compound (11.3 g; 10.26 mmol; 37.1%) was obtained.

NMR (CDCl$_3$) δ: 2.84(6 H,s,N(CH$_3$)2), 3.32(2 H,ABq,J=18.0 Hz,CH$_2$), 3.78(3 H,s,OCH$_3$), 4.30–4.70(2 H,m,CH$_2$), 5.06(1 H,d,J=4.8 Hz,CH), 5.16(2 H,bs,CO$_2$CH$_2$—), 5.50–6.10(2 H,m,CH,=CH—), 6.26(1H,d,J=11.8 Hz,—CH=), 6.40–7.50(35 H,m,thiazole-H,Ph-Hx34).

EXAMPLE 30

Sodium 7-[(Z)-2-(2-aminothiazol-4-yl)-2-hydroxyiminoacetamido]-3-[(Z)-3-(N,N-dimethylcarbamoyloxy)-1-propenyl]-3-cephem-4-carboxylate

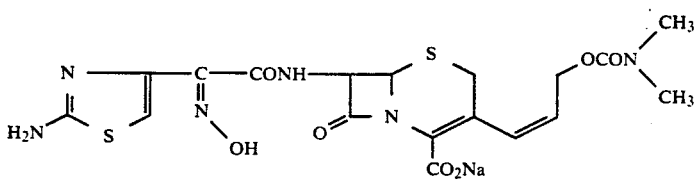

Trifluoroacetic acid (30 ml) was added dropwise under ice cooling to a solution of the compound (3.5 g; 3.179 mmol) of Preparation Example 19 in anisole (28 ml), followed by stirring at room temperature for 2 hours. After the reaction mixture was concentrated under reduced pressure, the concentrate was added dropwise to a mixed solvent of IPE (isopropyl ether) (60 ml) and n-hexane (180 ml). Precipitated crystals were collected by filtration. Those crystals were added to 90% formic acid (30 ml), followed by stirring at room temperature for 3 hours. After the solvent was distilled off under reduced pressure, the residue was triturated in IPE and crystals were collected by filtration. The crystals were dissolved in methanol (60 ml) and sodium acetate (782 mg; 9.533 mmol) was added. The solvent was distilled off under reduced pressure. The crude product was triturated in 2-propanol and crude crystals were collected by filtration. The crude crystals were purified by chromatography on an ODS column (8% aq. methanol). The eluate was concentrated under reduced pressure and lyophilized, whereby the title compound (310 mg; 0.598 mmol; 18.8%) was obtained.

NMR (DMSO-d$_6$) δ: 2.83(6 H,s,N(CH$_3$)2), 3.53(2 H,ABq,J=18.0 Hz,CH$_2$), 4.55–4.75(2 H,dm,CH$_2$), 5.02(1 H,d,J=4.7 Hz,CH), 5.15–5.20(1 H,m,=CH—), 5.57(1 H,dd,J=8.2,4.7 Hz,CH), 6.62(1 H,d,J=12.1 Hz,—CH=), 6.65(1 H,s,thiazole-H), 7.09(2 H,s,NH$_2$), 9.37(1 H,d,J=8.2 Hz,CONH).

Mass (m/Z): 518(M+), 519(M+ +1).

EXAMPLE 31

Pivaloyloxymethyl 7-[(Z)-2-(2-aminothiazol-4-yl)-2-hydroxyiminoacetamido]-3-[(Z)-3-(N,N-dimethylcarbamoyloxy)-1-propenyl]-3-cephem-4-carboxylate

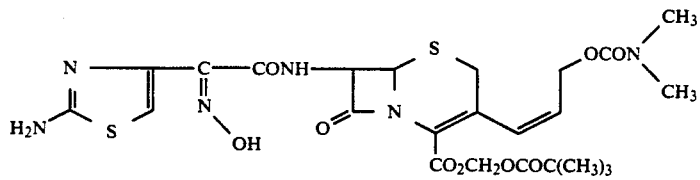

A solution of iodomethyl pivalate (56 mg; 0.231 mmol) in dry dimethylformaldehyde (0.5 ml) was added dropwise under ice cooling to a solution of the compound (120 mg; 0.232 mmol) of Example 30 in dry dimethylformamide (2 ml). The resulting mixture was stirred for 30 minutes. Ethyl acetate was added to the reaction mixture. The organic layer was washed with water and then with saturated saline. Magnesium sulfate was added to the solution to dry the same. The solution was concentrated under reduced pressure. The concentrate was added dropwise to n-hexane (50 ml). Precipitated crystals were collected by filtration and then dried, whereby the title compound (98 mg; 0.161 mmol; 69.2%) was obtained.

NMR (DMSO-d6) δ: 1.15(9 H,s,C(CH3)3), 2.81(6 H,s,N(CH3)2), 3.61(2 H,ABq,J=18.0 Hz,CH2), 4.40–4.60(2 H,dm,CH2), 5.24(1 H,d,J=5.1 Hz,CH), 5.65–5.70(1 H,m,=CH—), 5.80(2 H,ABq,J=6.0 Hz,CO2CH2O), 5.80–5.85(1 H,m,CH), 6.28(1 H,d,J=11.7 Hz,—CH=), 6.66(1 H,s,thiazole-H), 7.11(2 H,s,NH2), 9.46(1 H,d,J=8.1 Hz,CONH), 11.29(1 H,s,=N—OH).

Mass (m/Z): 610(M+), 611(M++1).

Under ice cooling, 7N-HCl/diethyl ether solution (0.04 ml) was added dropwise to a solution of the title compound (80 mg; 0.131 mmol) in ethyl acetate (2 ml). The resulting mixture was stirred for 20 minutes. The solvent was distilled off under reduced pressure and the residue was dissolved in tetrahydrofuran (2 ml). The solution was added dropwise to n-hexane (20 ml). Precipitated crystals were collected by filtration and then dried, whereby the hydrochloride of the title compound (42 mg; 0.065 mmol; 49.6%) was obtained.

EXAMPLE 32

Sodium 7-[(Z)-2-(2-aminothiazol-4-yl)-2-hydroxyiminoacetamido]-3-[(Z)-3-(1-morphorinylcarbonyloxy)-1-propenyl]-3-cephem-4-carboxylate

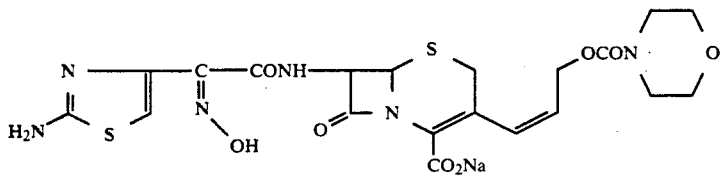

(1) Synthesis of 4-methoxyphenylmethyl 7-[(Z)-2-(2-trithylaminothiazol-4-yl)-2-trithyloxyiminoacetamido]-3-[(Z)-3-(1-morphorinylcarbonyloxy)-1-propenyl]-3-cepham-4-carboxylate

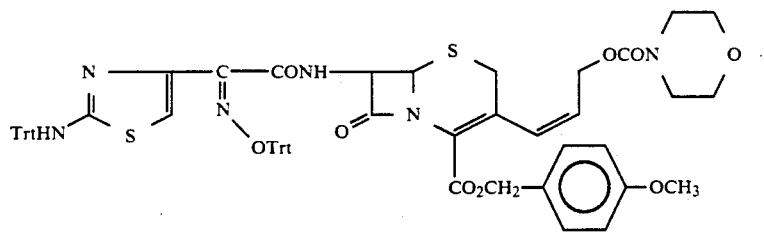

A solution of 4-methoxyphenylmethyl 7-[(Z)-2-(2-trithylaminothiazol-4-yl)-2-trithyloxyiminoacetamido]-3-(triphenylphosphoranylidene)methyl-3-cepham-4-carboxylate (24 g; 17.46 mmol) and 1-morphonylcarbonyloxyacetaldehyde (4 g; 23.12 mmol) in dichloromethane (100 ml) was stirred at room temperature for 16 hours. After the solvent was distilled off under reduced pressure, the residue was purified by chromatography on a silica gel column (n-hexane:ethyl acetate =1:1), whereby the title compound (3.4 g; 2.98 mmol; 17.1%) was obtained.

(2) Synthesis of sodium 7-[(Z)-2-(2-aminothiazol-4-yl)-2-hydroxyiminoacetamido]-3-[(Z)-3-(1-morphorinylcarbonyloxy)-1-propenyl]-3-cepham-4-carboxylate

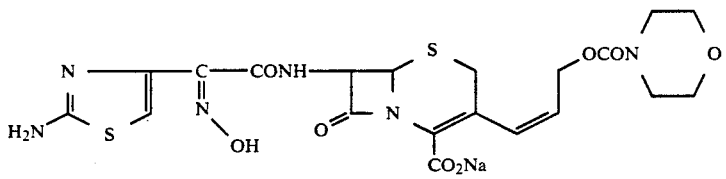

To a solution of 4-methoxyphenylmethyl 7-[(Z)-2-(2-trithylaminothiazol-4-yl)-2-trimethyloxyiminoacetamido]-3-[(Z)-3-(1-morphorinylcarbonyloxy)-1-propenyl]-3-cepham-4-carboxylate (3.0 g; 2.63 mmol), which had been obtained in the step (1), in anisole (22 ml), trifluoroacetic acid (24 ml) was added dropwise under ice-cooling. The resulting mixture was stirred at room temperature for 2 hours. After the mixture was concentrated under reduced pressure, the resulting concentrate was added dropwise to a mixed solution of isopropyl ether (60 ml) and n-hexane (180 ml). Precipitated crystals were collected by filtration. Those crystals were added to 90% formic acid (30 ml), followed by stirring at room temperature for 3 hours. The solvent was distilled off under reduced pressure. The residue was triturated with isopropyl ether and crystals were collected by filtration. Those crystals were dissolved in methanol (60 ml), followed by the addition of sodium acetate (647 mg; 7.89 mmol). Under reduced pressure, the solvent was distilled off. The resulting crude product was triturated with 2-propanol, followed by the collection of crude crystals by filtration. The crude crystals were purified by ODS column chromatography (8% aqueous methanol). The eluate was concentrated under reduced pressure and then lyophilized, whereby the title compound (300 mg; 0.54 mmol; 20.4 %) was obtained.

NMR (DMSO-d$_6$) δ: 3.15 (4 H,s,CH$_2$x2), 3.55(4 H,m,CH$_2$x2), 3.68(2 H,ABq,J=18.0 Hz,CH$_2$), 4.60–4.75(2 H,dm,CH$_2$), 5.06(1 H,d,J=4.9 Hz,CH), 5.30–5.35(1 H,m,=CH—), 5.62(1 H,dd,J=8.0,4.9 Hz,CH), 6.62(1 H,d,J=10.2 Hz, —CH=), 6.63(1 H,s,thiazole-H), 7.14(2 H,s,NH$_2$), 9.44(1 H,d,J=8.0 Hz,CONH).

Mass (m/Z): 560(M-), 561(M++1).

PREPARATION EXAMPLE 20

4-Methoxyphenylmethyl 7-[(Z)-2-(2-tritylaminothiazol-4-yl)-2-trityloxyiminoacetamido]-3-[(Z)-3-tert-butyldimethylsilyloxy-1-propenyl]-3-cephem-4-carboxylate

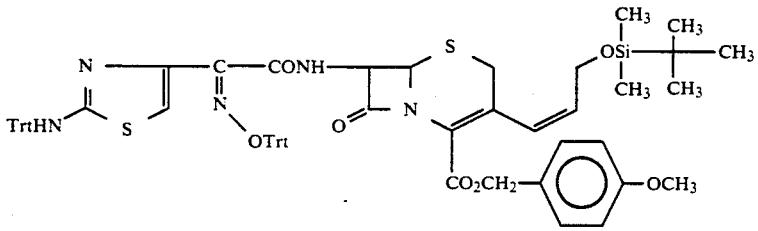

A solution of 4-methoxyphenylmethyl 7-[(Z)-2-(2-tritylaminothiazol-4-yl)-2-trityloxyiminoacetamido]-3-(triphenylphosphoranylidene)methyl-3-cephem-4-carboxylate (9.07 g; 7.27 mmol) and t-butyldimethylsilyloxyacetaldehyde (1.8 g; 10.34 mmol) in dichloromethane (100 ml) was stirred at room temperature for 16 hours. After the solvent was distilled off under reduced pressure, the residue was purified by chromatography on a silica gel column (n-hexane:ethyl acetate=2.5:1) whereby the title compound (4.99 g; 4.36 mmol; 60.0%) was obtained.

NMR (CDCl$_3$) δ: 0.20(6 H,bs,CH$_3$x2), 1.04(9 H,bs,C(CH$_3$)$_3$), 3.40–3.60(2 H,m,CH$_2$), 3.88(3 H,s,OCH$_3$), 4.20–4.40(2 H,m,-CH$_2$OSi), 5.00–5.20(1 H,m,CH), 5.28(2 H,s,CO$_2$CH$_2$), 5.60–6.40(3 H,m,CH,-CH=CH—), 6.56(1 H,s,thiazole-H), 6.90–7.80(34 H,m).

PREPARATION EXAMPLE 21

4-Methoxyphenylmethyl 7-[(Z)-2-(2-tritylaminothiazol-4-yl)-2-trityloxyiminoacetamido]-3-[(Z)-3-hydroxy-1-propenyl]-3-cephem-4-carboxylate

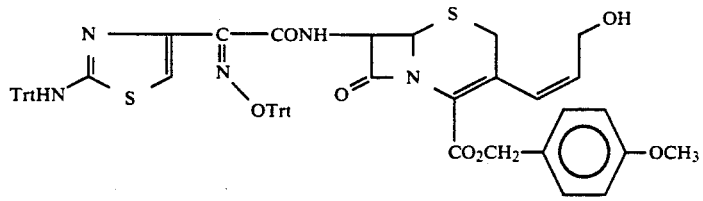

1N-Hydrochloric acid (10 ml) was added to a solution of the compound (4.99 g; 4.36 mmol), which had been obtained in Preparation Example 20, in acetone (50 ml), followed by stirring at room temperature for 2 hours. After the acetone was distilled off under reduced pressure, water was added, followed by extraction with ethyl acetate. The extract was washed with water and then with saturated saline. Magnesium sulfate was added to dry the extract. The solvent was distilled off under reduced pressure and the residue was purified by chromatography on a silica gel column (n-hexane:ethyl acetate =1:1), whereby the title compound (2.2 g; 2.14 mmol; 49.0%) was obtained.

NMR (CDCl$_3$) δ: 3.24(2 H,ABq,J=18.0 Hz,CH$_2$), 3.80(3 H,s,OCH$_3$), 3.90–4.10(2 H,m,—CH$_2$O—), 5.02(1 H,d,J=4.8 Hz,CH), 5.16(2 H,s,CO$_2$CH$_2$—), 5.60–6.00(2 H,m,CH,=CH—), 6.14(1 H,d,J=12.5 Hz,—CH=), 6.42(1 H,s,thiazole-H), 6.80–7.70(34 H,m).

Mass (m/z): 1029(M+), 1030(M++1).

PREPARATION EXAMPLE 22

4-Methoxyphenylmethyl 7-[(Z)-2-(2-tritylaminothiazol-4-yl)-2-trityloxyiminoacetamido]-3-[(Z)-3-(N-methylcarbamoyloxy)-1-propenyl]-3-cephem-4-carboxylate

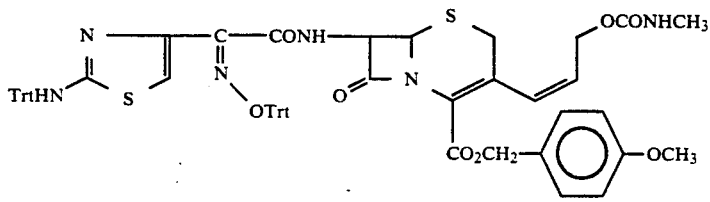

To a solution of the compound (2 g; 1.944 mmol), which had been obtained in Preparation Example 21, in dry tetrahydrofuran (40 ml), methyl isocyanate (887 mg; 15.548 mmol) and triethylamine (catalytic amount) were added. The resulting mixture was heated at 60° C.

for 4 hours. The solvent was distilled off under reduced pressure and the residue was purified by chromatography on a silica gel column (dichloromethane:acetone=95:5), whereby the title compound (1 g; 0.920 mmol; 47.3%) was obtained.

NMR (CDCl₃) δ: 2 66(3 H,d,J=4.4 Hz,NH—CH₃), 3.25(2 H,ABq,J=18.0 Hz,CH₂), 3.74(3 H,s,OCH₃), 4.30-4.70(2 H,m,CH₂), 5.02(1 H,d,J=4.8 Hz,CH), 5.10(2 H,s,CO₂ CH₂), 5.55-5.80(1 H,m,=CH—), 5.96(1 H,dd,J=8.1,4.8 Hz,CH), 6.18(1 H,d,J=11.8 Hz,—CH=), 6.40(1 H,s,thiazole-H), 6.80-7.60(34 H,m).

PREPARATION EXAMPLE 23

4-Methoxyphenylmethyl 7-[(Z)-2-(2-tritylaminothiazol-4-yl)-2-methoxyiminoacetamido]-3-.(Z)-3-tert-butyldimethylsilyloxy-1-propenyl]-3-cephem-4-carboxylate

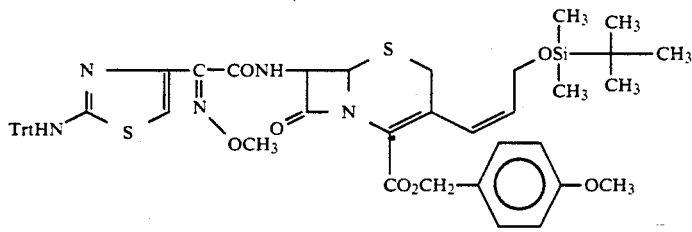

A solution of 4-methoxyphenylmethyl 7-[(Z)-2-(2-tritylaminothiazol-4-yl)-2-methoxyiminoacetamido]-3-(triphenylphosphoranylidene)methyl-3-cephem-4-carboxylate (10.5 g; 10.30 mmol) and t-butyldimethylsilyloxyacetaldehyde (2.58 g; 14.83 mmol) in dichloromethane (100 ml) was stirred at room temperature for 16 hours. After the solvent was distilled off under reduced pressure, the residue was purified by chromatography on a silica gel column (n-hexane:ethyl acetate=2.5:1) whereby the title compound (4.30 q; 4.72 mmol; 45.8%) was obtained.

NMR (CDCl₃) δ: 0.20(6 H,br-s,CH₃x2), 1.04(9 H,br-s,C(CH₃)3), 3.55-3.80(2 H,m,CH₂), 3.92(3 H,S,OCH₃), 4.10(3 H,s,OCH₃), 4.10-4.30(2 H,m,-CH₂OSi), 5.10-5.30(3 H,m,CH,CO₂CH₂), 5.70-6.40(3 H,m,CH,-CH=CH—), 6.60-7.60(20 H,m,thiazole-H).

PREPARATION EXAMPLE 24

4-Methoxyphenylmethyl 7-[(Z)-2-(2-tritylaminothiazol-4-yl)-2-methoxyiminoacetamido]-3-(Z)-3-hydroxy-1-propenyl]-3-cephem-4-carboxylate

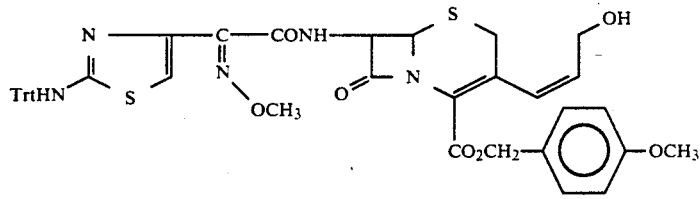

1N-Hydrochloric acid (10 ml) was added to a solution of the compound (4.30 g; 4.72 mmol), which had been obtained in Preparation Example 23, in acetone (50 ml), followed by stirring at room temperature for 2 hours. After the acetone was distilled off under reduced pressure, water was added, followed by extraction with ethyl acetate. The extract was washed with water and then with saturated saline. Magnesium sulfate was added to dry the extract. The solvent was distilled off under reduced pressure and the residue was purified by chromatography on a silica gel column (n-hexane:ethyl acetate=2:1), whereby the title compound (2.1 g; 2.62 mmol; 55.5%) was obtained.

NMR (CDCl₃) δ: 3.34(2 H,ABq,J=18.0 Hz,CH₂), 3.72(3 H,s,OCH₃), 4.00(3 H,s,OCH₃), 3.85-4.15(2 H,m,—CH₂O—), 5.00(1 H,d,J=5.1 Hz,CH), 5.08(2 H,s,CO₂CH₂), 5.55-5.95(2 H,m,CH,=CH—), 6.10(1 H,d,J=11.5,—CH=), 6.56(1 H,s,thiazole-H), 6.70-7.40(19 H,m).

PREPARATION EXAMPLE 25

4-Methoxyphenylmethyl 7 [(Z) 2 (2 tritylaminothiazol-4-yl)-2-methoxyiminoacetamido]-3-[(Z)-3-(N-methylcarbamoyloxy)-1-propenyl]-3-cephem-4-carboxylate

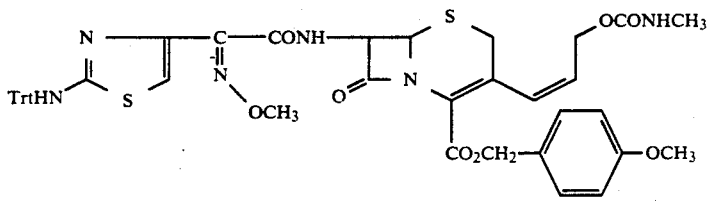

To a solution of the compound (2.8 g; 3.493 mmol), which had been obtained in Preparation Example 24, in dry tetrahydrofuran (40 ml), methyl isocyanate (2 g; 35.057 mmol) and triethylamine (catalytic amount) were added. The resulting mixture was heated at 60° C.

for 7 hours. The solvent was distilled off under reduced pressure and the residue was purified by chromatography on a silica gel column (dichloromethane:acetone =95:5), whereby the title compound (1.54 q 1.795 mmol: 51.4%) was obtained.

PREPARATION EXAMPLE 26

4-Methoxyphenylmethyl 7-[(Z)-2-(2-tritylaminothiazōl-4-yl)-2-trityloxyiminoacetamido]-3-[(Z)-3-(N-isopropylcarbamoyloxy)-1-propenyl]-3-cephem-4-carboxylate

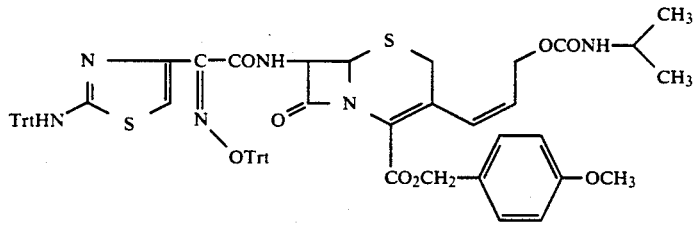

To a solution of the compound (2.8 g; 2.721 mmol), which had been obtained in Preparation Example 21, in dry tetrahydrofuran (40 ml), isopropyl isocyanate (520 mg; 6.110 mmol) and triethylamine (catalytic amount) were added. The resulting mixture was heated at 60° C. for 6 hours. The solvent was distilled off under reduced pressure and the residue was purified by chromatography on a silica gel column (dichloromethane:acetone=20:1), whereby the title compound (1.9 g; 1.706 mmol; 62.7%) was obtained.

NMR (CDCl$_3$) δ: 1.12(6 H,t,J=5.8 Hz,CH(CH$_3$)2), 3.28(2 H,ABq,J=18.0 Hz,CH$_2$), 3.60–3 80(1 H,m,CH(CH$_3$)2), 3.76(3 H,s,OCH$_3$), 4.25–4.60(2 H,m,CH$_2$), 5.04(1 H,d,J=4.8 Hz,CH), 5.14(2 H,s,CO$_2$CH$_2$—), 5.50–5.80(1 H,m,=CH—), 5.98(1 H,dd,J=8.1,4.8 Hz,CH), 6.26(1 H,d,J=11.5 Hz,—CH=), 6.40(1 H,s,thiazole-H), 6.70–7.40(34 H,m).

PREPARATION EXAMPLE 27

4-Methoxyphenylmethyl 7-(Z)-2-(2-tritylaminothiazol-4-yl)-2-trityloxyiminoacetamido]-3-[(Z)-3-(N-ethylcarbamoyloxy)-1-propenyl]-3-cephem-4-carboxylate

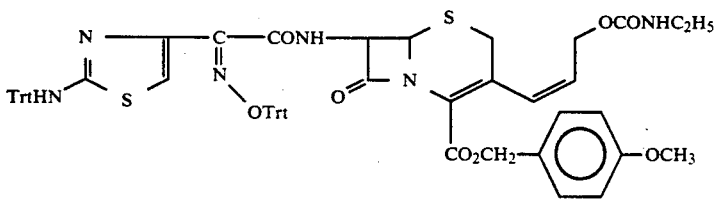

To a solution of the compound (2 g; 1.944 mmol), which had been obtained in Preparation Example 21, in dry tetrahydrofuran (40 ml), ethyl isocyanate (1.1 g; 15.5 mmol) and triethylamine (catalytic amount) were added. The resulting mixture was heated at 60° C. for 4 hours. The solvent was distilled off under reduced pressure and the residue was purified by chromatography on a silica gel column (dichloromethane:acetone=95:5), whereby the title compound (1.1 g; 1.0 mmol; 51%) was obtained.

NMR (CDCl$_3$) δ: 1.00(3 H,t,J=7 Hz,CH$_2$CH$_3$), 3.10(2 H,m,CH$_2$CH$_3$), 3.20–3.60(2 H,m,CH$_2$), 3.77(3 H,s,OCH$_3$), 4.40–4.80(2 H,m,CH$_2$), 5.07(1 H,d,J=5 Hz,CH), 5.14(2 H,s,—CO$_2$CH$_2$—), 5.55–6.00(2 H,m,CH,=CH—), 6.22(1 H,d,J=12 Hz,—CH=), 6.39(1 H,s,thiazole-H), 6.80–7.60(34 H,m).

PREPARATION EXAMPLE 28

4-Methoxyphenylmethyl 7-[(Z)-2-(2-tritylaminothiazol-4-yl)-2-trityloxyiminoacetamido]-3-[(Z) -3-(N-(2-chloroethyl)carbamoyloxy)-1-propenyl]-3-cephem-4-carboxylate

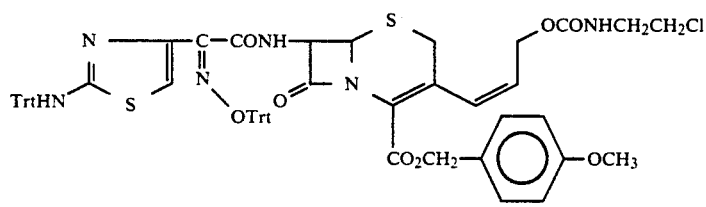

To a solution of the compound (2 g; 1.944 mmol), which had been obtained in Preparation Example 21, in dry tetrahydrofuran (40 ml), 2-chloroethyl isocyanate (1.6 g; 15.2 mmol) and triethylamine (catalytic amount) were added. The resulting mixture was heated at 60° C. for 4 hours. The solvent was distilled off under reduced pressure and the residue was purified by chromatography on a silica gel column (dichloromethane:acetone=95:5), whereby the title compound (0.6 g; 0.53 mmol; 27%) was obtained.

NMR (CDCl$_3$) δ: 3.2–3 7(6 H,m,CH$_2$CH$_2$Cl,CH$_2$), 3.78(3 H,s,OCH$_3$), 4.3–4.6(2 H,m,CH$_2$), 5.05(1 H,d,J=5 Hz,CH), 5.15(2 H,s,CO$_2$CH$_2$), 5.60–6.00(2 H,m,CH,CH=), 6.22(1 H,d,J=12 Hz,CH=), 6.38(1 H,s,thiazole-H), 6.70–7.50(34 H,m).

PREPARATION EXAMPLE 29

4-Methoxyphenylmethyl 7-[(Z)-2-(2-tritylaminothiazol-4-yl)-2-trityloxyiminoacetamido]-3-[(Z)-3-(N-allylcarbamoyloxy)-1-propenyl]-3-cephem-4-carboxylate

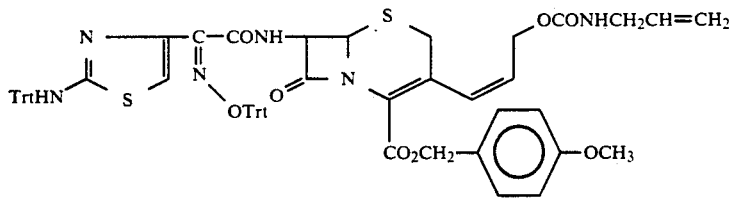

To a solution of the compound (2 g; 1.944 mmol), which had been obtained in Preparation Example 21, in dry tetrahydrofuran (40 ml), allyl isocyanate (1.3 g; 15.6 mmol) and triethylamine (catalytic amount) were added. The resulting mixture was heated at 60° C. for 4 hours. The solvent was distilled off under reduced pressure and the residue was purified by chromatography on a silica gel column (dichloromethane:acetone=95:5), whereby the title compound (1 g; 0.90 mmol; 46%) was obtained.

EXAMPLE 33

Sodium 7-[(Z)-2-(2-aminothiazol-4-yl)-2-hydroxyiminoacetamido]-3-[(Z)-3-(N-methylcarbamoyloxy)-1-propenyl]-3-cephem-4-carboxylate

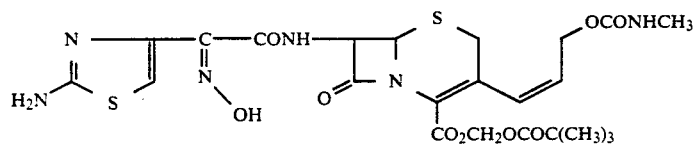

To a solution of the compound (1 g; 0.920 mmol), which had been obtained in Preparation Example 22, in anisole (8 ml), trifluoroacetic acid (10 ml) was added dropwise under ice cooling. The resulting mixture was stirred at room temperature for 2 hours. The mixture was concentrated under reduced pressure and the concentrate was added dropwise to a mixed solvent of isopropyl ether (20 ml) and n-hexane (80 ml). Precipitated crystals were collected by filtration. The crystals were added to 90% formic acid (10 ml), followed by stirring at room temperature for 3 hours. Under reduced pressure, the solvent was distilled off. The residue was triturated in isopropyl ether and crystals were collected by filtration. Those crystals were dissolved in methanol (20 ml), followed by the addition of sodium acetate (226 mg; 2.755 mmol). Under reduced pressure, the solvent was distilled off. The crude product was triturated in 2-propanol and crude crystals were collected by filtration. The crude crystals were purified by ODS chromatography on a silica gel column (5% aqueous methanol). Eluate was concentrated under reduced pressure and then lyophilized, whereby the title compound (250 mg; 0.496 mmol; 53.9%) was obtained.

NMR (DMSO-$d_6$) δ: 2.56(3 H,d,J=4.4 Hz,NH—CH$_3$), 3.52(2 H,ABq,J=16.3 Hz,CH$_2$), 4.50–4.70(2 H,dm,CH$_2$), 5.03(1 H,d,J=4.8 Hz,CH), 5.20–5.30(1 H,m,=CH—), 5.58(1 H,dd,J=8.1,4.8 Hz,CH), 6.63(1 H,d,J=12.1 Hz,—CH=), 6.65(1 H,s,thiazole-H), 6.99(1 H,m,NH—CH$_3$), 7.09(2 H,s,NH$_2$), 9.38(1 H,d,J=8.1 Hz,CONH), 1.20(1 H,br-s,=N—OH).

Mass (m/z): 504(M+), 505(M+ +1).

EXAMPLE 34

Pivaloyloxymethyl 7-(Z)-2-(2-aminothiazol-4-yl)-2-hydroxyiminoacetamido]-3-[(Z)-3-(N-methylcarbamoyloxy-1-propenyl]-3-cephem-4-carboxylate

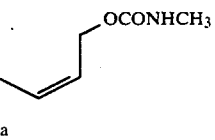

To a solution of the compound (110 mg; 0.218 mmol), which had been obtained in Preparation Example 33, in dry dimethylformamide (3 ml), a solution of iodomethyl pivalate (53 mg; 0.219 mmol) in dry dimethylformamide (0.5 ml) was added dropwise under ice cooling. The resulting mixture was stirred for 30 minutes. Ethyl acetate was added to the reaction mixture. The resulting mixture was washed with water and then with saturated saline. Magnesium sulfate wa added to dry the mixture, followed by concentration under reduced pressure. The concentrate was added dropwise to n-hexane (50 ml). Precipitated crystals were collected by filtration and then dried, whereby the title compound (86 mg; 0.144 mmol; 66.2%) was obtained.

NMR (DMSO-$d_6$) δ: 1.16(9 H,s,C(CH$_3$)3), 2.55(3 H,d,J=4.4 Hz,NH—CH$_3$), 3.60(2 H,ABq,J=17.8 Hz,CH$_2$),4.35–4.55(2 H,dm,CH$_2$), 5.24(1 H,d,J=4.8 Hz,CH), 5.60–5.70(1 H,m,=CH—), 5.75–5.85(3 H,m,CH,CH$_2$), 6.27(1 H,d,J=11.7 Hz,—CH=), 6.66(1 H,s,thiazole-H), 6.98(1 H,m,NH—CH$_3$), 7.12(2 H,s,NH$_2$), 9.47(1 H,d,J=8.1 Hz,CONH), 11.30(1 H,s,=N—OH).

Mass (m/z): 596(M+), 597(M+ +1).

Further, 7N-HCl/diethyl ether solution (0.04 ml) was added dropwise under ice cooling to a solution of the title compound (44 mg; 0.074 mmol) in ethyl acetate (2 ml), followed by stirred for 20 minutes. Precipitated crystals were collected by filtration and then dried, whereby the hydrochloride (40 mg; 0.063 mmol; 85.4%) of the title compound was obtained.

EXAMPLE 35

2-Ethylbutanoyloxymethyl 7-[(Z)-2-(2-aminothiazol-4-yl)-2-hydroxyiminoacetamido]-3-[(Z)-3-(N-methylcarbamoyloxy)-1-propenyl]-3-cephem-4-carboxylate

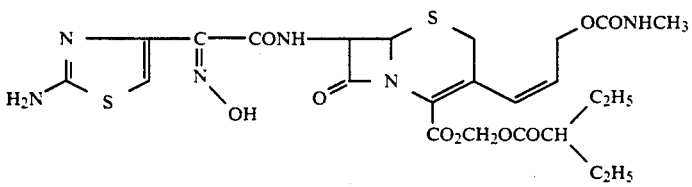

To a solution of the compound (120 mg; 0.238 mmol), which had been obtained in Example 33, in dry dimethylformamide (3 ml), a solution of iodomethyl 2-ethylbutyrate (61 mg; 0.238 mmol) in dry dimethylformamide (0.5 ml) was added dropwise under ice cooling. The resulting mixture was stirred for 30 minutes. Ethyl acetate was added to the reaction mixture. The resulting mixture was washed with water and then with saturated saline. Magnesium sulfate was added to dry the mixture, followed by concentration under reduced pressure. The concentrate was added dropwise to n-hexane (50 ml). Precipitated crystals were collected by filtration and then dried, whereby the title compound (102 mg; 0.167 mmol; 70.3%) was obtained.

NMR (DMSO-$d_6$) δ: 0.80–0.90(6 H,m,$CH_2CH_3$x2), 1.45–1.60(4 H,m,$CH_2CH_3$x2), 2.20–2.30(1 H,m,$CH(C_2H_5)_2$), 2.56(3 H,d,J=4.6 Hz,$NHCH_3$), 3.61(2 H,ABq,J=18.0 Hz,$CH_2$), 4.35–4.55(2 H,dm,$CH_2$), 5.24(1 H,d,J=4.8 Hz,CH), 5.60–5.70(1 H,m,=CH—), 5.80–5.85(3 H,m,$CO_2CH_2$,CH), 6.28(1 H,d,J=11.7 HZ,—CH=), 6.66(1 H,s,thiazole-H), 6.99(1 H,m $NHCH_3$), 7.12(2 H,s,$NH_2$), 9.47(1 H,d,J=8.4 Hz,CONH), 11.30(1 H,s,=N—OH).

Mass (m/z): 610(M+), 611(M+ +1).

Further, 7N-HCl/diethyl ether solution (0.04 ml) was added dropwise under ice cooling to a solution of the title compound (44 mg; 0.072 mmol) in ethyl acetate (2 ml), followed by stirring for 20 minutes. n-Hexane (20 ml) was added to the reaction mixture. Precipitated crystals were collected by filtration and then dried, whereby the hydrochloride (38 mg; 0.059 mmol; 81.6%) of the title compound was obtained.

EXAMPLE 36

1-(Pivaloyloxy)ethyl 7-[(Z)-2-(2-aminothiazol-4-yl)-2-hydroxyiminoacetamido]-3-[(Z)-3-N-methylcarbamoyloxy-1-propenyl]3-cephem-4-carboxylate

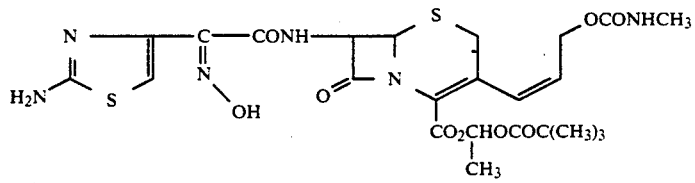

To a solution of the compound (155 mg; 0.308 mmol), which had been obtained in Example 33, in dry dimethylformamide (2.5 ml), a solution of 1-iodoethyl pivalate (94 mg; 0.367 mmol) in dry dimethylformamide (0.5 ml) was added dropwise under ice cooling. The resulting mixture was stirred for 30 minutes. Ethyl acetate was added to the reaction mixture. The resulting mixture was washed with water and then with saturated saline. Magnesium sulfate was added to dry the mixture, followed by concentration under reduced pressure. The concentrate was added dropwise to n-hexane (50 ml). Precipitated crystals were collected by filtration and then dried, whereby the title compound (46 mg; 0.075 mmol; 24.5%) was obtained.

NMR (DMSO-$d_6$) δ: 1.13 and 1.15(9 H,s,$C(CH_3)_3$), 1.43,1.45(3 H,d,J=5.5 Hz,$OCH(CH_3)O$), 2.55(3 H,d,J=4.8 Hz,$NHCH_3$), 3.59,3.60(2 H,ABq,J=18.0 Hz,$CH_2$), 4.35–4.55(2 H,dm,$CH_2$), 5.23,5.25(1 H,d,J=5.2 Hz,CH), 5.55–5.70(1 H,m,=CH—), 5.85–5.90(1 H,m,CH), 6.23,6.26(1 H,d,J=11.0 Hz,—CH=), 6.65,6.66(1 H,s,thiazole-H), 6.81,6.88(1 H,q,J=5.5 Hz,$OCH(CH_3)O$), 6.98(1 H,m,$NHCH_3$), 7.11(2 H,s,$NH_2$), 9.46(1 H,d,J=8.2 Hz,CONH), 11.29(1 H,s,=N—OH).

Mass (m/z): 610(M+), 611(M+ +1).

Further, 7N-HCl/diethyl ether solution (0.04 ml) was added dropwise under ice cooling to a solution of the title compound (40 mg; 0.066 mmol) in ethyl acetate (2 ml), followed by stirring for 20 minutes. The solvent was distilled off under reduced pressure and the residue was dissolved in tetrahydrofuran (2 ml). The resulting solution was added dropwise to n-hexane (20 ml). Precipitated crystals were collected by filtration and then dried, whereby the hydrochloride (38 mg; 0.059 mmol; 89.0%) of the title compound was obtained.

EXAMPLE 37

2,2-Dimethyl-3-methoxypropenyloxymethyl 7-[(Z)-2(2-aminothiazol-4-yl)-2-hydroxyiminoacetamido]-3-[(Z)-3-(N-methylcarbamoyloxy)-1-propenyl]-3-cephem-4-carboxylate

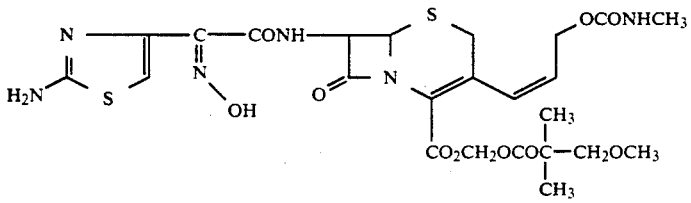

To a solution of the compound (148 mg; 0.294 mmol), which had been obtained in Example 33, in dry dimethylformamide (2.5 ml), a solution of iodomethyl 2,2-dimethyl-3-methoxypropionate (80 mg; 0.294 mmol) in dry dimethylformamide (0.5 ml) was added dropwise under ice cooling. The resulting mixture was stirred for 30 minutes. Ethyl acetate was added to the reaction mixture. The resulting mixture was washed with water and then with saturated saline. Magnesium sulfate was added to dry the mixture, followed by concentration under reduced pressure. The concentrate was added dropwise to n-hexane (50 ml). Precipitated crystals were collected by filtration and then dried, whereby the title compound (100 mg; 0.160 mmol; 54.3%) was obtained.

NMR (DMSO-$d_6$) δ: 1.12(6 H,s,OCOC($CH_3$)$_2$C-$H_2$—), 2.55(3 H,d,J=4.4 Hz,NH$CH_3$), 3.22(3 H,s,O$CH_3$), 3.33(2 H,s,$CH_2$O$CH_3$), 3.56(2 H,ABq,J=18.0 Hz,$CH_2$), 4.35-4.55(2 H,dm,$CH_2$), 5.24(1 H,d,J=5.1 Hz,CH), 5.60-5.70(1 H,m,=CH—), 5.80(2 H,ABq,J=6.0 Hz,O$CH_2$OCO), 5.80-5.90(1 H,m,CH), 6.28(1 H,d,J=11.7 Hz,—CH=), 6.66(1 H,s,thiazole-H), 6.99(1 H,m,NH$CH_3$), 7.12(2 H,s,$NH_2$), 9.47(1 H,d,J=8.1 Hz,CONH), 11.30(1 H,s,=N—OH).

Mass (m/z): 626($M^+$), 627($M^+ + 1$).

Further, 7N-HCl/diethyl ether solution (0.04 ml) was added dropwise under ice cooling to a solution of the title compound (40 mg; 0.064 mmol) in ethyl acetate (2 ml), followed by stirring for 20 minutes. The solvent was distilled off under reduced pressure and the residue was dissolved in tetrahydrofuran (2 ml). The resulting solution was added dropwise to n-hexane (20 ml). Precipitated crystals were collected by filtration and then dried, whereby the hydrochloride (38 mg; 0.057 mmol; 89.5%) of the title compound was obtained.

EXAMPLE 38

Sodium 7-(Z)-2-(2-aminothiazol-4-yl)-2-methoxyiminoacetamido]-3-[(Z)-3-(N-methylcarbamoyloxy)-1-propenyl]-3-cephem-4-carboxylate

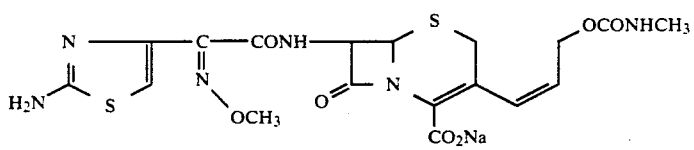

To a solution of the compound (1.54 g; 1.795 mmol), which had been obtained in Preparation Example 25, in anisole (16 ml), trifluoroacetic acid (16 ml) was added dropwise under ice cooling. The resulting mixture was stirred at room temperature for 2 hours. The reaction mixture was concentrated under reduced pressure and the resulting concentrate was added dropwise to a mixed solvent of isopropyl ether (40 ml) and n-hexane (160 ml). Precipitated crystals were collected by filtration. The crystals were added to 90% formic acid (20 ml), followed by stirring at room temperature for 3 hours. Under reduced pressure, the solvent was distilled off. The residue was triturated in isopropyl ether and crystals were collected by filtration. Those crystals were dissolved in methanol (40 ml), followed by the addition of sodium acetate (442 mg; 5.388 mmol). Under reduced pressure, the solvent was distilled off. The crude product was triturated in 2-propanol and crude crystals were collected by filtration. The crude crystals were purified by ODS column chromatography (5% aqueous methanol). Eluate was concentrated under reduced pressure and then lyophilized, whereby the title compound (200 mg; 0.386 mmol; 21.5%) was obtained.

NMR (DMSO-$d_6$) δ: 2.56(3 H,d,J=4.4 Hz,NH$CH_3$), 3.53(2 H,ABq,J=16.5 Hz,$CH_2$), 3.84(3 H,s,O$CH_3$), 4.50-4.70(2 H,dm,$CH_2$), 5.03(1 H,d,J=4.8 Hz,CH), 5.20-5.30(1 H,m,=CH—), 5.55(1 H,dd,J=8.0,4.8 Hz,CH), 6.62(1 H,d,J=12.1 Hz,—CH=), 6.74(1 H,s,thiazole-H), 7.00(1 H,m,NH—$CH_3$), 7.19(2 H,s,$NH_2$), 9.51(1 H,d,J=8.0 Hz,CONH).

Mass (m/Z): 518($M+$), 519($M^+ + 1$).

EXAMPLE 39

Pivaloyloxymethyl 7-[(Z)-2-(2-aminothiazol-4-yl) 2-methoxyiminoacetamido]-3-[(Z) 3-(N-methylcarbamoyloxy)-1-propenyl]-3-cephem-4-carboxylate

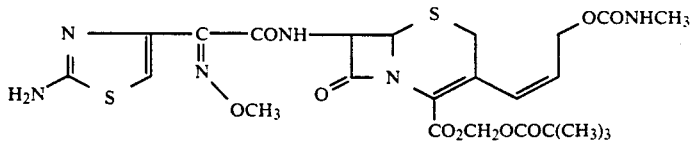

To a solution of the compound (120 mg; 0.232 mmol), which had been obtained in Example 38, in dry dimethylformamide (2 ml), a solution of iodomethyl pivalate (58 mg; 0.240 mmol) in dry dimethylformamide (0.5 ml) was added dropwise under ice cooling. The resulting mixture was stirred for 30 minutes. Ethyl acetate was added to the reaction mixture. The resulting mixture was washed with water and then with saturated saline. Magnesium sulfate was added to dry the mixture. The solution was concentrated under reduced pressure and the concentrate was added dropwise to n-hexane (50 ml). Precipitated crystals were collected by filtration and then dried, whereby the title compound (80 mg; 0.131 mmol; 56.5%) was obtained.

NMR (DMSO-$d_6$) δ: 1.16(9 H,s,C(CH$_3$)3), 2.55(3 H,d,J=4.4 Hz,NHCH$_3$), 3.62(2 H,ABq,J=17.8 Hz,CH$_2$), 3.84(3 H,s,OCH$_3$), 4.35–4.55(2 H,dm,CH$_2$), 5.25(1 H,d,J=4.8 Hz,CH), 5.60–5.70(1 H,m,=CH—), 5.75–5.85(3 H,m,CH,CO$_2$CH$_2$O), 6.27(1 H,d,J=11.7 Hz,—CH=), 6.75(1 H,s,thiazole-H), 6.99(1 H,m,NHCH$_3$), 7.20(2 H,s,NH$_2$), 9.61(1 H,d,J=8.1 Hz,CONH).

Mass (m/z): 610(M+), 611(M++1).

Further, 7N-HCl/diethyl ether solution (0.04 ml) was added dropwise under ice cooling to a solution of the title compound (40 mg 0.066 mmol) in ethyl acetate solution (2 ml), followed by stirring for 20 minutes. The solvent was distilled off under reduced pressure and the residue was dissolved in tetrahydrofuran (2 ml). The resulting solution was added dropwise to n-hexane (20 ml). Precipitated crystals were collected by filtration and then dried, whereby the hydrochloride (38 mg; 0.059 mmol; 89.0%) of the title compound was obtained.

dropwise under ice cooling. The resulting mixture was stirred at room temperature for 2 hours. The reaction mixture was concentrated under reduced pressure and the concentrate was added dropwise to a mixed solvent of isopropyl ether (40 ml) and n-hexane (160 ml). Precipitated crystals were collected by filtration. The crystals were added to 90% formic acid, followed by stirring at room temperature for 3 hours. Under reduced pressure, the solvent was distilled off. The residue was triturated in isopropyl ether and crystals were collected by filtration. Those crystals were dissolved in methanol (40 ml), followed by the addition of sodium acetate (420 mg; 5.120 mmol). Under reduced pressure, the solvent was distilled off. The crude product was triturated in 2-propanol and crude crystals were collected by filtration. The crude crystals were purified by ODS column chromatography (8% aqueous methanol). Eluate was concentrated under reduced pressure and then lyophilized, whereby the title compound (400 mg; 0.751 mmol; 44.0%) was obtained.

NMR (DMSO-$d_6$) δ: 1.04(6 H,d,J=6.6 Hz,C(CH$_3$)$_3$), 3.53(2 H,ABq,J=16.5 Hz,CH$_2$), 3.55–3.65(1 H,m,CH(CH$_3$)$_2$), 4.50–4.70(2 H,dm,CH$_2$), 5.05(1 H,m,CH), 5.25–5.35(1 H,m,=CH—), 5.60(1 H,bs,CH), 6.64(1 H,d,J=11.5 Hz,—CH=), 6.66(1 H,s,thiazole-H), 7.03(1 H,m,NHCH(CH$_3$)2), 7.10(2 H,s,NH$_2$), 9.44(1 H,bs,CONH).

Mass (m/z): 532(M+), 533(M++1).

EXAMPLE 41

Pivaloyloxymethyl 7-[(Z)-2-(2-aminothiazol-4-yl)-2-hydroxyiminoacetamido]-3-[(Z)-3-(N-isopropylcarbamoyloxy)-1-propenyl]-3-cephem-4-carboxylate

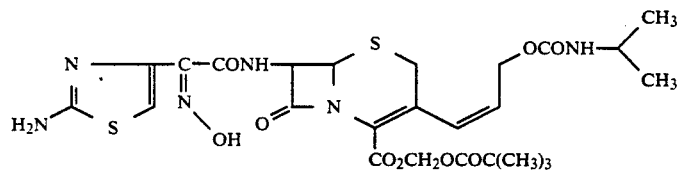

To a solution of the compound (120 mg; 0.225 mmol), which had been obtained in Example 40, in dry dimethylformamide (2 ml), a solution of iodomethyl pivalate (55 mg; 0.227 mmol) in dry dimethylformamide (0.5 ml) was added dropwise under ice cooling. The resulting mixture was stirred for 30 minutes. Ethyl acetate was

EXAMPLE 40

Sodium 7-[(Z)-2-(2-aminothiazol-4-yl)-2-hydroxyiminoacetamido]-3-[(Z)-3-(N-isopropylcarbamoyloxy)-1-propenyl]-3-cephem-4-carboxylate

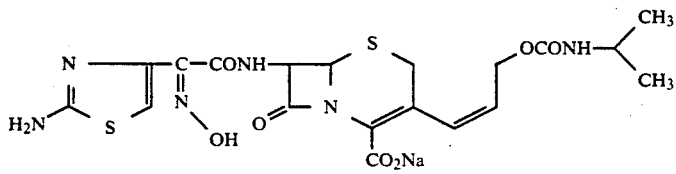

To a solution of the compound (1.9 g; 1.706 mmol), which had been obtained in Preparation Example 26, in anisole (16 ml), trifluoroacetic acid (18 ml) was added added to the reaction mixture. The resulting mixture was washed with water and then with saturated saline.

Magnesium sulfate was added to dry the mixture. The mixture was concentrated under reduced pressure and the concentrate was added dropwise to n-hexane (50 ml). Precipitated crystals were collected by filtration and then dried, whereby the title compound (84 mg; 0.134 mmol; 59.8%) was obtained.

NMR (DMSO-d$_6$) δ: 1.04(6 H,d,J=6.8 Hz,CH(CH$_3$)$_2$), 1.15(9 H,s,-C(CH$_3$)$_3$), 3.55-3.65(1 H,m,CH(CH$_3$)$_2$), 3.61(2 H,ABq,J=18.0 Hz,CH$_2$), 4.35-4.55(2 H,dm,CH$_2$), 5.25(1 H,d,J=4.8 Hz,CH), 5.60-5.70(1 H,m,=CH—), 5.75-5.85(3 H,m,CH,CO$_2$C-H$_2$O), 6.27(1 H,d,J=11.5 Hz,—CH=), 6.66(1 H,s,thiazole-H), 7.05(1 H,d,J=7.6 Hz,NHCH—), 7.12(2 H,bs,NH$_2$), 9.47(1 H,d,J=8.2 Hz,CONH).

Mass (m/z): 624(M$^+$), 625(M$^+$+1).

Further, 7N-HCl/diethyl ether solution (0.04 ml) was added dropwise to a solution of the title compound (50 mg; 0.080 mmol) in ethyl acetate (2 ml) under ice cooling, followed by stirring for 20 minutes. The solvent was distilled off under reduced pressure and the residue was dissolved in tetrahydrofuran (2 ml). The resulting solution was added dropwise to n-hexane (20 ml). Precipitated crystals were collected by filtration and then dried, whereby the hydrochloride (44 mg; 0.067 mmol; 83.2%) of the title compound was obtained.

EXAMPLE 42

Sodium 7-[(Z)-2-(2-aminothiazol-4-yl)-2-hydroxyiminoacetamido]-3-[(Z)-3-(N-ethylcarbamoyloxy)-1-propenyl]-3-cephem-4-carboxylate

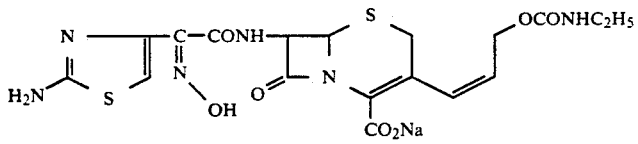

To a solution of the compound (1.1 g; 1.0 mmol), which had been obtained in Preparation Example 27, in anisole (3 ml), trifluoroacetic acid (3 ml) was added dropwise under ice cooling. The resulting mixture was stirred at room temperature for 2 hours. The reaction mixture was concentrated under reduced pressure and the concentrate was added dropwise to a mixed solvent of isopropyl ether (20 ml) and n-hexane (80 ml). Precipitated crystals were collected by filtration. The crystals were added to 90% formic acid (10 ml), followed by stirring at room temperature for 3 hours. Under reduced pressure, the solvent was distilled off. The residue was triturated in isopropyl ether and crystals were collected by filtration. Those crystals were dissolved in methanol (20 ml), followed by the addition of sodium acetate (300 mg; 5 mmol). Under reduced pressure, the solvent was distilled off. The crude product was triturated in 2-propanol and crude crystals were collected by filtration. The crude crystals were purified by ODS column chromatography (7% aqueous methanol). Eluate was concentrated under reduced pressure and then lyophilized, whereby the title compound (210 mg; 0.41 mmol; 41%) was obtained.

NMR (DMSO-d$_6$) δ: 1.00(3 H,t,J=7.0 Hz,CH$_2$CH$_2$), 2.99(2 H,dq,J=12 Hz,7 Hz, CH$_2$CH$_3$), 3.54(2 H,ABq,J=16.5 Hz,CH$_2$), 4.60(2 H,d,ABq,J=5.6 Hz,14 Hz,CH$_2$), 5.04(1 H,d,J=5.1 Hz,CH), 5.20-5.30(1 H,m—CH=), 5.50-5.65(1 H,m,CH), 6.61(1 H,d,J=15.5 Hz,—CH=), 6.65(1 H,s,aminothiazole-H), 7.00(1 H,t,J=7 Hz,NH), 7.09(2 H,s,NH$_2$), 9.42(1 H,m,NH).

EXAMPLE 43

Pivaloyloxymethyl 7-[(Z)-2-(2-aminothiazol-4-yl)-2-hydroxyiminoacetamido]-3-[(Z)-3-(N-ethylcarbamoyloxy)-1-propenyl]-3-cephem-4-carboxylate

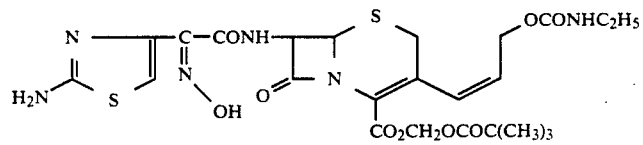

To a solution of the compound (80 mg; 0.15 mmol), which had been obtained in Example 42, in dry dimethylformamide (3 ml), a solution of iodomethyl pivalate (37 mg; 0.16 mmol) in dry dimethylformamide (0.5 ml) was added dropwise under ice cooling. The resulting mixture was stirred for 30 minutes. Ethyl acetate was added to the reaction mixture. The resulting mixture was washed with water and then with saturated saline. Magnesium sulfate was added to dry the mixture. The mixture was concentrated under reduced pressure and the concentrate was added dropwise to n-hexane (50 ml). Precipitated crystals were collected by filtration and then dried, whereby the title compound (60 mg; 0.096 mmol; 65%) was obtained.

NMR (DMSO-d$_6$) δ: 1.00(3 H,t,J=7.0 Hz,CH$_3$), 1.15(9 H,s,C(CH$_3$)$_3$), 2.98(2 H,dq,J=3.3 Hz,7 Hz,CH$_2$CH$_3$), 3.64(2 H,ABq,J=18 Hz,CH$_2$), 4.35-4.60(2 H,m,CH$_2$), 5.28(1 H,d,J=4.7 Hz,CH), 5.60-5.75(1 H,m,—CH=), 5.80(1 H,dd,J=4.7 Hz,7.7 Hz,CH), 5.81(2 H,s,CH$_2$), 6.27(1 H,d,J=11.7 Hz,—CH=), 6.83(1 H,s,thiazole-H), 7.15(1 H,t,J=3.3 Hz,NH), 9.68(1 H,d,J=7.7 Hz,NH).

EXAMPLE 44

Sodium 7-[(Z)-2-(2-aminothiazol-4-yl)-2-hydroxyiminoacetamido]-3-[(Z)-3-(N-(2-chloroethyl)carbamoyloxy)-1-propenyl]-3-cephem-4-carboxylate

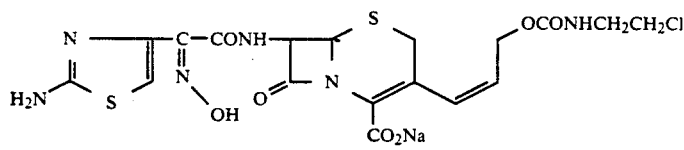

To a solution of the compound (0.6 g; 0.53 mmol), which had been obtained in Preparation Example 28, in anisole (3 ml), trifluoroacetic acid (3 ml) was added dropwise under ice cooling. The resulting mixture was stirred at room temperature for 2 hours. The reaction mixture was concentrated under reduced pressure and the concentrate was added dropwise to a mixed solvent of isopropyl ether (20 ml) and n-hexane (80 ml). Precipitated crystals were collected by filtration. The crystals were added to 90% formic acid (10 ml), followed by stirring at room temperature for 3 hours. Under reduced pressure, the solvent was distilled off. The residue was triturated in isopropyl ether and crystals were collected by filtration. Those crystals were dissolved in methanol (20 ml), followed by the addition of sodium acetate (300 mg; 5 mmol). Under reduced pressure, the solvent was distilled off. The crude product was triturated in 2-propanol and crude crystals were collected by filtration. The crude crystals were purified by ODS column chromatography (7% aqueous methanol). Eluate was concentrated under reduced pressure and then lyophilized, whereby the title compound (140 mg; 0.25 mmol; 48%) was obtained.

NMR (DMSO-$d_6$) δ: 3.38(2 H,m,NHCH$_2$), 3.59(2 H,t,J=6.8 Hz,CH$_2$Cl), 3.53(2 H,ABq,J=16.5 Hz,CH$_2$), 4.60(2 H,d,ABq,J=7 Hz,13.9 HZ,CH$_2$), 5.03(1 H,d,J=4.8 Hz,CH), 5.03(1 H,m,—CH=), 5.58(1 H,dd,J=4.8 Hz,8.4 Hz,—CH), 6.64(1 H,d,J=12.8 Hz,—CH=), 6.65(1 H,s,thiazole-H), 7.09(2 H,s,NH$_2$).

EXAMPLE 45

Pivaloyloxymethyl 7-[(Z)-2-(2-aminothiazol-4-yl)-2-hydroxyiminoacetamido]-3-[(Z)-3-(N-(2-chloroethyl)carbamoyloxy)-1-propenyl]-3-cephem-4carboxylate

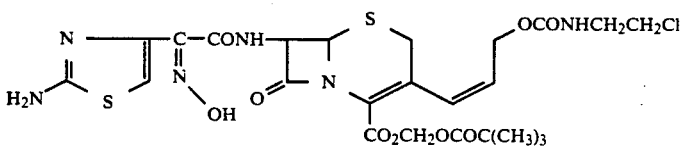

To a solution of the compound (80 mg; 0.14 mmol), which had been obtained in Example 44, in dry dimethylformamide (3 ml), a solution of iodomethyl pivalate (37 mg; 0.16 mmol) in dry dimethylformamide (0.5 ml) was added dropwise under ice cooling. The resulting mixture was stirred for 30 minutes. Ethyl acetate was added to the reaction mixture. The resulting mixture was washed with water and then with saturated saline. Magnesium sulfate was added to dry the mixture. The mixture was concentrated under reduced pressure and the concentrate was added dropwise to n-hexane (50 ml). Precipitated crystals were collected by filtration and then dried, whereby the title compound (63 mg; 0.1 mmol; 71%) was obtained.

NMR (DMSO-$d_6$) δ: 1.15(9 H,s,C(CH$_3$)3), 3.29(2 H,dt,J=5.9 Hz,12.1 Hz,NHCH$_2$), 3.58(2 H,t,J=12.1 Hz,CH$_2$Cl), 3.5–3.9(2 H,m,CH$_2$), 4.3–4.6(2 H,m,CH$_2$), 5.28(1 H,d,J=4.7 Hz,CH), 5.5–5.65(1H,m,=CH—) 5.77(1 H,dd,J=4.7 Hz,7.8Hz,CH), 5.84(2 H,ABq,J=3.3 Hz,CH$_2$O), 6.29(1 H,d,J=11.7 Hz,—CH=), 6.83(1 H,s,thiazole-H), 7.45(1 H,t,J=5.9 Hz,NH), 9.68(1 H,d,J=7.8 Hz,NH).

EXAMPLE 46

Sodium 7-[(Z)-2-(2-aminothiazol-4-yl)-2-hydroxyiminoacetamido]-3-[(Z)-30(N-allylcarbamoyloxy)-1-propenyl] -3-cephem-4-carboxylate

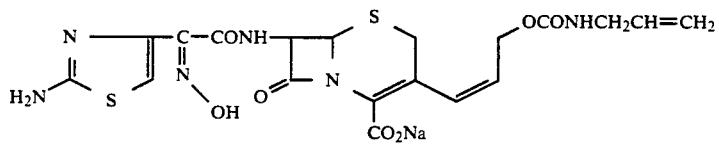

To a solution of the compound (1 g; 0.9 mmol), which had been obtained in Preparation Example 29, in anisole (3 ml), trifluoroacetic acid (3 ml) was added dropwise under ice cooling. The resulting mixture was stirred at room temperature for 2 hours. The reaction mixture was concentrated under reduced pressure and the concentrate was added dropwise to a mixed solvent of isopropyl ether (20 ml) and n-hexane (80 ml). Precipitated crystals were collected by filtration. The crystals were added to 90% formic acid (10 ml), followed by stirring at room temperature for 3 hours. Under reduced pressure, the solvent was distilled off. The residue was triturated in isopropyl ether and the crystals were collected by filtration. Those crystals were dissolved in methanol (20 ml), followed by the addition of sodium acetate (300 mg; 5 mmol). Under reduced pressure, the solvent was distilled off. The crude product was triturated in 2-propanol and crude crystals were collected by filtration. The crude crystals were purified by ODS column chromatography (10% aqueous methanol). Eluate was concentrated under reduced pressure and then lyophilized, whereby the title compound (80 mg; 0.15 mmol; 17%) was obtained.

NMR (D$_2$O-d$_6$) δ: 3.62(2 H,ABq,J=17 Hz,CH$_2$), 3.84(2 H,d,J=4.8 Hz,NHCH$_2$), 4.55–4.85(2 H,m,CH$_2$), 4.87(2 H,ABq,J=17.1 Hz,CH$_2$), 5.25(1 H,dd,J=1.5 Hz,10.3 Hz,=CH$_2$), 5.30(1 H,dd,J=1.5 Hz,17.2 Hz,=CH$_2$), 5.42(1 H,d,J=4.7 Hz,CH), 5.78–5.87(1 H,m,=CH—), 5.92–6.03(1 H,m,—CH=), 5.97(1 H,d,J=4.7 Hz,CH), 6.32(1 H,d,J=11.8 Hz,—CH=), 7.12(1 H,s,thiazole-H).

EXAMPLE 47

Pivaloyloxymethyl 7-[(Z)-2-(2-aminothiazol-4-yl)-2-hydroxyiminoacetamido]-3-[(Z)-3-(N-(2-allylcarbamoyloxy)-1-propenyl]-3-cephem-4-carboxylate

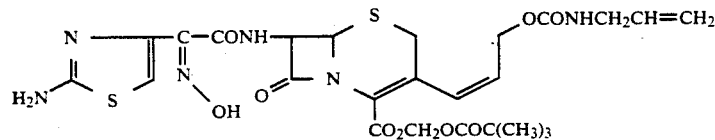

To a solution of the compound (50 mg; 0.09 mmol), which had been obtained in Example 46, in dry dimethylformamide (3 ml), a solution of iodomethyl pivalate (24 mg; 0.1 mmol) in dry dimethylformamide (0.5 ml) was added dropwise under ice cooling. The resulting mixture was stirred for 30 minutes. Ethyl acetate was added to the reaction mixture. The resulting mixture was washed with water and then with saturated saline. Magnesium sulfate was added to dry the mixture. The mixture was concentrated under reduced pressure and the concentrate was added dropwise to n-hexane (50 ml). Precipitated crystals were collected by filtration and then dried, whereby the title compound (35 mg; 0.06 mmol; 61%) was obtained.

NMR (DMSO-d$_6$) δ: 1.15(9 H,s,C(CH$_3$)3), 3.55–3.77(4 H,m,CH$_2$CH$_2$), 4.35–4.65(2 H,m,CH$_2$), 5.04(1 H,dd,J=1.4 Hz,10.2 Hz,=CH$_2$), 5.10(1 H,dd,J=1.4 Hz,17.2 Hz,=CH$_2$), 5.25(1 H,d,J=5.1 Hz,CH), 5.60–5.70(1 H,m,—CH=), 5.70–5.90(4 H,m,—CH=,OCH$_2$CH), 6.27(1 H,d,J=11.7 Hz,—CH=), 6.67(1 H,s,thiazole-H).

PREPARATION EXAMPLE 30

4-Methoxyphenylmethyl 7β-[(Z)-2-(2-tritylaminothiazol-4-yl)-2-methoxyiminoacetamido]-3-[(Z)-2-(tetrahydrofuran-2-yl)vinyl]-3-cephem-4-carboxylate

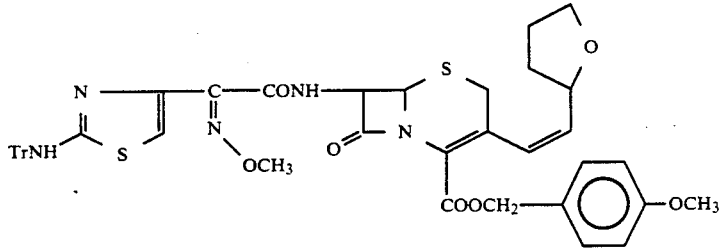

4-Methoxyphenylmethyl 7β-[(Z)-2-(2-tritylaminothiazol-4-yl)-2-methoxyiminoacetamido]-3-(triphenylphosphoranyliden)-methyl-3-cephem-4-carboxylate (34.4 g) and tetrahydrofuran-2-aldehyde (6.0 g) were dissolved in dichloromethane (400 ml), followed by stirring at room temperature for 29 hours. The solvent was concentrated under reduced pressure and the residue was purified by silica gel chromatography (benzene:ethyl acetate=9:1), whereby the title compound (10.5 g) was obtained.

| NMR (CDCl$_3$) δ: |
| --- |
| 1.5–2.1(4H, m), |
| 3.35, 3.54(1H, ABq, 18.5Hz) ⎫ diastereomer, |
| 3.47, 3.51(1H, ABq, 18.5Hz) ⎭ |
| 3.7–3.9(2H, m), 3.80(3H, s), 4.07(3H, s), 4.30(1H, m), |
| 5.06(1H, d, J=4.8Hz, 6-position), 5.17(2H, s), |
| 5.55(0.5H, dd, J=4Hz, 8.4Hz), |
| 5.60(0.5H, dd, J=11.4Hz, 8.4Hz), |
| 5.90(1H, dd, J=4.8Hz, 8Hz, 7-position), |
| 6.21(0.5H, d, J=11.5Hz), 6.27(0.5H, d, J=11.5Hz), |
| 6.87(2H, d, J=7.8Hz), 7.01(0.5H, s), 7.07(0.5H, s), |
| 7.1–7.4(17H, m) |

PREPARATION EXAMPLE 31

4-Methoxyphenylmethyl 7β-[(Z)-2-(2-tritylaminothiazol-4-yl)-2-methoxyiminoacetamido]-3-[(Z)-2-(5-oxotetrahydrofuran-2-yl)vinyl]-3-cephem-4-carboxylate

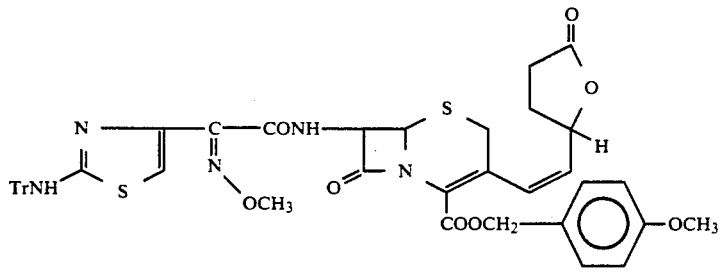

4-Methoxyphenylmethyl 7β-[(Z)-2-(2-tritylaminothiazol-4-yl)-2-methoxyiminoacetamido]-3-(triphenylphosphoranyliden)-methyl-3-cephem-4-carboxylate (13.4 g) and 5-oxotetrahydrofuran-2-aldehyde (1.6 g) were dissolved in dichloromethane (150 ml), followed by stirring at room temperature for hours. The solvent was concentrated under reduced pressure and the residue was purified by silica gel chromatography (benzene:ethyl acetate=9:1), whereby two kinds of the title compound [(A) (Rf value: large): 3.06 g; (B) (Rf value: small): 2.46 g] were obtained.

NMR (CDCl₃) δ:

(A) (Rf value: large) 1.90–2.05(1 H,m), 2.30–2.60(3 H,m), 3.27, 3.55(2 H,ABq,J=18.5 Hz), 3.80(3 H,s), 4.07(3 H,s), 4.80–4.85(1 H,m), 5.07(1 H,d,J=4.8 Hz), 5.10–5.20(2 H,m), 5.55(1 H,dd,J=11.4 Hz,8.4 Hz), 5.90(1 H,dd,J=4.8 Hz,8 Hz), 6.35(1 H,d,J=11.4 Hz), 7.07(1 H,s).

(B) (Rf value: small) 1.85–1.95(1 H,m), 2.30–2.60(3 H,m), 3.35,3.55(2 H,ABq,J=18.5 Hz), 3.80(3 H,s), 4.07(3 H,s), 4.85–4.93(1 H,m), 5.05(1 H,d,J=4.8 Hz), 5.10–5.20(2 H,m), 5.60(1 H,dd,J=11.2 Hz,8.4 Hz), 5.90(1 H,dd,J=4.8 Hz,8 Hz), 6.36(1 H,d,J=11.2 Hz), 7.05(1 H,s).

PREPARATION EXAMPLE 32

4-Methoxyphenylmethyl 7β-[2-(5-tritylamino-1,2,4-thiadiazol-3-yl)-(Z)-2-methoxyiminoacetamido]-3-[(Z)-2-(tetrahydrofuran-2-yl)vinyl]-3-cephem-4-carboxylate

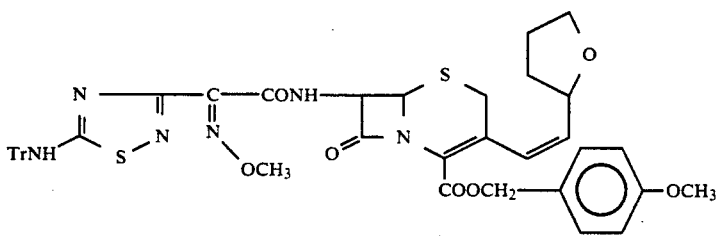

4-Methoxyphenylmethyl 7β-[2-(5-tritylamino-1,2,4-thiadiazol-3-yl)-(Z)-2-methoxyiminoacetamido]-3-(triphenylphosphoranyliden)-methyl-3-cephem-4-carboxylate (10 g) and tetrahydrofuran 2-aldehyde (1 g) were dissolved in dichloromethane (100 ml), followed by stirring at room temperature for 16 hours.

The solvent was concentrated under reduced pressure and the residue was purified by chromatography on a silica gel column (benzene:ethyl acetate=9:1), whereby the title compound (1.8 g) was obtained.

NMR (CDCl₃) δ: 1.5–2.1(4 H,m), 3.45,3.57(2 H,ABq,J=18.5 Hz), 3.7–3.9(2 H,m), 3.79(3 H,s), 4.10(3 H,s), 4.25–4.35(1 H,m), 5.04(1 H,d,J=4.7 Hz), 5.1–5.2(3 H,m), 5.59(1 H,m), 5.92(1 H,dd,J=4.7 Hz,8.0 Hz), 6.25(1 H,d,J=11.2 Hz), 6.85(2 H,d,J=8 Hz), 6.86(1 H,s), 7.1–7.4(17 H), 7.77(1H,s).

EXAMPLE 48

Sodium 7β-[(Z)-2-aminothiazol-4-yl-2-methoxyiminoacetamido]-3-[(E)-2-(tetrahydrofuran-2yl)vinyl]-3-cephem-4-carboxylate

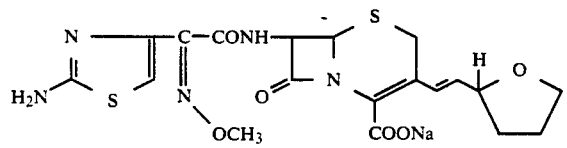

The compound (4.6 g) obtained in Preparation Example 30 was added to anisole (28 ml) and trifluoroacetic acid (32.2 ml), followed by stirring under ice cooling for 2 hours. Isopropyl ether (350 ml) was added, and precipitated crystals were collected by filtration. The crystals were dried and then added to a 5% aqueous solution of sodium hydrogencarbonate. Insoluble matter was filtered off and purification was conducted by reversed-phase silica gel chromatography (methanol:H₂O=15:85), whereby optical isomers (A) (Rf value: large; 290 mg) and (B) (Rf value: small; 273 mg) of the title compound were obtained.

NMR (DMSO-d₆) δ:

(A) 1.5–2.0(4 H,m), 3.41,3.48(2 H,ABq,J=16.9 Hz,2-position), 3.62(1 H,m), 3.76(1 H,m), 3.84(3 H,s), 4.20(1 H,m), 5.02(1 H,d,J=5.1 Hz,6-position), 5.54–5.60(2 H,m), 6.74(1 H,s), 6.92(1 H,d), 7.21(2 H,s), 9.53(1 H,d,J=8 Hz).

(B) 1.5-2.0(4 H,m), 3.40,3.46(2 H,ABq,J=16.9 Hz,2-position), 3.63(1 H,m), 3.77(1 H,m), 3.84(3 H,s), 4.20(1 H,m), 4.99(1 H,d,J=4.8 Hz,6-position), 5.53-5.59(2 H,m,7-position), 6.73(1 H,s), 6.91(1 H,d), 7.20(2 H,s), 9.53(1 H,d,J=8 Hz).

EXAMPLE 49

Sodium 7β-[(Z)-2-aminothiazol-4-yl-2-methoxyiminoacetamido]-3-[(Z)-2-(tetrahydrofuran-2-yl)vinyl]-3-cephem-4-carboxylate

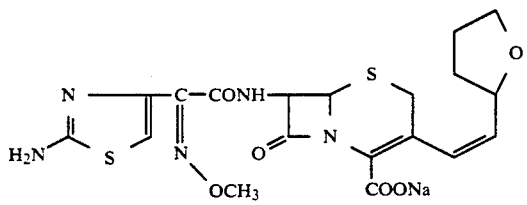

The compound (3.25 g) obtained in Preparation Example 30 was added to anisole (19.5 ml) and trifluoroacetic acid (39 ml), followed by stirring under ice cooling for 35 minutes. Isopropyl ether (400 ml) was added, and precipitated crystals were collected by filtration. The crystals were dried and then dissolved in methyl alcohol (300 ml). Sodium acetate (1.8 g) was added, followed by stirring for 5 minutes. The methyl alcohol was distilled off and isopropyl alcohol was added to the residue. Insoluble matter was collected by filtration and washed with isopropyl ether. After the insoluble matter was dried, it was dissolved in water. Insoluble matter was filtered off and purification was conducted by reversed-phase silica gel chromatography (methanol:-H₂O=15:85) whereby the title compound (98 mg) was obtained.

NMR (D₂O) δ: 1.4-2.05(4 H,m), 3.27,3.57(2 H,ABq,J=19 Hz,2-position), 3.62(1 H,m), 3.72(1 H,m), 4.40(1 H,m), 5.11(1 H,d,J=4.8 Hz,6-position), 5.46(1 H,m), 5.66(1 H,d,J=4.8 Hz,7-position), 6.07(1 H,d,J=11.5 Hz), 6.90(1 H,s).

EXAMPLE 50

Sodium 7β-[(Z)-2-aminothiazol-4-yl-2-hydroxyiminoacetamido]-3-(E)-2-(tetrahydrofuran-2-yl)vinyl]-3-cephem-4-carboxylate

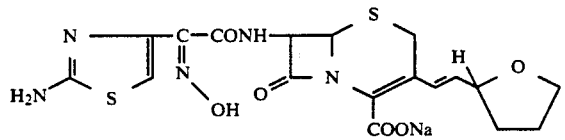

4-Methoxyphenylmethyl 7β-[(Z)-2-(2-tritylaminothiazol-4-yl)-2-trityloxyiminoacetamido]-3-(triphenylphosphoranyliden)-methyl-3-cephem-4-carboxylate (16.3 g) and tetrahydrofuran-2-aldehyde (2.9 g) were dissolved in dichloromethane (200 ml), followed by stirring at room temperature for 20 hours. The solvent was concentrated under reduced pressure and the residue was purified by silica gel chromatography (benzene:ethyl acetate=9:1), whereby the compound (5.4 g) was obtained.

Anisole (16.8 ml) and trifluoroacetic acid (19.6 ml) were added to the compound, followed by stirring under ice cooling for 2 hours. Isopropyl ether (200 ml) was added, and precipitated crystals were collected by filtration. After the crystals were dried, a 90% aqueous solution (22.5 ml) of formic acid was added and the resulting mixture was stirred at room temperature for 3 hours. The solvent was distilled off under reduced pressure and a saturated aqueous solution of sodium acetate was added to the residue. Insoluble matter was filtered off and purification was conducted by reversed-phase silica gel chromatography (methanol:H₂O=15:85), whereby optical isomers (A) (Rf value: large; 25 mg) and (B) (Rf value: small; 25 mg) were obtained.

NMR (D₂O) δ:

(A) 1.48-2.03(4 H,m), 3.40(2 H,m,2-position), 3.62(1 H,m), 3.75(1 H,m), 4.19(1 H,m), 4.99(1 H,d,J=5.1 Hz,6-position), 5.51-5.57(2 H,m,7-position), 6.67(1 H,s), 6.87(1 H,d,J=16.1 Hz), 7.08(2 H,br,H2N), 11.25(1 H,br);

(B) 1.48-1.99(4 H,m), 3.40(2 H,m,2-position), 3.63(1 H,m), 3.77(1 H,m), 4.19(1 H,m), 4.98(1 H,d,J=5.1 Hz,6-position), 5.50-5.58(2 H,m,7-position), 6.66(1 H,s), 6.89(1 H,d,J=15.8 Hz), 7.09(2 H,s), 9.40(1 H,br), 11.26(1 H,br).

EXAMPLE 51

Pivaloyloxymethyl 7β-[(Z)-2-aminothiazol-4-yl-2-methoxyiminoacetamido]-3-[(E)-2-(tetrahydrofuran-2-yl)vinyl]-3-cephem-4-carboxylate

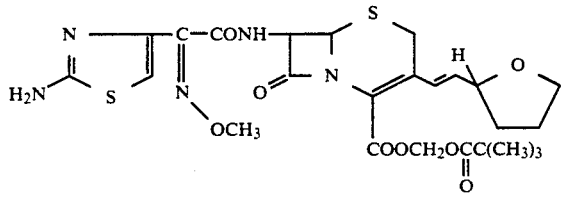

To a solution of the compound (A) (100 mg), which had been obtained in Example 48, in N,N-dimethylacetamide (5 ml), a solution of iodomethyl pivalate (55 mg) in N,N-dimethylacetamide (1 ml) was added dropwise, followed by stirring for 30 minutes. Ethyl acetate was added to the reaction mixture. The resulting mixture was washed with water and then with saturated saline, and thereafter dried over magnesium sulfate.

Under reduced pressure, the solvent was concentrated. Ethyl acetate (2 ml) and isopropyl ether (50 ml) were added to the residue. Precipitated crystals were collected by filtration and then dried, whereby the title compound (98 mg) was obtained.

NMR (CDCl₃) δ: 1.23(9 H,s), 1.6-2.2(4 H,m), 3.57, 3.73(2 H,ABq,2-position), 3.83(1 H,m), 3.92(1 H,m), 4.22(3 H,s), 4.43(1 H,m), 5.13(1 H,d,J=4 Hz), 5.85-6.1(4 H,m), 6.98(1 H,s), 7.04(1 H,d,J=15.8 Hz), 7.25(2 H,s), 7.50(1 H,d,J=8 Hz)

Similarly, iodomethyl pivalate (27.5 mg) was reacted to the compound (B) (50 mg), whereby the title compound (B) (51 mg) [optical isomer of (A)] was obtained.

NMR (CDCl₃) δ: 1.23(9 H,s), 1.55-2.15(4 H,m), 3.56, 3.71(2 H,ABq,J=18 Hz,2-position), 3.82(1 H,m), 3.94(1 H,m), 4.10(3 H,s), 4.45(1 H,m), 5.09(1 H,d,J=4.7 Hz,6-position), 5.86-5.93(3 H,m), 6.04(1 H,dd,J=15.6 Hz,5.7 Hz), 7.00(1 H,s), 7.04(1 H,d,J=15.6 Hz), 7.55(1 H,br).

EXAMPLE 52

Sodium 7β-[(Z)-2-aminothiazol-4-yl-2-methoxyiminoacetamido]-3-[(E)-2-(5-oxotetrahydrofuran 2-yl)vinyl]-3-cephem-4-carboxylate

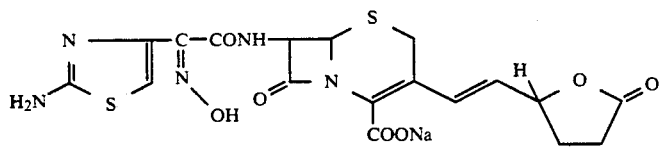

The two kinds of the compound (6.9 g), which had been obtained in Preparation Example 31, were added to anisole (34 ml) and trifluoroacetic acid (51 ml), followed by stirring under ice cooling for 2 hours. Isopropyl ether (200 ml) was added, and precipitated crystals were collected by filtration.

After the crystals were dried, a 90% aqueous solution (90 ml) of formic acid was added. The resulting mixture was stirred at room temperature for 3 hours. After the solvent was distilled off under reduced pressure, a saturated aqueous solution of sodium acetate was added. Insoluble matter was filtered off and purification was conducted by reversed-phase silica gel chromatography, whereby the title compound (371 mg) was obtained as a diastereomer.

NMR (D$_2$O) δ: 1.9-2.0(1 H,m), 2.27-2.40(1 H,m), 2.45-2.60(2 H,m), 3.45-3.60(2 H,m), 3.89(3 H,s), 5.05-5.15(2 H,m), 5.65-5.70(1 H,m), 5.81(1 H,dd,J=7.3 Hz,15.9 Hz), 6.65(1 H,d,J=15.9 Hz), 6.86(1 H,s).

EXAMPLE 53

Pivaloyloxymethyl 7β-[(Z)-2-aminothiazol-4-yl-2-methoxyiminoacetamido]-3-[(E)-2-(5 oxotetrahydrofuran-2-yl)vinyl]-3-cephem-4-carboxylate

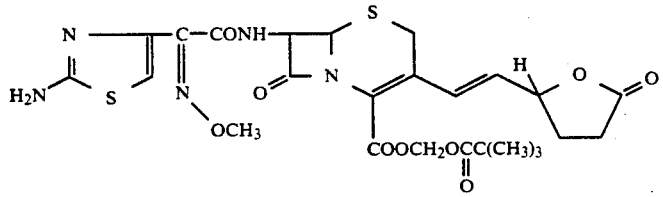

To a solution of the compound (150 mg), which had been obtained in Example 52, in N,N-dimethylacetamide (3.8 ml), a solution of iodomethyl pivalate (70 mg) in N,N-dimethylformamide (0.1 ml) was added dropwise, followed by stirring for 30 minutes. Ethyl acetate was added to the reaction mixture. The resulting mixture was washed with water and then with saturated saline, and thereafter dried over magnesium sulfate.

Under reduced pressure, the solvent was concentrated. Ethyl acetate (2 ml), 10% (W/W) hydrochloric acid-ethyl acetate (0.2 ml) and isopropyl ether (50 ml) were added to the residue. Precipitated crystals were collected by filtration and then dried, whereby the title compound (157 mg) was obtained.

NMR (DMSO-d$_6$) δ: 1.15(3 H,s), 1.85-1.98(1 H,m), 2.30-2.60(1 H,m), 3.90(3 H,s), 5.05(1 H,d,J=4.9 Hz), 5.20-5.25(1 H,m), 5.80-5.90(3 H,m), 6.27(1 H,dd,J=4.9 Hz,8 Hz), 6.77(1 H,d,J=15 Hz), 6.88(1 H,s), 9.80(1 H,d,J=8 Hz).

EXAMPLE 54

2-Ethylbutanoyloxymethyl 7β-[(Z)-2-aminothiazol-4-yl-2-methoxyiminoacetamido]-3-[(E)-2-(5-oxotetrahydrofuran-2-yl)vinyl]-3-cephem-4-carboxylate

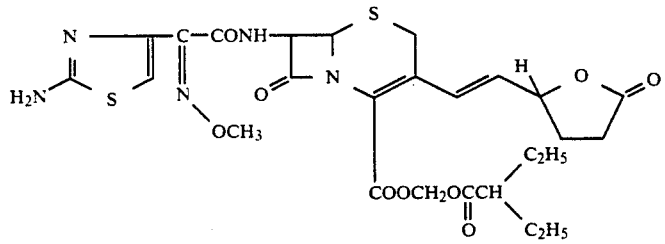

To a solution of the compound (90 mg), which had been obtained in Example 52, in N,N-dimethylacetamide (2 ml), a solution of iodomethyl-2-ethyl butyrate (45 mg) in dry N,N-dimethylformamide (0.1 ml) was added dropwise, followed by stirring for 30 minutes. Ethyl acetate was added to the reaction mixture. The resulting mixture was washed with water and then with saturated saline, and thereafter dried over magnesium sulfate.

Under reduced pressure, the solvent was concentrated. Ethyl acetate (2 ml) and isopropyl ether (50 ml) were added to the residue. Precipitated crystals were collected by filtration and then dried, whereby the title compound (89 mg) was obtained.

NMR (DMSO-d$_6$) δ: 0.75-0.85(6 H,m), 1.40-1.60(4 H,m), 1.93-2.00(1 H,m), 2.20-2.65(m), 3.83(3 H,s), 5.05(1 H,d,J=4.9 Hz, 5.20-5.23(1 H,m), 5.80-5.90(3 H,m), 6.24(1 H,dd,J=4.9 Hz,8 Hz), 6.74(1 H,s), 6.78(1 H,d,J=15 Hz), 7.10(2 H,s), 9.65(1 H,d,J=8 Hz).

EXAMPLE 55

Sodium 7β-[(Z)-2-aminothiazol-4-yl-2-hydroxyiminoacetamido]-3-[(E)-2-(5-oxotetrahydrofuran-2-yl)vinyl]-3-cephem-4-carboxylate

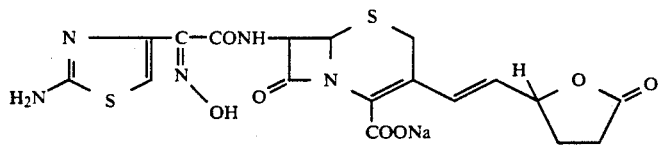

Similarly to Example 50, 7β-[(Z)-2-(2-tritylaminothiazol-4-yl)-2-trityloxyiminoacetamido]-3-(triphenylphosphoranyliden)-methyl-3-cephem-4-carboxylic acid (16.3 g) and 5-oxotetrahydrofuran-2-aldehyde (1.6 g) were dissolved in dichloromethane (200 ml), followed by stirring at room temperature for 10 hours. The solvent was concentrated under reduced pressure and the residue was purified by silica gel chromatography (benzene:ethyl acetate=9:1), whereby the compound (5.4 g) was obtained.

Anisole (27 ml) and trifluoroacetic acid (41 ml) were added to the compound, followed by stirring under ice cooling for 2 hours. Isopropyl ether (200 ml) was added, and precipitated crystals were collected by filtration. After the crystals were dried, a 90% aqueous solution (100 ml) of formic acid was added and the resulting mixture was stirred at room temperature for 1.5 hours. The solvent was distilled off under reduced pressure and a saturated aqueous solution of sodium acetate was added to the residue. Insoluble matter was filtered off and purification was conducted by reversed-phase silica gel chromatography (methanol:H$_2$O=15:85), whereby the title compound (2.35 mg) was obtained.

NMR (D$_2$O ) δ: 1.90–2.03(1 H,m), 2.30–2.42(1 H,m), 2.45–2.60(2 H,m), 3.45–3.60(2 H,m), 5.05–5.15(2 H,m), 5.70–5.75(1 H,m), 5.85(1 H,dd,J=7.3 Hz,15.9 Hz), 6.67(1 H,d,J=15.9 HZ), 6.87(0.5 H,s), 6.88(0.5 H,s).

EXAMPLE 56

Sodium 7β-[2-(5-amino-1.2,4-thiadiazol-3-yl)-(Z)-2-methoxyiminoacetamido]-3-(E)-2-(tetrahydrofuran-2-yl)vinyl]-3-cephem-4-carboxylate

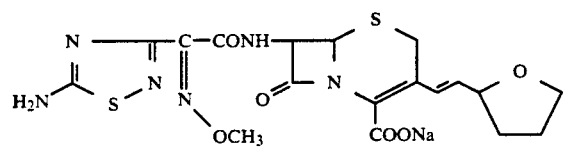

The compound (1.8 g) obtained in Preparation Example 32 was added to anisole (5 ml) and trifluoroacetic acid (8 ml), followed by stirring at room temperature for 2 hours. After the reaction mixture was concentrated under reduced pressure, isopropyl ether (50 ml) was added and crystals precipitated were collected by filtration. The crystals were dried and added to a 5% aqueous solution of sodium hydrogencarbonate. Insoluble matter was filtered off and purification was conducted by reverse-phase silica gel chromatography (methanol:H$_2$O=15:85), whereby optical isomers (A) (Rf value: large; 30 mg) and (B) (Rf value: small; 33 mg) were obtained.

NMR (DMSO-d$_6$) δ:
Isomer (A) 1.5–2.04(4 H,m), 3.65–3.82(2 H,m,2-position), 3.68(3 H,s), 4.22(1 H,m), 5.04(1 H,d,J=5.4 Hz,6-position), 5.55–5.65(2 H,m), 6.93(1 H,d,J=15.4 Hz), 8.16(2 H,s), 9.52(1 H,d,J=10 Hz).
Isomer (B) 1.5–2.00(4 H,m), 3.2–3.5(2 H,m,2-position), 3.6–3.8(2 H,m), 3.90(3 H,s), 4.1–4.2(1 H,m), 4.96(1 H,d,J=5.0 Hz,6-position), 5.5–5.6(2 H,m), 6.84(1 H,d,J=16 Hz), 8.1(2 H,s), 9.50(1 H,d,J=10 Hz).

PREPARATION EXAMPLE 33

4-Methoxyphenylmethyl 7β-[(Z)-2-(2-tritylaminothiazol-4-yl)-2-trityloxyiminoacetamido]-3-[(Z)-cyclopropylvinyl]-3-cephem-4-carboxylate

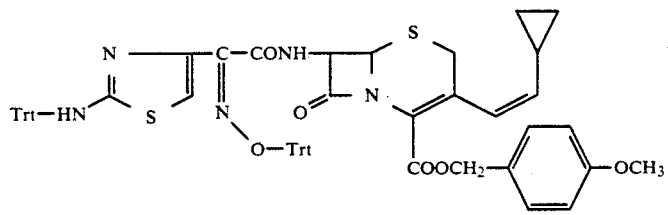

4-Methoxyphenylmethyl 7β-[(Z)-2-(2-tritylaminothiazol-4-yl)-2-trityloxyiminoacetamido]-3-(triphenylphosphoranyliden)methyl-3-cephem-4-carboxylate (8.2 g) and cyclopropanecarboxaldehyde (5 ml) were dissolved in dichloromethane (40 ml), followed by stirring at room temperature for 16 hours. After the solvent was distilled off under reduced pressure, the residue was purified by chromatography on a silica gel column whereby the title compound (1.1 g) was obtained.

NMR (CDCl$_3$) δ: 0.40(2 H,m), 0.80(2 H,m), 1.40(1 H,m), 3.36(2 H,ABq,J=18.0 Hz), 3.78(3 H,s), 4.80–5.05(2 H,m), 5.14(2 H,s), 5.80–6.15(2 H,m), 6.40(1 H,s), 6.70–7.40(35 H,m).

EXAMPLE 57

Sodium 7β-[(Z)-2-(2-aminothiazol-4-yl)-2-hydroxyiminoacetamido]-3-[(Z)-cyclopropylvinyl]-3-cephem-4-carboxylate

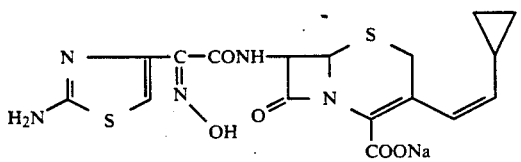

The compound (1.1 g) of Preparation Example 33 was dissolved in anisole (6 ml). After trifluoroacetic acid (8 ml) was added dropwise under ice cooling, the resulting mixture was stirred at room temperature for 2 hours. The trifluoroacetic acid was distilled off under reduced pressure and the residue was added dropwise to a mixed solvent of isopropyl ether (20 ml) and n-hexane (80 ml). Precipitated crystals were collected by filtration.

The crystals were added to 90% formic acid (8 ml), followed by stirring at room temperature for 3 hours. The solvent was distilled off under reduced pressure. The residue was triturated in isopropyl ether and crystals were collected by filtration.

They were dissolved in methanol (10 ml), followed by the addition of sodium acetate (260 mg). The solvent was distilled off under reduced pressure. The crude product was triturated in 2-propanol and crude crystals were collected by filtration. The crude crystals were purified by reversed-phase chromatography on a silica gel, whereby the title compound (130 mg) was obtained.

NMR (DMSO-$d_6$) δ: 0.33(2 H,m), 0.76(2 H,m), 1.62(1 H,m), 3.69(2 H,ABq,J=16.5 Hz), 4.65(1 H,dd,J=11.7 Hz,9.9 Hz), 5.05(1 H,d,J=4.8 Hz), 5.57(1 H,dd,J=8.1 Hz,4.8 Hz), 6.53(1 H,d,J=11.7 Hz), 6.66(1 H,s), 7.10(2 H,s), 9.39(1 H,brs), 11.43(1 H,s).

EXAMPLE 58

Pivaloyloxymethyl 7-62-[(Z)-2-(2-aminothiazol-4-yl)-2-hydroxyiminoacetamido]-3-[(Z)-cyclopropylvinyl]-3-cephem-4-carboxylate

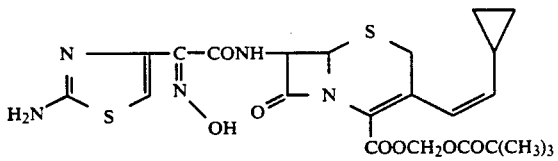

The compound (170 mg) of Example 57 was dissolved in dimethylformamide (2 ml). After a solution of pivaloyloxymethyl iodide (90 mg) in dimethylformamide (0.5 ml) was added dropwise under ice cooling, the resulting mixture was stirred for 30 minutes. The reaction mixture was added with ethyl acetate, followed by washing with water and then with saturated saline. The resulting solution was added with anhydrous magnesium sulfate and activated carbon, whereby the solution was dried and decolorized. The solvent was distilled off. The residue was purified by chromatography on a silica gel column, whereby the title compound (74 mg) was obtained.

NMR (CDCl$_3$) δ: 0.49(2 H,m), 0.86(2 H,m), 1.22(9 H,s), 1.43(1 H,m), 3.64(2 H,ABq,J=17.8 HZ), 5.06(1 H,t,J=11.0 Hz), 5.14(1 H,d,J=5.2 Hz), 5.82(2 H,brs), 5.92(1 H,d,J=5.2 Hz), 6.17(1 H,d,J=11.0 Hz), 7.07(1 H,s), 10.70(1 H,brs).

EXAMPLE 59

1-Acetoxyethyl 7β-[(Z)-2-(2-aminothiazol-4-yl)-2-hydroxyiminoacetamido]-3-[(Z)-cyclopropylvinyl]-3-cephem-4-carboxylate

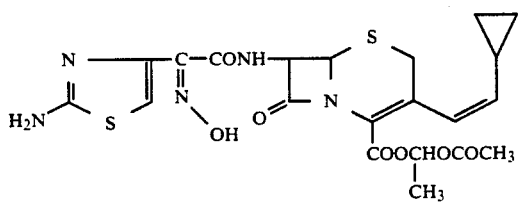

The compound (318 mg) of Example 57 was dissolved in dimethylformamide (4.4 ml), to which a solution of 1-acetoxyethyl bromide (120 mg) in dimethylformamide (2 ml) was added dropwise under ice cooling. The resulting mixture was stirred for one and a half hours. The reaction mixture was diluted with ethyl acetate and the resulting precipitate was filtered off. After the filtrate was washed with water and then saturated saline, anhydrous magnesium sulfate was added to dry the solution. The solvent was distilled off under reduced pressure and the residue was purified by chromatography on a silica gel, whereby the title compound (18 mg) was obtained.

NMR (CDCl$_3$) δ: 0.48(2 H,m), 0.84(2 H,m), 1.43(1 H,m), 1.53(3 H,d,J=5.5 Hz), 2.09(3 H,s), 3.64(2 H,ABq,J=17.6 Hz), 5.04(1 H,m), 5.13 and 5.14(1 H,d,J=5.3 Hz in total), 5.86(1 H,m), 6.21 and 6.24(1 H,d,J=12.1 Hz in total), 6.97 and 7.07(1 H,q,J=5.5 Hz in total), 7.05(1 H,s), 10.37(1 H,brs).

To demonstrate the usefulness of the compounds of this invention, the test data on antibacterial activities of the typical compounds of the present invention will be shown hereinafter by Experiment.

EXPERIMENT

In Vitro Antibacterial Activities

1. Compounds Tested

Typical compounds out of the compounds described in Examples were classified into some groups. On each compound group, in vitro antibacterial activities were tested by a method known per se in the art.

2. Results

The results are summarized in Tables 1–6.

TABLE 1

| Bacterium measured | Compound tested Antibacterial activities MIC, (μg/ml) Example | | | | | |
|---|---|---|---|---|---|---|
| | 1 | 7 | 9 | 11 | 12 | 13 |
| Staphylococcus aureus 209PJC1 | 0.1 | 0.8 | 0.1 | 0.1 | 0.1 | 0.1 |
| Escherichia coli MIHJ JC-2 | 0.025 | 0.2 | 0.05 | 0.1 | 0.1 | 0.1 |
| Klebsiella pneumoniae IID 875 | 0.012 | 0.025 | 0.012 | 0.05 | 0.1 | 0.025 |

TABLE 1-continued

| Bacterium measured | Compound tested Antibacterial activities MIC, (μg/ml) Example | | | | | |
|---|---|---|---|---|---|---|
| | 1 | 7 | 9 | 11 | 12 | 13 |
| Serratia marcescens IID 620 | 0.025 | 0.025 | 0.8 | 0.8 | 0.8 | 0.1 |
| Morganella morganii IID 602 | 0.012 | 0.025 | 0.1 | 0.05 | 0.05 | 0.05 |

TABLE 2

| Bacterium measured | Compound tested Antibacterial activities MIC, (μg/ml) Example | | | | | | | |
|---|---|---|---|---|---|---|---|---|
| | 14 | 16 | 21 | 23 | 25 | 27 | 29 (Z) | 29 (E) |
| Staphylococcus aureus 209-P | 0.8 | 0.2 | 0.2 | 0.2 | 0.2 | 0.8 | 1.56 | |
| Escherichia coli NIHJ | 0.4 | 0.1 | 0.2 | 0.4 | 0.8 | 0.2 | 3.13 | |
| Klebsiella pneumoniae EK-6 | 0.2 | 0.05 | 0.1 | 0.025 | 0.4 | 0.1 | 7.56 | |
| Serratia marcescens ES-75 | 0.8 | >100 | 0.2 | >100 | 0.2 | 0.05 | 3.13 | 6.25 |
| Morganella morganii EP-14 | 0.05 | 0.012 | 0.025 | 0.012 | 0.1 | 0.05 | 0.8 | 0.4 |

TABLE 3

| Bacterium measured | Compound tested Antibacterial activities MIC, (μg/ml) Example | |
|---|---|---|
| | 30 | 32 |
| Staphylococcus aureus 209-P | 0.2 | 0.2 |
| Escherichia coli NIHJ | 0.2 | 0.2 |
| Klebsiella pneumoniae EK-6 | 0.2 | 0.1 |
| Serratia marcescens ES-75 | 0.05 | — |
| Morganella morganii EP-14 | 0.05 | — |

TABLE 4

| Bacterium measured | Compound tested Antibacterial activities MIC, (μg/ml) Example | | | | | |
|---|---|---|---|---|---|---|
| | 33 | 38 | 40 | 42 | 44 | 46 |
| Staphylococcus aureus 209-P | 0.1 | 0.8 | 0.2 | 0.1 | 0.1 | 0.2 |
| Escherichia coli NIHJ | 0.025 | 0.2 | 0.1 | 0.05 | 0.05 | 0.1 |
| Klebsiella pneumoniae EK-6 | 0.012 | 0.05 | 0.1 | 0.05 | 0.05 | 0.05 |
| Serratia marcescens ES-75 | 0.025 | 0.05 | 0.05 | 0.05 | 0.05 | 0.05 |
| Morganella morganii EP-14 | ≦0.006 | 0.012 | 0.025 | ≦0.006 | ≦0.006 | 0.012 |

TABLE 5

| Bacterium measured | Compound tested Antibacterial activities MIC, (μg/ml) Example | | | | | | | | |
|---|---|---|---|---|---|---|---|---|---|
| | 48 A | 48 B | 49 | 50 A | 50 B | 52 | 53 | 54 A | 54 B |
| Staphylococcus aureus 209-P | 0.4 | 0.8 | 1.56 | 0.1 | 0.1 | 0.4 | 0.1 | 0.8 | 1.56 |
| Escherichia coli NIHJ | 0.4 | 0.8 | 0.8 | 0.2 | 0.8 | 0.1 | 0.025 | 0.8 | 3.13 |
| Klebsiella pneumoniae EK-6 | 0.2 | 0.4 | 0.4 | 0.2 | 0.4 | 0.025 | 0.025 | 0.4 | 1.56 |
| Serratia marcescens ES-75 | 0.025 | 0.1 | 0.05 | 0.1 | 0.4 | 0.012 | 0.05 | 0.1 | 0.8 |
| Morganella morganii EP-14 | 0.025 | 0.2 | 0.1 | 0.05 | 0.2 | ≦0.006 | 0.025 | 0.2 | 1.56 |

TABLE 6

| Bacterium measured | Compound tested Antibacterial activities MIC, (μg/ml) Example 58 |
|---|---|
| Staphylococcus aureus 209-P | 0.1 |
| Escherichia coli NIHJ | 0.4 |
| Klebsiella pneumoniae EK-6 | 0.2 |
| Serratia marcescens ES-75 | 0.8 |
| Morganella morganii EP-14 | 0.1 |

We claim:

1. A 3-substituted vinyl cephalosporin derivative represented by the following formula:

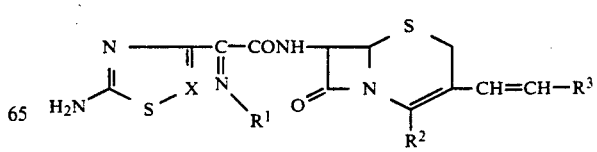

wherein $R^1$ represents a hydroxyl or lower alkoxy group;
$X$ represents —CH=;
$R^2$ represents a carboxyl group or a carboxyl group protected with a protecting group; and
$R^3$ represents:
(1) a group represented by the formula —CH$_2$OCONHR$^4$ wherein R$^4$ is a hydrogen atom, a lower alkyl group, a halogenated lower alkyl group or a lower alkenyl group, or
(2) a group represented by the formula

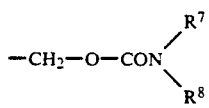

wherein $R^7$ and $R^8$ are the same or different and are individually a hydrogen atom, a lower alkyl group, a halogenated lower alkyl group or a lower alkenyl group or $R^7$ and $R^8$ may form a morpholino ring together with the nitrogen atom to which $R^7$ and $R^8$ are bonded, or a pharmaceutically acceptable salt thereof.

2. A derivative as claimed in claim 1, wherein $R^3$ is a group represented by the formula —CH$_2$OCONHR$^4$ wherein R$^4$ is a hydrogen atom or a lower alkyl group.

3. A derivative as claimed in claim 1, wherein $R^3$ is a group represented by the formula

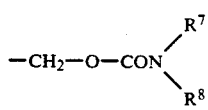

wherein $R^7$ and $R^8$ are the same or different and are individually a hydrogen atom, a lower alkyl group, a halogenated lower alkyl group or a lower alkenyl group or $R^7$ and $R^8$ may form a morpholino ring together with the nitrogen atom to which $R^7$ and $R^8$ are bonded.

4. A derivative as claimed in claim 1, wherein $R^3$ is a group represented by the formula

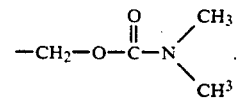

5. A derivative as claimed in claim 1, wherein $R^3$ is a group represented by the formula

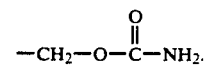

6. 7-[(Z)-2-(2-Aminothiazol-4-yl)-2-hydroxyiminoacetamido]-3-[(Z)-3-(N,N-dimethylcarbamoyloxy)-1-propenyl]-3-cephem-4-carboxylic acid represented by the following formula:

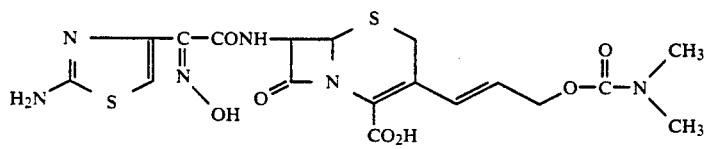

or a pharmaceutically acceptable salt thereof.

7. 7-[(Z)-2-(2-Aminothiazol-4-yl)-1 hydroxyiminoacetamido]-3-[(Z)-3-carbamoyloxy-1-propenyl]-3-cephem-4-carboxylic acid represented by the following formula:

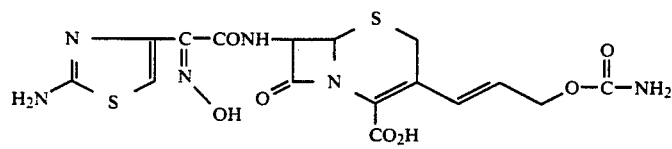

or a pharmaceutically acceptable salt thereof.

8. 7-[(Z)-2-(2-Aminothiazol-4yl)-2-methoxyiminoacetamido]-3-[(Z)-3-carmaboyloxy-1-propenyl]-3-cepham-4 carboxylic acid represented by the following formula:

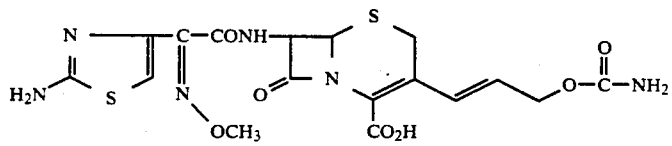

or a pharmaceutically acceptable salt thereof.

9. 7-[(Z)-2-(1-Aminothiazol-4-yl)-2-methoxyiminoacetamido]-3-[(Z)-3-(N-methylcarmaboyloxy)-1-propenyl]-3-cepham-4-carboxylic acid represented by the following formula:

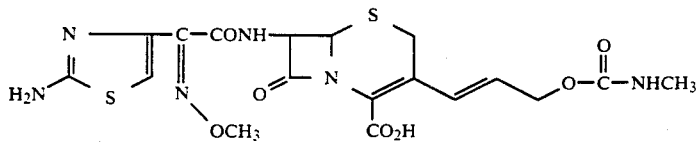

or a pharmaceutically acceptable salt thereof.

10. An antibacterial composition which comprises an antibacterially effective amount of a compound according to claim 1 or a pharmaceutically acceptable salt thereof and a pharmaceutically acceptable carrier therefor.

11. An antibacterial composition as claimed in claim 10, wherein said composition is for oral administration.

12. A method for the treatment or prevention of a disease wherein an agent is effective for the treatment or prevention, which comprises administering the patient suffering from such disease a therapeutically effective amount of a compound according to claim 1 or a pharmaceutically acceptable salt thereof.

* * * * *